(12) United States Patent
Bush, Jr. et al.

(10) Patent No.: US 12,171,502 B2
(45) Date of Patent: Dec. 24, 2024

(54) TOOL ASSEMBLY, SYSTEMS, AND METHODS FOR MANIPULATING TISSUE

(71) Applicant: MAKO Surgical Corp., Weston, FL (US)

(72) Inventors: Charles L. Bush, Jr., Wayne, NJ (US); Lori Dombrowski, Elmwood Park, NJ (US); Nicole R. Fallacaro, Montvale, NJ (US); Shawn Stad, Lakeville, MA (US); Paul Rochette, Stanhope, NJ (US); Peter L. Ebbitt, Boca Raton, FL (US)

(73) Assignee: MAKO Surgical Corp., Weston, FL (US)

( * ) Notice: Subject to any disclaimer, the term of this patent is extended or adjusted under 35 U.S.C. 154(b) by 288 days.

(21) Appl. No.: 17/939,097

(22) Filed: Sep. 7, 2022

(65) Prior Publication Data

US 2022/0409299 A1    Dec. 29, 2022

Related U.S. Application Data

(63) Continuation of application No. 16/290,177, filed on Mar. 1, 2019, now Pat. No. 11,464,577.
(Continued)

(51) Int. Cl.
*A61B 34/20* (2016.01)
*A61B 17/70* (2006.01)
(Continued)

(52) U.S. Cl.
CPC .......... *A61B 34/20* (2016.02); *A61B 17/7076* (2013.01); *A61B 34/30* (2016.02); *A61B 34/74* (2016.02); *A61B 2034/107* (2016.02)

(58) Field of Classification Search
CPC .......... A61B 34/20; A61B 34/30; A61B 34/74; A61B 17/7076; A61B 2034/107
See application file for complete search history.

(56) References Cited

U.S. PATENT DOCUMENTS 6,021,343 A    2/2000  Foley et al.
6,226,548 B1   5/2001  Foley et al.
(Continued)

FOREIGN PATENT DOCUMENTS

WO    2017127502 A1    7/2017
WO    2018209042 A2    11/2018

*Primary Examiner* — Nicholas J Plionis
(74) *Attorney, Agent, or Firm* — Howard & Howard Attorneys PLLC

(57) ABSTRACT

Tool assemblies, system, and methods for manipulating tissue and methods for performing a surgical procedure on a vertebral body adjacent soft tissue. A manipulator moves an end effector, and a screw is coupled to the end effector. A sleeve is disposed coaxially around the screw, and the screw and the sleeve are releasably engaged to one another. A navigation system is configured to track the vertebral body, and one or more controllers control the end effector to advance the screw relative to the sleeve along an insertion trajectory defined with respect to a surgical plan. The screw disengages the sleeve during advancement, and the screw is secured to the vertebral body. A distal working portion of the screw may be freely slidable through a distal end of the sleeve when disengaged. The screw may be a tap marker removably couplable with a tracking device of the navigation system.

20 Claims, 27 Drawing Sheets

Related U.S. Application Data

(60) Provisional application No. 62/637,472, filed on Mar. 2, 2018.

(51) Int. Cl.
*A61B 34/00* (2016.01)
*A61B 34/10* (2016.01)
*A61B 34/30* (2016.01)

(56) References Cited

U.S. PATENT DOCUMENTS

| | | |
|---|---|---|
| 6,582,439 B1 | 6/2003 | Sproul |
| 6,877,239 B2 | 4/2005 | Leitner et al. |
| 7,753,910 B2 | 7/2010 | Ritland |
| 7,766,920 B2 | 8/2010 | Ciccone et al. |
| 7,835,778 B2 | 11/2010 | Foley et al. |
| 7,835,784 B2 | 11/2010 | Mire et al. |
| 7,862,568 B2 | 1/2011 | Vilsmeier et al. |
| 8,010,180 B2 | 8/2011 | Quaid et al. |
| 8,057,407 B2 | 11/2011 | Martinelli et al. |
| 8,357,165 B2 | 1/2013 | Grant et al. |
| 8,366,719 B2 | 2/2013 | Markey et al. |
| 8,706,285 B2 | 4/2014 | Narainasamy et al. |
| 8,834,527 B2 | 9/2014 | Hutton et al. |
| 9,008,757 B2 | 4/2015 | Wu |
| 9,050,108 B2 | 6/2015 | Grinberg et al. |
| 9,066,751 B2 | 6/2015 | Sasso |
| 9,161,793 B2 | 10/2015 | Huebner |
| 9,161,799 B2 | 10/2015 | Benson et al. |
| 9,168,151 B2 | 10/2015 | Sweeney et al. |
| 9,216,048 B2 | 12/2015 | Markey et al. |
| 9,480,916 B2 | 11/2016 | Miller et al. |
| 9,566,122 B2 | 2/2017 | Bowling et al. |
| 9,585,700 B2 | 3/2017 | Wehrle et al. |
| 9,687,306 B2 | 6/2017 | Markey et al. |
| 9,707,043 B2 | 7/2017 | Bozung |
| 9,795,319 B2 | 10/2017 | Lavallee et al. |
| 2006/0079903 A1 | 4/2006 | Wong |
| 2014/0236159 A1 | 8/2014 | Haider et al. |
| 2015/0031985 A1 | 1/2015 | Reddy et al. |
| 2015/0238206 A1 | 8/2015 | Benson et al. |
| 2016/0095631 A1 | 4/2016 | Stad |
| 2016/0166335 A1 | 6/2016 | Roger et al. |
| 2018/0289429 A1 | 10/2018 | Roger et al. |
| 2018/0303522 A1* | 10/2018 | Wall .............. A61B 17/7032 |
| 2018/0325608 A1 | 11/2018 | Kang et al. |
| 2019/0029736 A1 | 1/2019 | Wall et al. |
| 2019/0029737 A1 | 1/2019 | Wall et al. |
| 2019/0090966 A1 | 3/2019 | Kang et al. |
| 2019/0269469 A1 | 9/2019 | Bush, Jr. et al. |
| 2020/0085500 A1 | 3/2020 | Dace et al. |

* cited by examiner

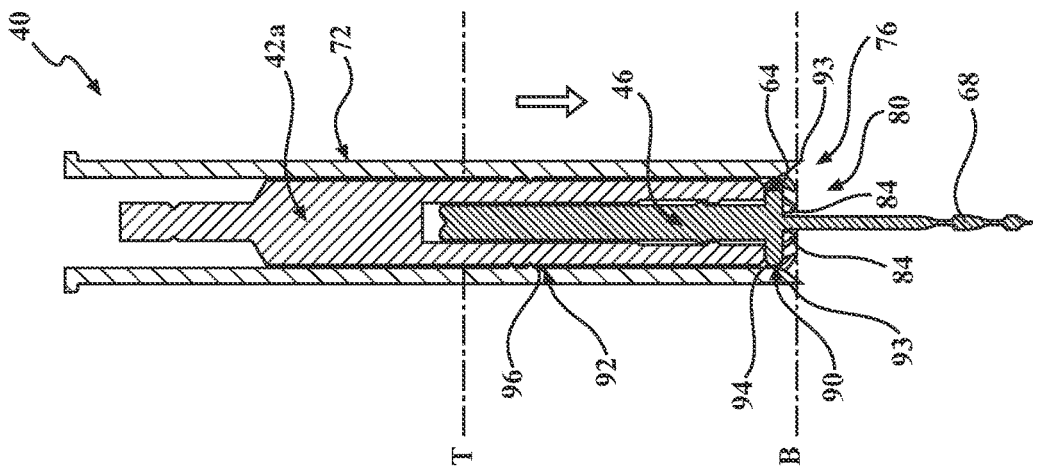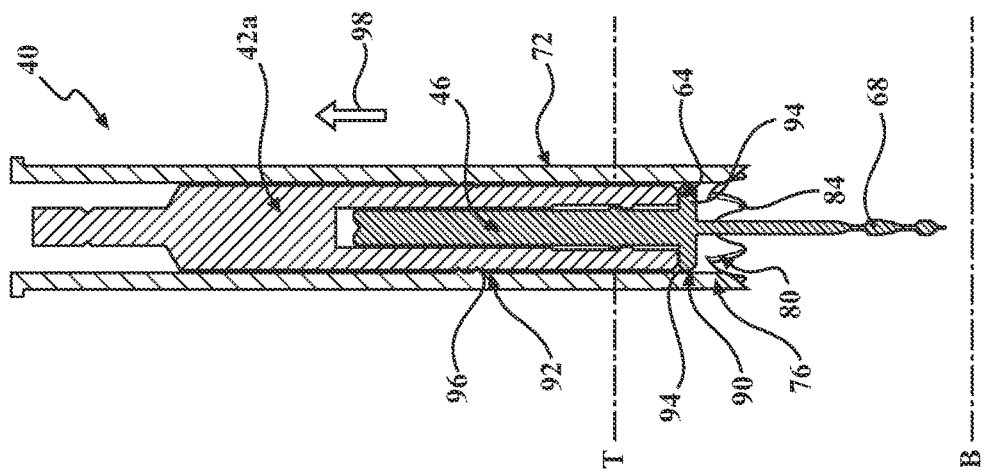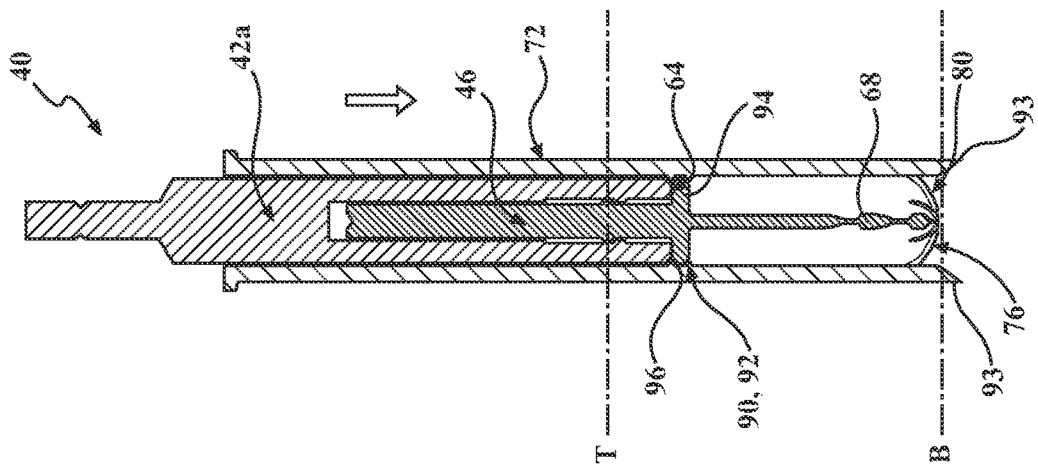

TOOL ASSEMBLY, SYSTEMS, AND METHODS FOR MANIPULATING TISSUE

CROSS REFERENCE TO RELATED APPLICATIONS

This application is a continuation of U.S. Nonprovisional patent application Ser. No. 16/290,177, filed Mar. 1, 2019, which claims priority to and all the benefits of U.S. Provisional Patent App. No. 62/637,472, filed Mar. 2, 2018, the entire contents of each of the aforementioned applications being hereby incorporated by reference.

TECHNICAL FIELD

The present disclosure is generally directed to devices, systems, and methods for surgical procedures, and more specifically, but not exclusively, robotic-assisted and/or navigation-assisted surgical procedures involving placement of an implant within a pedicle of a vertebra.

BACKGROUND

Surgical procedures include precise placement of implants within bony anatomy underlying soft tissue. One relevant example is the placement of a screw within a pedicle of a vertebra during a spinal fusion procedure, in which the screw is placed in a desired position and orientation. Ensuring proper pose (i.e., position and orientation) of the screw is challenging when the procedure is minimally invasive. Known techniques include a Kirschner wire (K-wire) manually placed through the skin and into the vertebra to establish the desired orientation. The screw is cannulated and inserted over the K-wire to the desired position. However, because K-wires are relatively flexible and may bend or break, and because the screw can deviate from the desired orientation in such instances, the accuracy of this technique relies largely on the expertise of the surgeon. In more recent surgical systems using robotic assistance, hand operated tools are employed to drill a pilot hole and/or place the screw with a robot controlling alignment of the tools. However, most current robotic approaches do not facilitate robot-assisted advancement of the tools or implants within the bone.

Several steps are necessary to implant the screw within the pedicle with many of the steps requiring distinct instrumentation. For example, a scalpel may be required to provide an incision within the overlying soft tissue, a drill may be used to prepare a pilot hole, a screwdriver may be required to advance the screw, and the like. Each of the instruments, or working tools, are not necessarily compatible with the interface of current robotic surgical systems. The time and effort expended during the surgical procedure to move between working tools is undesirable, and retrofitting current robotic surgical systems may be particularly expensive and complicated.

Many spinal fusion procedures include a discectomy where at least a portion of an intervertebral disc is removed, after which an intervertebral cage (i.e., an artificial disc) is placed. The discectomy and cage placement is often associated with relative movement between adjacent vertebrae. As a result, if navigation systems are employed to track the adjacent vertebrae, but unable to account for such relative movement, a tracked position of the vertebrae may incur error that is intolerable for subsequent robotic-assisted placement of the tools or the screw with respect to the vertebra.

Therefore, a need exists in the art for a tool assembly and systems for manipulating tissue and methods of manipulating tissue, particularly during navigation-assisted and/or robotic-assisted surgery, that overcome one or more of the aforementioned disadvantages.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a method is provided of operating a system for performing a surgical procedure on a vertebral body adjacent soft tissue, the system comprising a manipulator configured to move an end effector, a screw configured to be coupled to the end effector and a sleeve disposed coaxially around the screw and extending along an entire length of the screw, wherein the screw and the sleeve are releasably engaged to one another, a navigation system configured to track the vertebral body and including an insertion trajectory for the screw defined with respect to a surgical plan, and one or more controllers, the method comprising: controlling, with the one or more controllers, the manipulator for positioning the screw and the sleeve on the insertion trajectory; controlling, with the one or more controllers, the manipulator for advancing both the screw and the sleeve along the insertion trajectory to penetrate the soft tissue; and advancing the screw relative to the sleeve along the insertion trajectory for securing the screw to the vertebral body and for disengaging the screw from the sleeve during advancement.

According to a second aspect, a method is provided of operating a system for performing a surgical procedure on a vertebral body adjacent soft tissue, the system comprising a manipulator configured to move an end effector, a screw configured to be coupled to the end effector and a sleeve disposed coaxially around the screw, the screw and the sleeve being releasably engaged to one another, and the sleeve comprising a movable feature formed from flexible material at a distal end of the sleeve, a navigation system configured to track the vertebral body and including an insertion trajectory for the screw defined with respect to a surgical plan, and one or more controllers, the method comprising: controlling, with the one or more controllers, the manipulator for positioning the screw and the sleeve on the insertion trajectory; controlling, with the one or more controllers, the manipulator for advancing both the screw and the sleeve along the insertion trajectory within the soft tissue whereby the movable feature of the sleeve is in an initial configuration in which the distal end of the sleeve is substantially or completely closed for preventing ingress of the soft tissue within the sleeve during advancement; and advancing the screw along the insertion trajectory and through the distal end of the sleeve for securing the screw to the vertebral body, whereby advancing the screw through the distal end of the sleeve causes the movable feature to move from the initial configuration to a deployed configuration in which the flexible material deflects outwardly to open the distal end of the sleeve.

According to a third aspect, a method is provided of operating a system for performing a surgical procedure on a vertebral body adjacent soft tissue, the system comprising a manipulator configured to move an end effector, a screw comprising a proximal shaft portion configured to be coupled to the end effector and a distal working portion extending from the proximal shaft portion, a sleeve disposed coaxially around the screw and wherein the screw and the sleeve are releasably engaged to one another, a navigation system configured to track the vertebral body and including an insertion trajectory for the screw defined with respect to a surgical plan, wherein the navigation system comprises a localizer and a tracking device including markers configured to be detected by the localizer and the tracking device comprising a ratcheting mechanism, and one or more controllers, the method comprising: controlling, with the one or more controllers, the manipulator for positioning the screw and the sleeve on the insertion trajectory; controlling, with the one or more controllers, the manipulator for advancing both the screw and the sleeve along the insertion trajectory to penetrate the soft tissue; advancing the screw relative to the sleeve along the insertion trajectory for securing the distal working portion of the screw to the vertebral body and for disengaging the screw from the sleeve during advancement; coupling the tracking device to the proximal shaft portion of the screw; and utilizing the ratcheting mechanism of the tracking device for rotating the markers of the tracking device relative to the screw in a first rotational direction about a longitudinal axis of the screw.

BRIEF DESCRIPTION OF THE DRAWINGS

Advantages of the present disclosure will be readily appreciated as the same becomes better understood by reference to the following detailed description when considered in connection with the accompanying drawings.

FIG. 8A is the sectional view of the tool assembly of FIG. 7 positioned within tissue.

FIG. 8B is the sectional view of the tool assembly of FIG. 8A positioned within tissue with an altered relative axial position between an elongate sleeve and the working tool of the tool assembly.

FIG. 8C is the sectional view of the tool assembly of FIG. 8B positioned within the tissue with the working tool engaging underlying bone.

DETAILED DESCRIPTION

Figure 1:
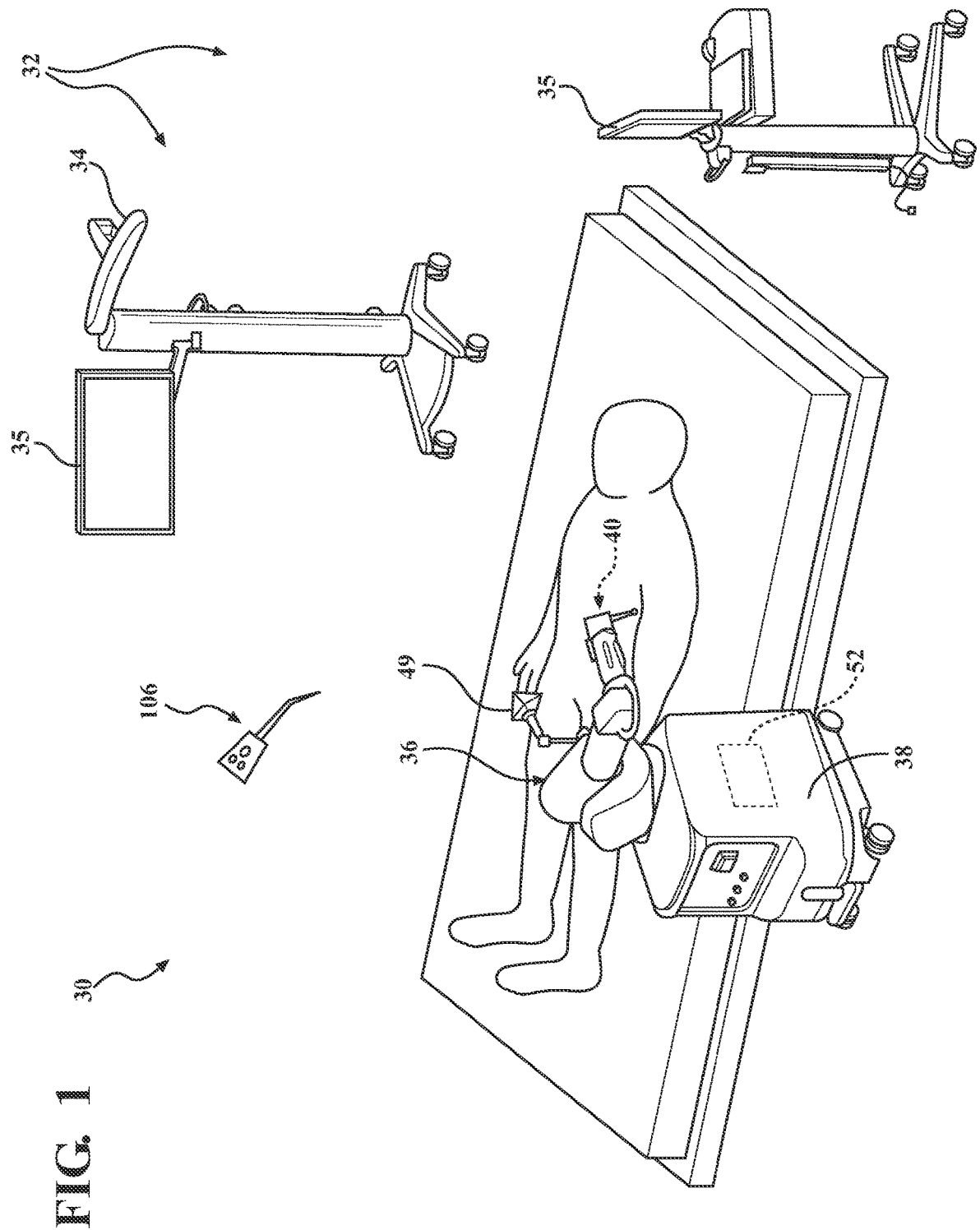
FIG. 1 is a perspective view of a robotic surgical system.
Figure 23:
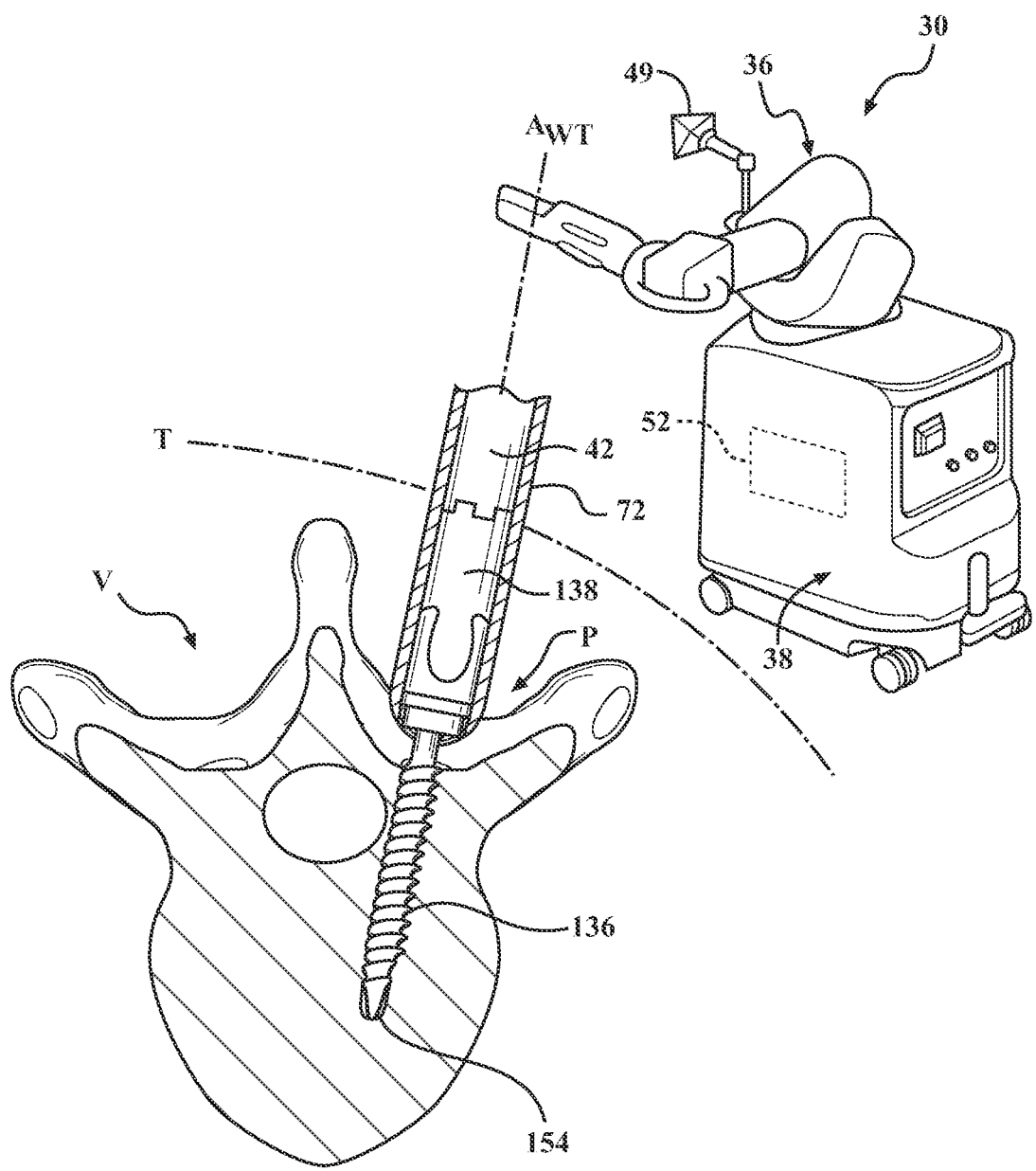
FIG. 23 is the schematic representation of the vertebra of FIG. 22 receiving the working tool of FIG. 18 guided with the robotic surgical system of FIG. 1.

FIG. 1 shows a robotic system 30 with a tool assembly 40 in accordance with exemplary embodiments of the present disclosure. The robotic system 30 and tool assembly 40 may be operated to surgically manipulate tissue of a patient. The robotic system 30 may be used with the tool assembly 40 for various methods and procedures in which the tissue (e.g., bony anatomy underlying or adjacent soft tissue or other tissue) is prepared for implantation of screws or for placement of other types of implants. Of particular interest is a spinal procedure in which the pedicle(s) of one or more vertebrae are prepared for implantation of a tap marker 100 (see FIG. 13) and pedicle screw 136 in the spine (see FIG. 23).

The robotic system 30 includes a navigation system 32 with a localizer 34, and a robotic manipulator (e.g., a robotic arm 36 mounted to a base 38). In one embodiment, the robotic manipulator is the Robotic Interactive Orthopedic (RIO™) System manufactured by MAKO Surgical Corp. (Fort Lauderdale, Fla.). The tool assembly 40 is represented schematically in FIG. 1 coupled to the robotic arm 36, as it is to be understood that the tool assembly 40 may assume any number of permutations to be described throughout the present disclosure. Further, in certain embodiments to be described, the tool assembly 40 may be operated as part of a handheld system supported by the surgeon in the absence of the robotic arm 36.

Figure 2:
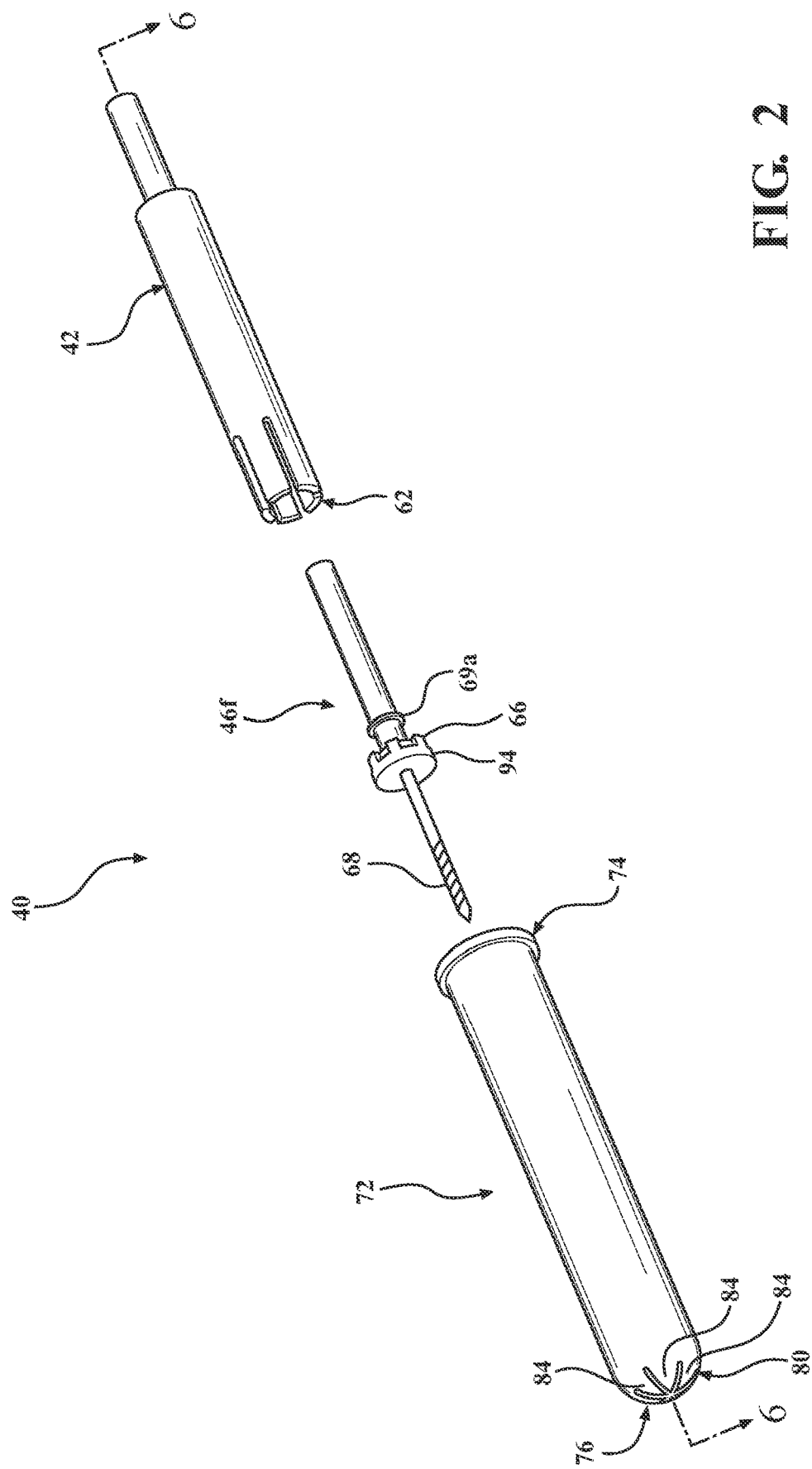
FIG. 2 is an exploded view of a tool assembly.
Figure 3:
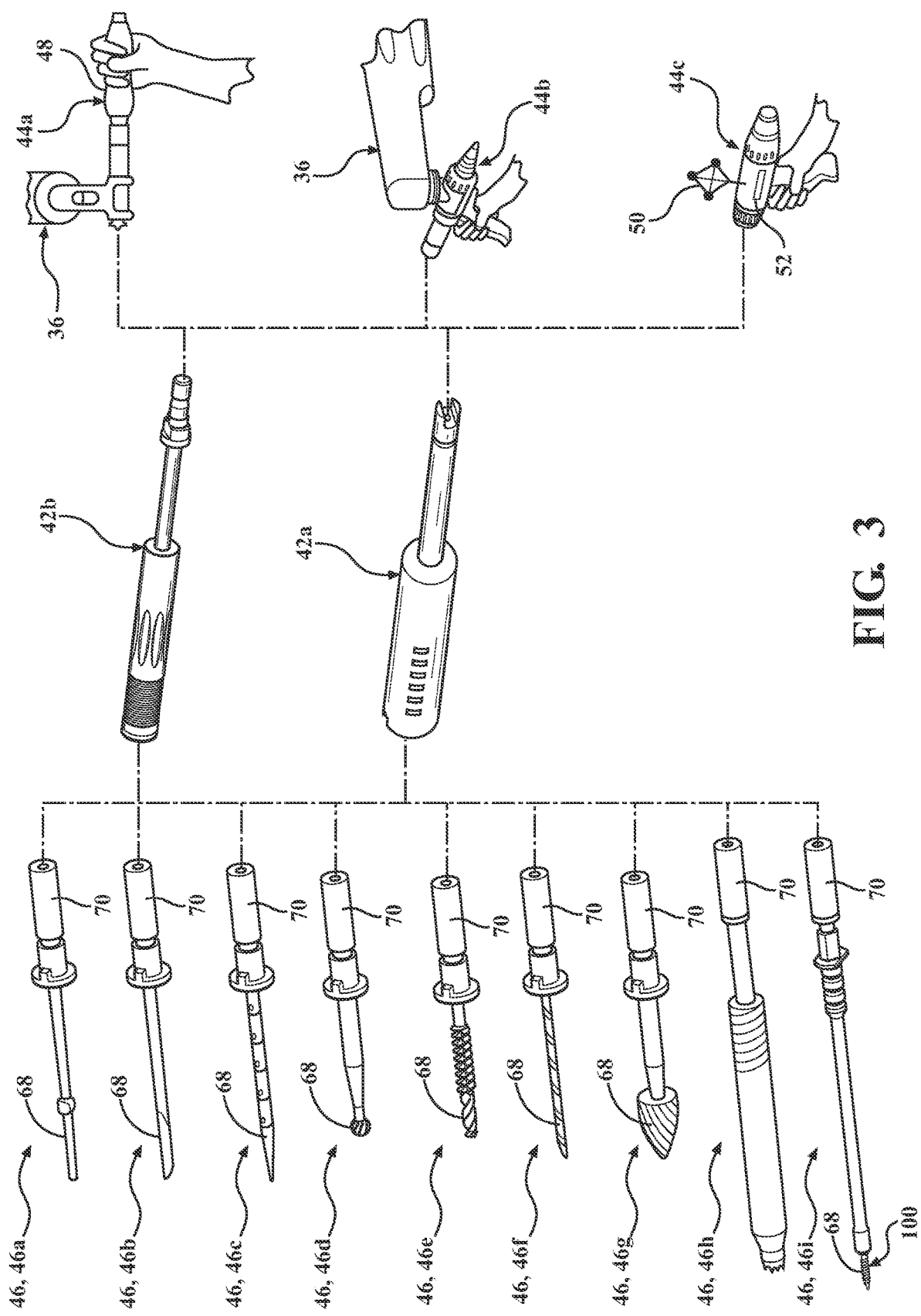
FIG. 3 is a schematic representation of several exemplary working tools to be coupled to drive couplers with the drive coupler to be coupled to one of several exemplary input devices.

Referring to FIG. 2, the tool assembly 40 includes a drive coupler 42. The drive coupler 42 is removably coupled to an input device 44, for example, a capital device associated with the robotic manipulator. In a broadest sense, the input device 44 provides a force to move the drive coupler 42. In many instances, the force is a torque to impart rotational movement to the drive coupler 42. Additionally or alternatively, the movement imparted by the input device 44 may be translational such that the input device 44 is capable of moving the drive coupler 42 in six degrees of freedom. FIG. 3 shows three examples of the input device 44 to which one of two drive couplers 42a, 42b may be removably coupled. The first illustrated example of the input device 44a includes a grip 48 or handle coupled to the robotic arm 36. The grip 48 is adapted to be manually manipulated by a surgeon, for example, to rotate the drive coupler 42a, 42b coupled thereto. The second illustrated example of the input device 44b is a powered device coupled to the robotic arm 36. The powered device includes a motor and an actuator (e.g., a trigger) for the surgeon to selectively actuate to rotate the drive coupler 42a, 42b coupled thereto. The third illustrated example of the input device 44c is arranged to be handled by the surgeon in a freehand manner (i.e., the input device 44c is not coupled to the robotic arm 36). The input device 44c is a powered device including a motor and an actuator (e.g., a trigger) for the surgeon to selectively actuate to rotate the drive coupler 42a, 42b coupled thereto. In certain embodiments, the input device 44a, 44b, 44c may include a tracking device 50 rigidly coupled thereto with the tracking device 50 detectable by the localizer 34 of the navigation system 32 in manners to be described.

A robotic controller 52 (FIG. 1) may be configured to control or constrain the tool assembly 40 as the surgeon manipulates the input device 44. In embodiments where the input device 44a, 44b is coupled to the robotic arm 36, the robotic controller 52 may be configured to control the robotic arm 36 with actuators (e.g., joint motors) to provide haptic feedback to the surgeon via the robotic arm 36. The haptic feedback helps to inhibit the surgeon from manually moving the tool assembly 40 beyond predefined virtual boundaries associated with the surgical procedure. One exemplary haptic feedback system with associated haptic objects defining virtual boundaries is described in U.S. Pat. No. 8,010,180, hereby incorporated by reference in its entirety. In embodiments where the input device 44c is operated in a freehand manner, the robotic controller 52 may be configured to control a working portion movably coupled to a hand-held portion in order to maintain a desired relationship between the working portion and the predefined virtual boundary. One exemplary freehand system is described in U.S. Pat. No. 9,707,043, which is hereby incorporated by reference herein in its entirety. It is further to be understood that the input device 44 may be operated by the surgeon without control, guidance, or other assistance.

Figure 4A:
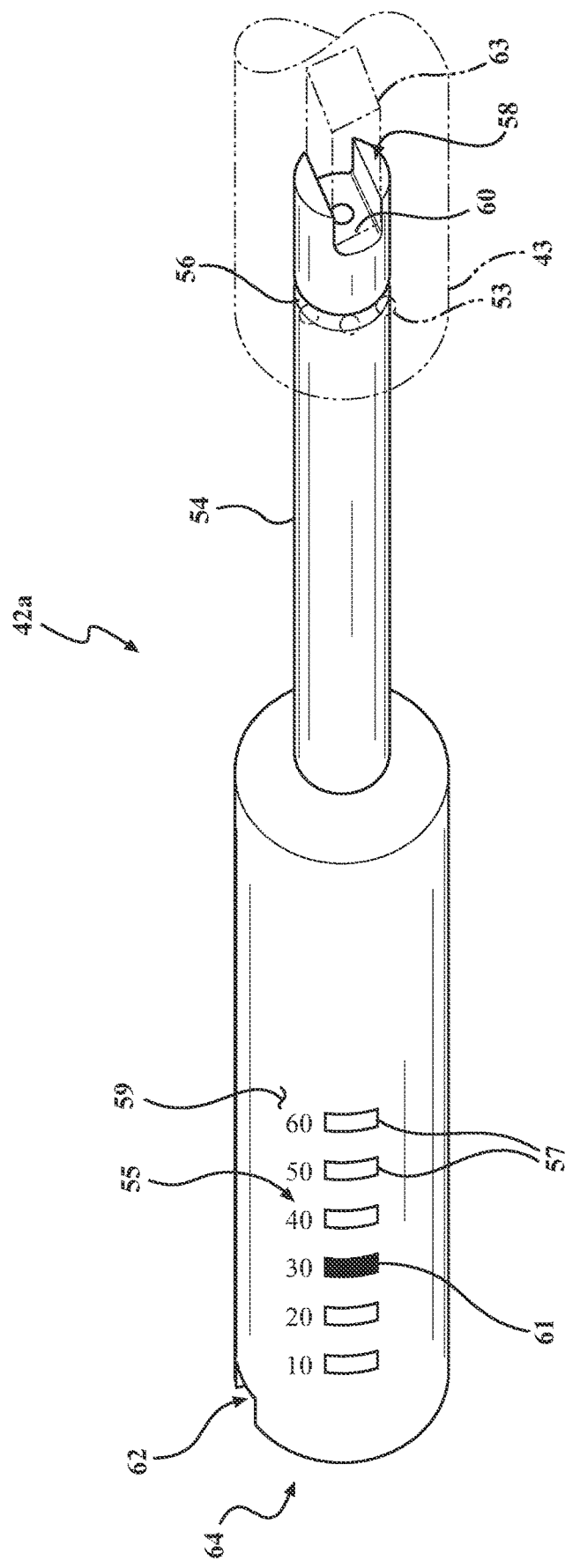
FIG. 4A is a perspective view of one of the drive couplers of FIG. 3.

Referring to FIG. 4A, the drive coupler 42a includes a proximal shaft 54. The proximal shaft 54 is coaxially coupled to a chuck 43 of the input device 44. To removably couple the drive coupler 42a to the input device 44, the proximal shaft 54 may include one or more retaining features 56, for example, a groove adapted to receive a biased protrusion 53 (e.g., a retainer ball as shown in hidden lines) of the input device 44 to form a detent mechanism. Further, at or near a coupler proximal end 58 of the proximal shaft 54, the drive coupler 42a includes a driven feature 60, for example, a slot or recess adapted to receive a drive feature 63 of the input device 44. Torque from the input device 44 is transferred to the drive coupler 42a at the interface of the driven feature 60 and drive feature 63. Other suitable constructions for transferring torque may be employed.

Figure 4B:
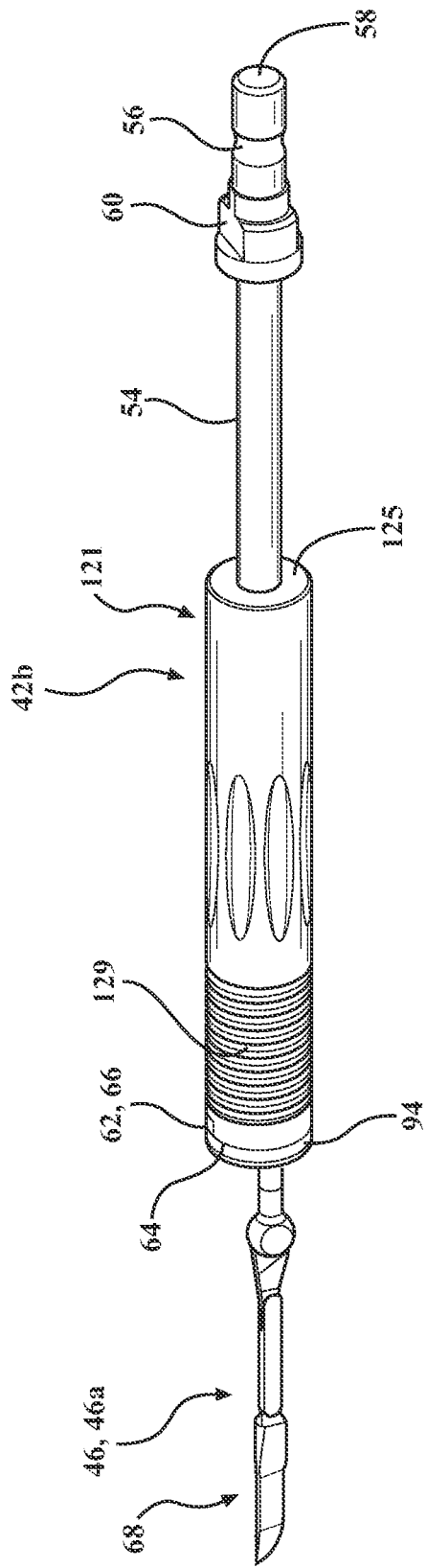
FIG. 4B is a perspective view of the other one of the drive couplers of FIG. 3.
Figure 6A:
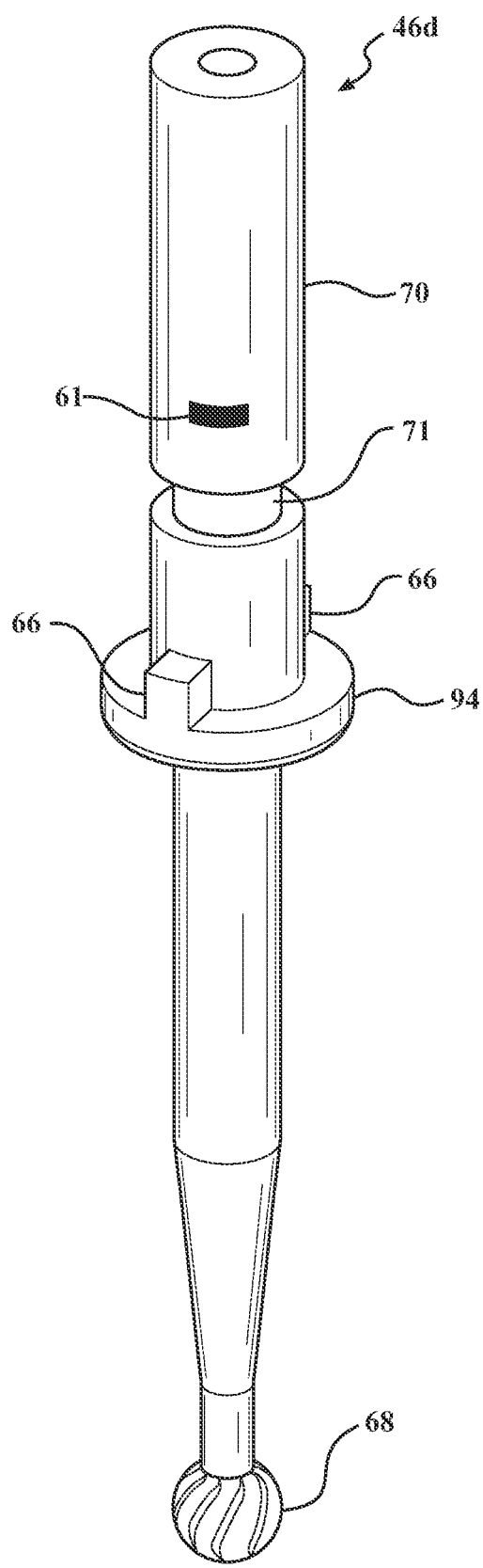
FIG. 6A is a perspective view of one of the working tools of FIG. 3 with mating features of the working tool adapted to provide bidirectional rotation of the working tool.
Figure 6B:
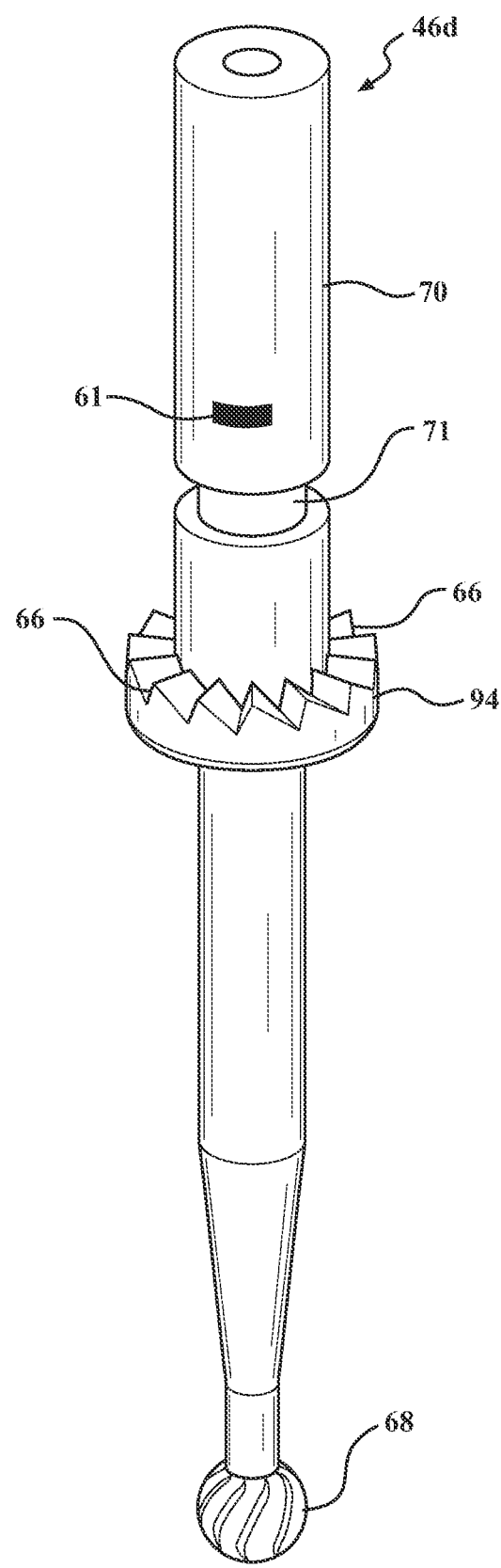
FIG. 6B is a perspective view of the working tool of FIG. 6A with mating features of the working tool adapted to provide unidirectional rotation of the working tool.

The drive coupler 42a facilitates sterile, efficient, and straightforward coupling and decoupling of a variety of working tools 46 without requiring decoupling of the drive coupler 42a from the input device 44. As best shown in FIGS. 2 and 4A, the drive coupler 42a includes mating features 62 at or near the coupler distal end 64 opposite the coupler proximal end 58. The mating features 62 releasably engage mating features 66 of the working tool 46 to be described (see FIGS. 6A and 6B). The complementary mating features 62, 66 rotationally fix the working tool 46 relative to the drive coupler 42a. Notably, different examples of the drive coupler 42a are shown in FIGS. 2, 4A and 4B. For example, the mating features 62 in of the drive coupler 42a of FIG. 2 include a plurality of tongues and slots arranged to receive one or more of the mating features 66 of the working tool 46. For another example, the mating features 62 in the embodiment illustrated in FIG. 4A include one or more notches arranged to receive one or more of the mating features 66 of the working tool 46. The interference between the complementary mating features 62, 66 transfers the torque from the drive coupler 42a to the working tool 46 in either a unidirectional or bidirectional manner. FIG. 6A shows the mating features 66 as generally cubic in form with opposing faces adapted to engage the mating features 62 of the drive coupler 42a regardless of direction in which the drive coupler 42a is rotated. FIG. 6B shows the mating features 66 appearing generally right-triangular in cross section such that the mating features 66 engage the mating features 62 of the drive coupler 42a when the drive coupler 42a is rotated in one direction but not the opposite direction (i.e., a slip mechanism).

Referring to FIG. 4A and FIGS. 6A and 6B, when the working tool 46 (working tool 46d shown) and the drive coupler 42a are coupled to one another, indicia 55 may indicate a length by which the working tool 46 extends beyond the drive coupler 42a. The length may be indicative of a depth of the working tool 46 within the tissue. With specific reference to FIG. 4A, the drive coupler 42a may include windows 57 within outer surface 59. The proximal shaft portion 70 of the working tool 46 may include a marking 61 (see FIGS. 6A and 6B) corresponding to a length of the working tool 46. In other words, a position of the marking 61 on the proximal shaft portion 70 of the working tool 46 corresponds to its length. The marking 61 on the proximal shaft portion 70 is further positioned to align with one of the windows 57 of the drive coupler 42a. When the working tool 46 and the drive coupler 42a are coupled to one another, the marking 61 is visible through one of the windows 57 associated with varying indicia 55 that indicate the length of the working tool 46 (illustrated in FIG. 4A). The marking 61 visible through one of the windows 57 is associated with a numerical value, such as "30 mm," as illustrated in FIG. 4A. The numerical values of the indicia 55 may be, for example, millimeters of length of the working tool 46 extending beyond the drive coupler 42a, not including the flange 94. Thus, should the working tool 46 be "fully" advanced within the tissue (i.e., until the flange 94 contacts the tissue), the depth of the working tool 46 within the tissue may be equal to the indicia 55 identified on the drive coupler 42a. Upon efficient decoupling of the working tool 46 and coupling of another one of the working tools 46 in manners to be described, indicia 55 indicative of the potential depth of the working tool 46 within the tissue can quickly be ascertained.

Figure 7:
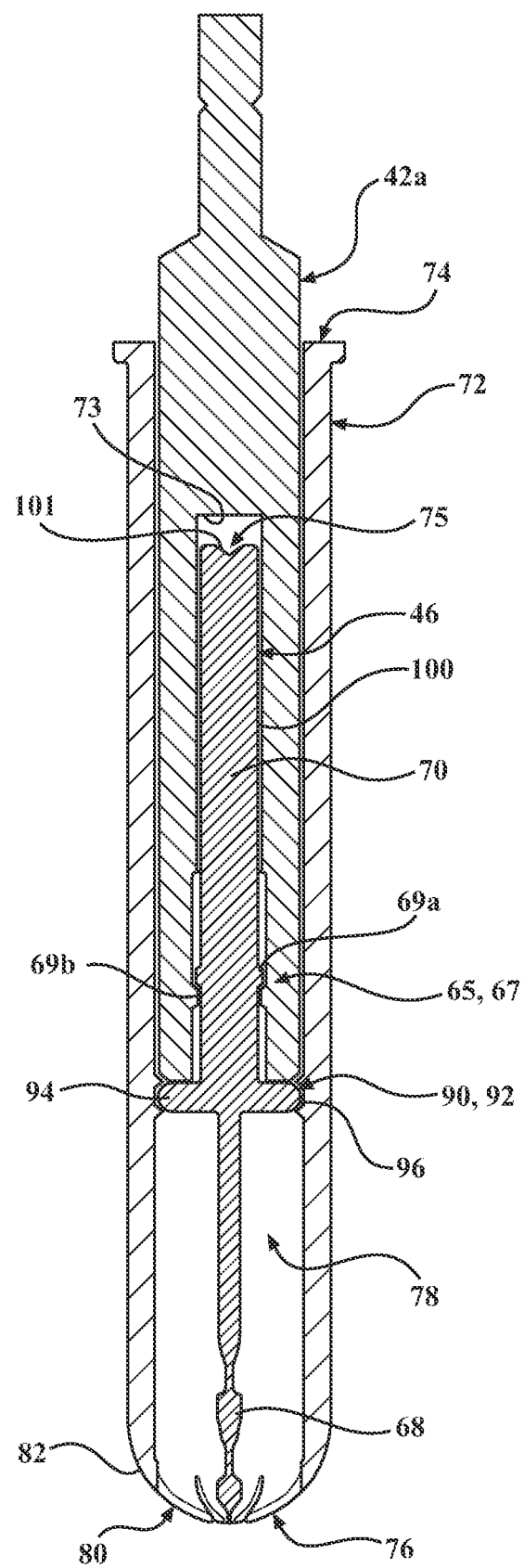
FIG. 7 is a cross sectional view of the tool assembly of FIG. 2 taken along section lines 6-6.

Referring to FIG. 7, the drive coupler 42a and the working tool 46 include complementary locking features 65, 67 adapted to be releasably engaged for releasably coupling the drive coupler 42a and the working tool 46. The complementary locking features 65, 67 selectively maintain an axial position of the working tool 46 relative to the drive coupler 42a when the drive coupler 42a and the working tool 46 are coupled to one another. FIG. 7 shows the working tool 46 and the drive coupler 42a each including a ring-shaped protrusion 69a, 69b (see also FIG. 2) forming the complementary locking features 65, 67 with the ring-shaped protrusions 69a, 69b maintaining the relative axial position with interference fit. In one variant, instead of interfering protrusions 69a, 69b, the working tool 46 may include a groove 71 (FIGS. 6A and 6B) adapted to receive a biased protrusion of the drive coupler 42a to form a detent mechanism.

The complementary locking features 65, 67 are adapted to disengage when subject to a sufficient axial force applied to the working tool 46 and/or the drive coupler 42a. For example, the tongues (shown in FIG. 2) of the drive coupler 42a may deflect slightly to permit the ring-shaped protrusion 69a of the working tool 46 to move past the ring-shaped protrusion 69b of the drive coupler 42a. In the example using the detent mechanism, the axial force applied to the working tool 46 and/or the drive coupler 42a is sufficient to overcome the biasing force provided to the protrusion to remain within the groove 71. Subsequent to disengagement of the complementary locking features 65, 67, the working tool 46 may be removed from a lumen 73 of the drive coupler 42a (see FIG. 7).

The complementary mating features 62, 66 and/or the complementary locking features 65, 67 are adapted to be releasably engaged when the working tool 46 is moved axially relative to the drive coupler 42a. In particular, the mating features 62 of the drive coupler 42a are at the coupler distal end 64 and generally open distally, whereas the mating features 66 of the working tool 46 are generally oriented proximally such that moving the working tool 46 distally relative to the drive coupler 42a disengages the complementary mating features 62, 66. With the drive coupler 42a coupled to the input device 44, the user may apply a distal axial force to the working tool 46 (e.g., "pull" the working tool 46 from the drive coupler 42a) to overcome the complementary mating features 62, 66 and/or the complementary locking features 65, 67, and move the working tool 46 distally relative to the drive coupler 42a, which may be coupled to the robotic arm 36. The working tool 46 is then removed from the lumen 73 of the drive coupler 42a. Once the working tool 46 is decoupled from the drive coupler 42a, another one of the working tools 46 may be coupled to the drive coupler 42a without significant manipulation or handling of the drive coupler 42a to facilitate efficient moving between a variety of working tools 46 during steps of the surgical procedure.

Referring to FIG. 3, several exemplary working tools 46 are shown with each adapted to interchangeably couple to the drive coupler 42a, 42b. Each of the working tools 46 includes a working section 68 opposite a proximal shaft portion 70 (see also FIGS. 2, 5A, 6B and 7). The proximal shaft portion 70 of the working tool 46 is removably coupled to the drive coupler 42a. The working section 68 is adapted to manipulate the tissue of the patient.

The working tool 46 may be a scalpel holder 46a. The scalpel holder 46a may include a coupling feature (not identified) adapted to removably receive the scalpel, lancet, or other knife-like device forming the working section 68 for incising or excising the tissue of the patient. Another one of the working tools 46 may be a scalpel, lancet, or other knife-like device 46b integral with the proximal shaft portion 70. Still another one of the working tools 46 may be a depth probe 46c including indicia along the working section 68. The working section 68 of the depth probe 46c is positionable within the tissue of the patient with the indicia providing the user with a depth of the working tool 46 within the patient. Movement of each of the aforementioned working tools 46 may be substantially translational. In other words, when one of the working tools 46a-46c is coupled to the drive coupler 42a, the input device 44 provides a force to impart translational movement to the working tool 46a-46c, and/or the tool assembly 40 is constrained to translational movement (e.g., with the robotic arm 36). For example, it may be appropriate to provide a linear or curvilinear incision to the patient with the scalpel 46b, and the robotic arm 36 may constrain the tool assembly 40 along the incision predefined on a surgical plan as the surgeon operates the tool assembly 40.

The working tools 46 may be adapted to receive a rotational input from the input device 44 via the drive coupler 42a. One of the working tools 46 may include a bur 46d with a bur head forming the working section 68. The rotating bur head is applied at a surgical site to resect the tissue of the patient. Another one of the working tools 46 is a tap drill 46e with the working section 68 formed of, for example, a twist drill bit and a tap for providing threads within the underlying bony anatomy of the patient. Still another one of the working tools 46 is a drill 46f with a drill bit of any desired characteristics forming the working section 68. Still yet another one of the working tools 46 is a dilator probe 46g with a widening working section adapted to expand an incision within the tissue as the dilator probe 46g is advanced. In manners to be described, the dilator probe 46g may be rotated unidirectionally and/or bidirectionally with oscillation to dilate the tissue. The working tool 46 may also include a dilation device 46h (see FIG. 10) in which an elongate sleeve 160 receives a dilator probe 162 or another one of the working tools 46 in a manner to be described.

The working tool 46 may also include a tap inserter 46i with a tap marker 100 (see FIG. 19) removably coupled to the tap inserter 46i and forming the working section 68. The tap inserter 46i is rotated to implant the tap marker 100 within the bony anatomy, such as within the pedicle of the vertebra. It is contemplated that any number of additional working tools 46 may be included as a modular component of the tool assembly 40.

Each of the illustrated examples of the working tools 46 include the same or similar mating features 66 (e.g., the cubic-shaped protrusions oriented distally) and the same or similar locking features 65 (e.g., ring 69a or circumferential groove 71). Thus, during the surgical procedure, particularly as the drive coupler 42a is coupled to the input device 44, the working tools 46 may be interchanged. The interchangeability of the working tools 46 improves adaptability of the surgical system and may provide a larger catalogue of working tools that can be coupled to the input device 44, which may be capital equipment not otherwise compatible with certain working tools. Thus, the drive coupler 42a, in some cases, can operate as an adapter to interchangeably connect various types of working tools 46 that carry out various functions for a single surgical procedure.

Referring now to FIGS. 4B and 5A-5C, the drive coupler 42b may be configured to provide for at least translational movement of the working tool 46 relative to the input device 44 to which the drive coupler 42b is coupled. More particularly, the drive coupler 42b may be configured to provide for translational and/or rotational movement of the working tool 46 relative to the input device 44 about an axis of the working tool 46 as the manipulator otherwise constrains lateral movement of the working tool 46. The translational and/or rotational movement may be facilitated through a manual input of a user. Stated differently, the drive coupler 42b may be configured to provide for manual manipulation in at least two degrees of freedom as the manipulator constrains movement of the working tool 46 in the remaining four degrees of freedom. In manners to be further explained, such an arrangement may be particularly useful to with the scalpel attachment 46a and the dilator probe attachment 46c to provide for semimanual incising and dilating, respectively, of the soft tissue with constraint from the manipulator.

The drive coupler 42b includes the proximal shaft portion 54 to be coaxially coupled to the chuck 43 of the input device 44, for example, with the retaining features 56. Further, at or near a coupler proximal end 58 of the proximal shaft 54, the drive coupler 42b includes a driven feature 60, for example, a flat adapted to receive a drive feature 63 of the input device 44. Torque from the input device 44 is transferred to the drive coupler 42a at the interface of the driven feature 60 and drive feature 63.

Figure 5A:
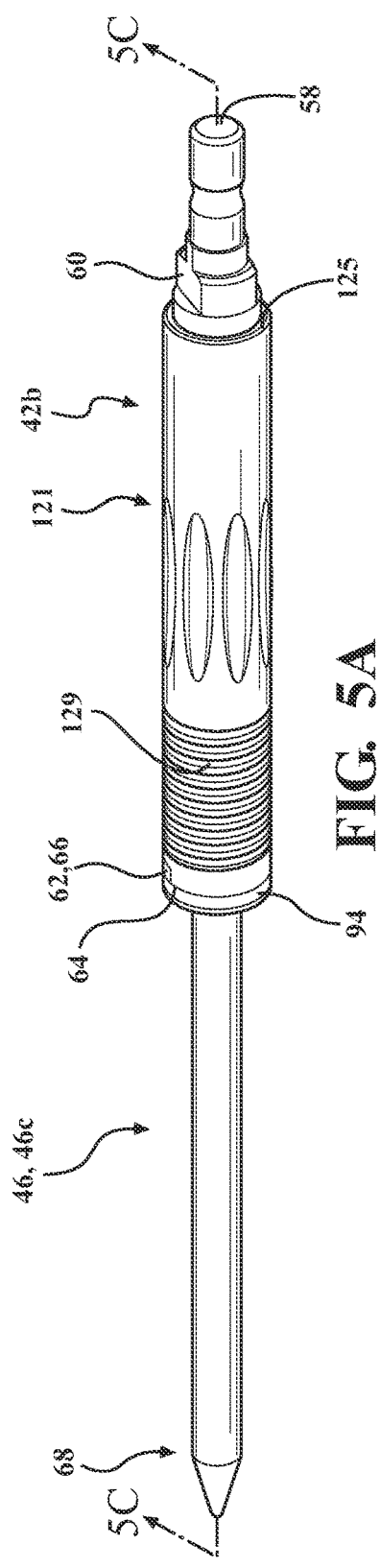
FIG. 5A is a perspective view of the drive coupler of FIG. 4B in a first position.
Figure 5B:
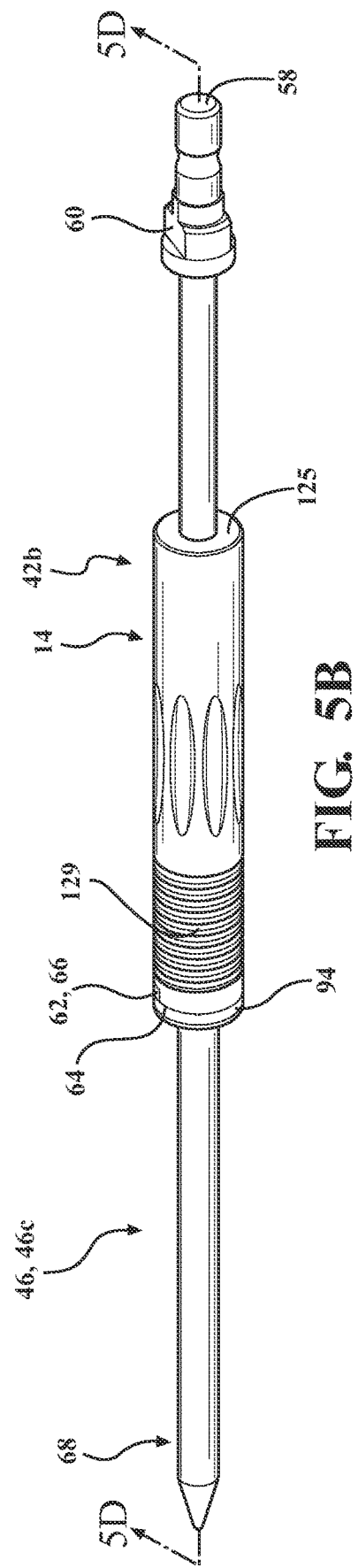
FIG. 5B is a perspective view of the drive coupler of FIG. 4B in a second position.

The drive coupler 42b includes a distal housing 121 movably coupled to the proximal shaft portion 54. In particular, the distal housing 121 defines a bore 123 at least partially extending between a proximal end 125 opposite the coupler distal end 64. The bore 123 is sized to slidably receive the proximal shaft portion 54 of the drive coupler 42b. Further, the bore 123 may be configured to receive the proximal shaft portion 70 of the working tool 46. FIGS. 4B, 5A and 5B show the flange 94 of the working tool 46 in abutment with the coupler distal end 64 of the drive coupler 42b. The drive coupler 42b includes the mating features 62 at or near the coupler distal end 64 to releasably engage mating features 66 of the working tool 46 when the proximal shaft portion 70 is disposed within the bore 123 and the flange 94 engages the drive coupler 42b. The complementary mating features 62, 66 rotationally fix the working tool 46 relative to the drive coupler 42a. Thus, other than decoupling of the working tool 46 from the drive coupler 42b, the working tool 46 may be positionally fixed relative to the drive coupler 42b.

With the proximal shaft portion 54 coupled to the input device 44 and the distal housing portion 121 movable relative to the proximal shaft portion 54, a user may provide an input to the distal housing portion 121 to translate the working tool 46 relative to the input device 44. The distal housing portion 121 may include a control surface 129, for example a grip, configured to receive an input from the user. The input from the user may move the drive coupler 42b between a first positon shown in FIGS. 5A and 5C, and a second position shown in FIGS. 5B and 5D. Relative to the proximal end 58 of the drive coupler 42b as a datum, the distal working section 68 of the working tool 46 is at a first distance in the first position, and at a second distance greater than the first distance in the second position. In other words, providing an input to the control surface 129 with the drive coupler 42b in the first position (e.g., a force to the left) translates the working tool 46 away from the input device 44, and often towards the patient. Conversely, providing another input to the surface 129 with the drive coupler 42b in the second position (e.g., a force to the left) translates the working tool 46 away from the input device 44, often away from the patient.

Figure 5C:
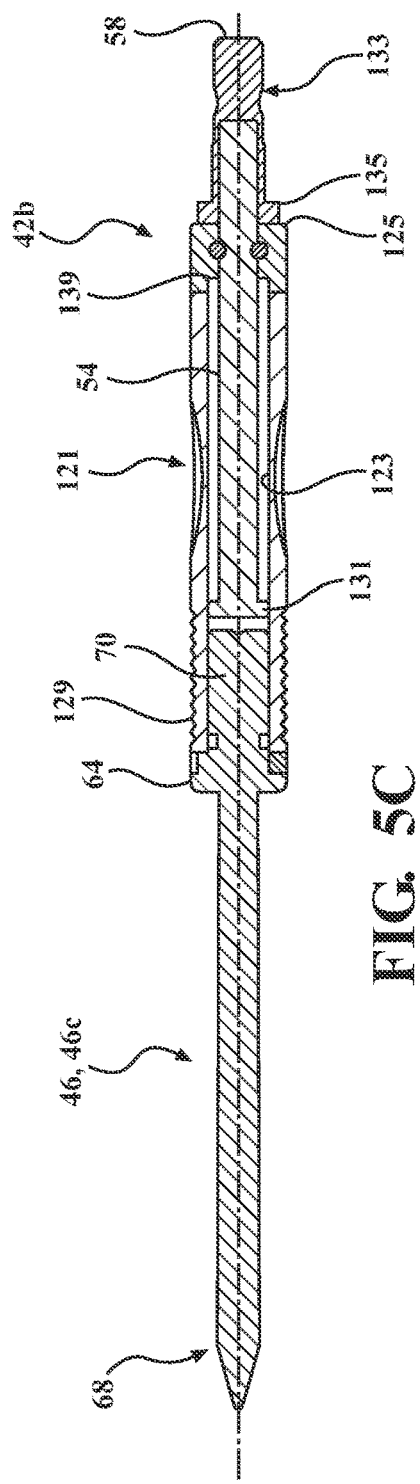
FIG. 5C is a sectional view of the drive coupler of FIG. 5A taken along section lines 5C-5C.
Figure 5D:
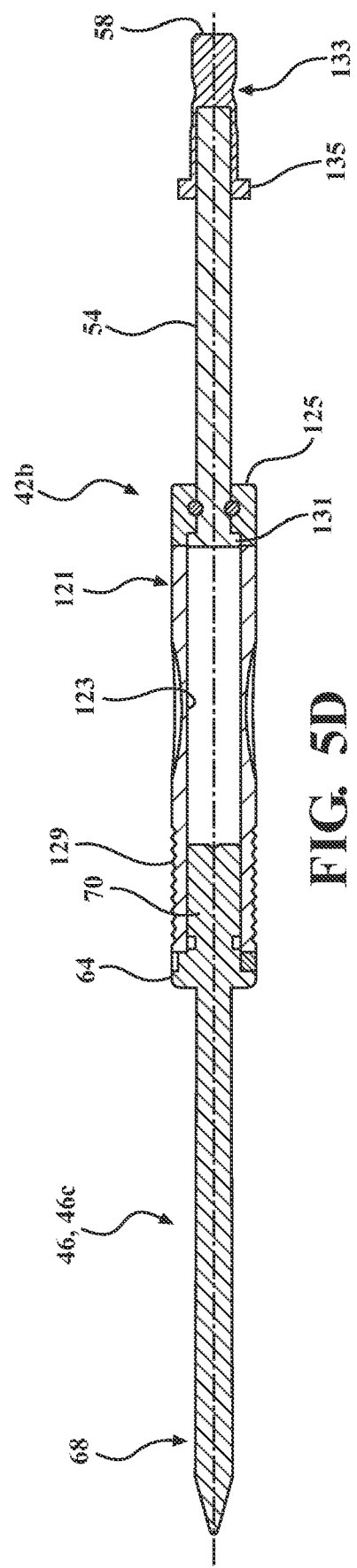
FIG. 5D is a sectional view of the drive coupler of FIG. 5B taken along section lines 5D-5D.

With continued reference to FIG. 5C showing the drive coupler 42b in the first position, nearly an entirety of the proximal shaft portion 54 of the drive coupler 42b is disposed within the bore 123 of the distal housing portion 121. A piston 131 at the end of the proximal shaft portion 54 is positioned adjacent the proximal shaft portion 70 of the working tool 46. A collet 133 includes a flange 135 engages the proximal end 125 of the distal housing portion 123 such that the proximal shaft portion 54 is preventing from moving further into the bore 123. With reference to FIG. 5D showing the drive coupler 42b in the second position, the piston 131 is disposed within the bore 123 with most of the proximal shaft portion 54 external to the distal housing portion 121. The piston 131 engages a stop surface 139 defined by the distal housing portion 121 such that the proximal shaft portion 54 is distal housing portion 121 is prevented from further distal movement.

A workflow in which the manipulator is the robotic arm 36 and the input device 44 is an end effector coupled to the manipulator will now be described. Prior to the start of the surgical procedure, an insertion trajectory is defined for the navigation system 32, and then the plan is transferred to the robotic system 30 for execution. The robotic system 30 evaluates the insertion trajectory and creates virtual boundaries (e.g., haptic objects). The insertion trajectory may be a line haptic object to be described (see also FIG. 22).

The user couples the drive coupler 42b to the end effector, and couples the scalpel attachment 46a to the drive coupler 42b (see, e.g., FIG. 4B). It is also appreciated that coupling the scalpel attachment 46a to the end effector may also include coupling the scalpel attachment 46a to one of another working tool 46, the drill 166, the screwdriver 138, and the elongate sleeve 72, among others. The user manually manipulates (e.g., moves or causes the movement of) the end effector or the robotic arm 36 to position the scalpel attachment 46a above the overlying skin on the insertion trajectory. The robotic arm 36 and provides haptic feedback (e.g., force feedback) to the user to limit the user's ability to move (or cause movement of) the scalpel attachment 46a beyond one or more predefined virtual boundaries.

With the scalpel attachment 46a and the drive coupler 42b on the insertion trajectory, the user provides an input to the control surface 129 of the drive coupler 42b to move the drive coupler 42b from the first position to the second position; i.e., towards the patient. The robotic system 30 may effectively hold the scalpel attachment on the insertion trajectory (e.g., via a line haptic object) by tracking movement of the patient and autonomously adjusting the robotic arm 36 as needed. An incision is made within the overlying tissue, for example, with a plunge like movement. Further, with rotational movement of the distal housing portion 121 relative to the proximal shaft portion 54, further input to the control surface 129 provides for a stab incision in an 'X' or cross formation. Thus, the drive coupler 42b provides for semimanual incision in which feel and control are afforded to the user while ensuring the incision remains on the insertion trajectory. Moreover, engagement of the flange 135 with the proximal end 125 of the distal housing portion 121 provides a mechanical depth stop should the incision depth be controlled by a position of the end effector above the overlying skin.

The user may then move the drive coupler 42b from the second position to the first position such that the scalpel attachment 46a is above the overlying soft tissue. In manners previously explained, the scalpel attachment 46a may be decoupled from the drive coupler 42b, and the dilator probe attachment 46c may be coupled to drive coupler 42b without decoupling the drive coupler 42b from the end effector. It is also appreciated that coupling the dilator probe attachment 46c to the end effector may also include coupling the dilator probe attachment 46c to one of another working tool 46, the drill 166, the screwdriver 138, and the elongate sleeve 72, among others. With the dilator probe attachment 46c and the drive coupler 42b on the insertion trajectory, the user provides an input to the control surface 129 of the drive coupler 42b to move the drive coupler 42b from the first position to the second position; i.e., towards the patient. The robotic system 30 may effectively hold the dilator probe attachment 46c on the desired trajectory (e.g., via a line haptic object) by tracking movement of the patient and autonomously adjusting the robotic arm 36 as needed. The dilator probe attachment 46c is advanced within the incision and through the overlying tissue T to expand the incision. The dilator probe attachment 46c is constrained by the robotic arm 36 to the insertion trajectory. Further, with rotational movement of the distal housing portion 121 relative to the proximal shaft portion 54, further input to the control surface 129 provides for oscillation with dilation of the soft tissue. Thus, the distal coupler 42b provides for semimanual dilation in which feel and control are afforded to the user while ensuring the dilation remains on the insertion trajectory. Moreover, engagement of the flange 135 with the proximal end 125 of the distal housing portion 121 provides a mechanical depth stop should the dilation depth be controlled by a position of the end effector above the overlying soft tissue. The user may then move the drive coupler 42b from the second position to the first position, and decouple the dilator probe attachment 46c from the drive coupler 42b. The user may then decouple the drive coupler 42b from the end effector, and couple another drive coupler 42a to the end effector for one or more remaining steps of the workflow to be described.

It is readily appreciated that in minimally invasive surgical procedures, a working channel is often provided within the overlying tissue to facilitate improved access to the surgical site. Known systems and methods often require sequentially advancing tubular dilators of slightly increasing diameter with the last-placed dilator remaining within the overlying tissue for a portion of the surgical procedure. In the absence of using the dilator or a retractor, the overlying tissue may obstruct visibility of the surgeon and interfere with advancement of instruments that often include cutting features. Such instruments (e.g., anchors, etc.) may otherwise become undesirably entangled within the tissue when being placed within the underlying bone, such as when rotating an anchor into position. The tool assembly 40 of the present disclosure advantageously provides suitable retraction of the overlying tissue.

Referring to FIGS. 2 and 7, the tool assembly 40 includes an elongate sleeve 72 positionable within the tissue of the patient. When positioned within the tissue, the elongate sleeve 72 retracts the tissue to provide a working channel for the working tool 46. The elongate sleeve 72 includes a proximal end 74 opposite a distal end 76, and a cavity 78 disposed between the proximal and distal ends 74, 76. The sectional view of FIG. 7 shows the cavity 78 extending substantially an entire length of the elongate sleeve 72 between the proximal and distal ends 74, 76. In other permutations, the cavity 78 may extend for only a portion of the length of the elongate sleeve 72. The cavity 78 is sized and shaped to receive the working tool 46. For example, FIGS. 2 and 7 show the elongate sleeve 72 as a substantially tubular structure with the cavity 78 being substantially cylindrical in shape. The working tool 46 has a generally cylindrical shape with an outer diameter no greater than an inner diameter of the elongate sleeve 72. In certain embodiments, the working tool 46 and elongate sleeve 72 are dimensioned such that the working tool 46 is snugly and slidably received within the cavity 78 of the elongate sleeve 72. The elongate sleeve 72 is formed from material with suitable stiffness to maintain patency of the cavity 78 when the elongate sleeve 72 is positioned within the tissue. In one example, the elongate sleeve 72 is formed from polymeric material with the elongate sleeve 72 comprising a disposable component of the tool assembly 40.

The working tool 46, and in certain embodiments at least a portion of the drive coupler 42a, is positioned within the cavity 78 of the elongate sleeve 72 during use. With continued reference to FIG. 7, an entirety of the working tool 46 is within the cavity 78 and coupled to the drive coupler 42a with a portion of the drive coupler 42a extending within the elongate sleeve 72. The elongate sleeve 72 is coupled to one of the working tool 46 and the drive coupler 42a such that the tool assembly 40 may be moved and supported as a singular or integral kit or unit. In other words, tool assembly 40 may be supported at the coupler proximal end 58 of the drive coupler 42a coupled to the input device 44. The elongate sleeve 72 does not need to be separately supported, but may be in some cases. As a result, with one hand of the surgeon operating the input device 44, the other hand of the surgeon is free to perform other aspects of the surgical procedure.

To facilitate coupling the elongate sleeve 72 to the working tool 46, in certain embodiments, the working tool 46 and the elongate sleeve 72 include complementary locating features 90, 92 adapted to be releasably engaged to one another. The complementary locating features 90, 92 initially maintain an axial position of the working tool 46 relative to the elongate sleeve 72. More specifically, the axial position of the working tool 46 relative to the elongate sleeve 72 is maintained with engagement of the complementary locating features 90, 92 in the absence of an axial force applied to the working tool 46 and/or the elongate sleeve 72. In a manner to be described, an axial force applied to the working tool 46 and/or the elongate sleeve 72 results in disengagement of the complementary locating features 90, 92, thereby permitting movement (i.e., a change in the axial position) of the working tool 46 relative to the elongate sleeve 72.

The locating feature 90 of the working tool 46 may include a flange 94. With concurrent reference to FIGS. 2 and 7, the flange 94 is disposed between the working section 68 and the proximal shaft portion 70 of the working tool 46. The flange 94 extends radially outwardly from a longitudinal axis of the working tool 46 to define a generally disc-shaped flange. The locating feature 92 of the elongate sleeve 72 includes a groove 96. The groove 96 may extend annularly along an inner surface of the elongate sleeve 72 within the cavity 78. The groove 96 is adapted to receive and engage the flange 94 by, for example, friction fit or interference fit. The groove 96 is dimensioned such that if the tool assembly 40 is subjected to axial forces during the insertion of the elongate sleeve 72 within the tissue, the complementary locating features 90, 92 remain engaged to maintain the axial position of the working tool 46 relative to the elongate sleeve 72. Once indicated during the surgical procedure, the application of the axial force to the working tool 46 and/or the elongate sleeve 72 results in the flange 94 disengaging from within the groove 96, thereby permitting the working tool 46 to slidably move within the elongate sleeve 72. FIG. 7 shows the flange 94 positioned within the groove 96. It is to be understood that the complementary locating features 90, 92 may be arranged in reverse such that the flange is associated with the elongate sleeve 72 and the groove with the working tool 46.

The mating features 66 of the working tool 46 may be coupled to or integral with the flange 94. As shown in FIGS. 6A and 6B, the mating features 66 (e.g., the cubic-shaped or triangular-shaped "teeth") extend proximally from the flange 94. With the mating features 66 oriented proximally, the proximal shaft portion 70 of the working tool 46 may be positioned within the lumen 73 of the drive coupler 42a.

The elongate sleeve 72 includes a movable feature 80 adapted to enable opening of the distal end 76 of the elongate sleeve 72. Opening of the distal end 76 permits distal movement of the working tool 46 relative to the elongate sleeve 72, and in particular distal movement of the working tool 46 beyond the distal end 76 of the elongate sleeve 72. Referring to FIG. 7, the distal end 76 of the elongate sleeve 72 may comprise a taper 82 forming the movable feature 80. The taper 82 is shaped to prevent ingress of the tissue within the cavity 78 of the elongate sleeve 72 as the elongate sleeve 72 is positioned within the tissue. The taper 82 is shown as having a hemispherical or otherwise blunt shape, but the taper 82 may also comprise a conical shape and extend to a sharp tip.

The movable feature 80 moves between an initial configuration and a deployed configuration. In the initial configuration, the movable feature 80 includes the taper 82 that is shaped such that the distal end 76 of the elongate sleeve 72 is substantially or completely closed. The movable feature 80 may be in the initial configuration before the elongate sleeve 72 is positioned within the tissue. The movable feature 80 may also remain in the initial configuration after the elongate sleeve 72 is positioned within the tissue yet before the working section 68 of the working tool 46 is moved beyond the distal end 76 of the elongate sleeve 72. In one example illustrated in FIG. 2, the elongate sleeve 72 includes a plurality of tabs 84 forming the movable feature 80. The tabs 84 may be formed from suitably flexible material to deflect outwardly. The deflection may be facilitated with a living hinge. FIG. 2 shows each of the tabs 84 being arcuate in shape and circumferentially spaced about a central axis of the elongate sleeve 72 such that the tabs 84 cooperatively define a substantially hemispherical taper. The tabs 84 deflect outwardly in response to the working section 68 of the working tool 46 being moved distally beyond the distal end of the elongate sleeve 72.

Frangible material may interconnect the tabs 84 to seal the tabs 84 together and provide rigidity to the movable feature 80 as the elongated sleeve 72 is advanced distally within the tissue. The frangible material may be areas of thinner material relative to the tabs 84 such that the frangible material ruptures to permit the tabs 84 to deflect outwardly in response to the working section 68 of the working tool 46 being moved distally beyond the distal end 76 of the elongate sleeve 72. In other words, the movable feature 80 with the frangible material may be of suitable construction to maintain closure of the distal end 76 of the elongated sleeve 72 (i.e., prevent inward deflection) as the elongated sleeve 72 is advanced distally within the tissue, but prevent outward deflection in response to suitable distal force from the working section 68 of the working tool. In one example, the frangible material may be akin to flash from an injection molding process with each "piece" of flash disposed between adjacent tabs 84. With or without the frangible material interconnecting the tabs 84, in certain embodiments the distal end 76 is substantially or entirely closed prior to the movable feature 80 enabling opening of the distal end 76. In such an embodiment, the working section 68 of the working tool 46 is positioned proximal to the closed distal end 76 prior to the movable feature 80 enabling opening of the distal end, and prior to the working section 68 of the working tool 46 being moved distally beyond the distal end 76 of the elongate sleeve 72.

An exemplary operation of the tool assembly 40 is made with references to FIGS. 7 and 8A-8C with the tool assembly 40 coupled to the input device 44 (see FIG. 3). FIG. 7 shows the tool assembly 40 in an initial arrangement for coupling to the input device 44. The working tool 46 may be dimensioned such that, when the complementary locating features 90, 92 are engaged, the working section 68 of the working tool 46 is positioned within the cavity proximal to the movable feature 80 of the elongate sleeve 72. In another exemplary embodiment, a tip of the working section 68 may extend slightly beyond the distal end 76 of the elongate sleeve 72 so as to assist with advancing the tool assembly 40 within the tissue. In the initial configuration shown in FIG. 7, the complementary locating features 90, 92 are engaged, and the movable feature 80 is in the initial configuration. In other words, taper 82 is arranged such that the distal end 76 of the elongate sleeve 72 is substantially or completely closed. In one example, the tabs 84 are arranged inwardly radially. Furthermore, with the complementary locating features 90, 92 engaged the relative axial position between the working tool 46 and the elongate sleeve 72 is maintained in the absence of an axial force applied to the working tool 46 and/or the elongate sleeve 72.

Referring to FIG. 8A, the tool assembly 40 is positioned and advanced within the soft tissue T overlying the bony anatomy B. In particular, the elongate sleeve 72 is advanced within an incision previously formed within the tissue T (such as via the working tools 46a or 46b). As the elongate sleeve 72 is positioned and advanced within the soft tissue T, the movable features 80 prevent ingress of the soft tissue T within the elongate sleeve 72. In particular, the taper 82 is arranged such that the distal end 76 of the elongate sleeve 72 is substantially or completely closed, and the soft tissue T is urged outwardly as the elongate sleeve 72 is advanced within the soft tissue T. Further, as the elongate sleeve 72 is advanced within the soft tissue T, the complementary locating features 90, 92 remain engaged such that the axial position of the working tool 46 relative to the elongate sleeve 72 is maintained. In particular, the working section 68 is maintained in a position slightly proximal to the movable feature 80 of the elongate sleeve 72.

The tool assembly 40 may be positioned with the distal end 76 of the elongate sleeve 72 at or near the underlying bony anatomy B to provide a working channel through substantially an entirety of the soft tissue T overlying the bony anatomy B. In one example, the distal end 76 of the elongate sleeve 72 is positioned one to two millimeters above the bony anatomy B. With the tool assembly 40 suitably positioned within the soft tissue T, the axial position of the working tool 46 relative to the elongate sleeve 72 is altered. The complementary locating features 90, 92 may be disengaged to alter the axial position.

In one version, shown in FIG. 8B, movement of the working tool 46 relative to the elongate sleeve 72 is caused by retracting proximally the elongate sleeve 72 relative to the working tool 46. Positions of the drive coupler 42a and the working tool 46 are maintained, for example, with the input device 44. The elongate sleeve 72 is moved in the direction of arrow 98 relative to the position of the working tool 46. The elongate sleeve 72 may be retracted manually by the surgeon or with a device (not shown) coupled to the elongate sleeve 72. With the elongate sleeve 72 having previously dilated and retracted the soft tissue T during the step of advancing the tool assembly 40 within the soft tissue T, no significant resistance should be encountered during the proximal retraction of the elongate sleeve 72. The result of altering the axial position of the elongate sleeve 72 is the working tool 46 puncturing and partially opening the distal end 76 of the elongate sleeve 72. More specifically, the working section 68 may urge the tabs 84 to deflect outwardly as the distal end 76 of the elongate sleeve 72 is pulled proximally over the working section 68. FIG. 8B shows the working section 68 positioned within the soft tissue T beyond the distal end 76 of the elongate sleeve 72 after proximal retraction of the elongate sleeve 72. In such an exemplary embodiment, the entire tool assembly 40 may then be advanced to drive the working section 68 into the bony anatomy B and to position the distal end 76 of the elongate sleeve 72 near or at the underlying bony anatomy B. The working section 68 may be driven into the bony anatomy B by rotation of the drive coupler 42a. Frictional contact between the soft tissue T and the outer surface of the elongate sleeve 72 resists corresponding rotation of the elongate sleeve 72, and the working tool 46 may have sufficient space inside the elongate sleeve 72 so that the working tool 46 is able to rotate inside the elongate sleeve 72 without causing corresponding rotation of the elongate sleeve 72. In other embodiments, it may be desired to rotate both the working tool 46 and the elongate sleeve 72.

In another version shown in FIG. 8C, the working tool 46 is advanced distally while the elongate sleeve 72 remains positioned near or at the underlying bony anatomy B, as in FIG. 8A. The working section 68 advances into the bony anatomy B away from the elongate sleeve 72 thereby exposing the working section 68 beyond the distal end 76 of the elongate sleeve 72.

With reference to FIGS. 8A and 8C, the elongate sleeve 72 may comprise teeth, spikes, or other anti-skid features to prevent lateral movement of the elongate sleeve 72 relative to the bony anatomy B. In the version shown, the elongate sleeve 72 comprises bone penetrating spikes 93 fixed to the distal end of the elongate sleeve 72. Once the elongate sleeve 72 is pushed through the soft tissue T into contact with the bony anatomy B, then the elongate sleeve 72 may be further advanced distally to be partially embedded within the bony anatomy B' by driving the spikes 93 into the bony anatomy B. In some cases, a mallet or other device may be used to impact the elongate sleeve 72 to embed the spikes 93 into the bony anatomy B. The embedding of the elongate sleeve 72 within the bony anatomy B provides the working channel through an entirety of the overlying soft tissue T, and may further prevent unintended lateral movement of the tool assembly 40 relative to the bony anatomy B (e.g., to prevent skiving of the working section 68 upon contact with the bony anatomy B'). Subsequent to embedding the spikes into the bony anatomy B, the working tool 46 is further advanced distally relative to the elongate sleeve 72 in order to manipulate the bony anatomy B. In one variant, the teeth, spikes, or other anti-skid features may be deployable to be advanced distally from an initial position to a deployed position. For example, the spikes may be positioned within a bore in the initial position, and a biasing element (e.g., a spring) biases the spikes outwardly. A release mechanism may maintain the spikes within the bore against the biasing force from the biasing element. The user may actuate the release mechanism, after which the biasing element moves the spikes within the bore from the initial position to the deployed position in which a tip of the spike is beyond the distal end of the elongate sleeve 72 to penetrate the bony anatomy.

The input device 44 may be operated to move the drive coupler 42a, 42b with the movement being transferred to the working tool 46. In certain embodiments previously described, the movement of the drive coupler 42a, 42b includes the input device 44 providing a torque to rotate the drive coupler 42a, 42b with the rotation being transferred to the working tool 46. In the exemplary embodiments of FIGS. 8A-8C, the working tool 46 is rotated while being advanced distally into the underlying bony anatomy B. In other embodiments, the input device 44 may advance the working tool 46 via translation, rotation, oscillation, or combinations thereof.

Figure 9:
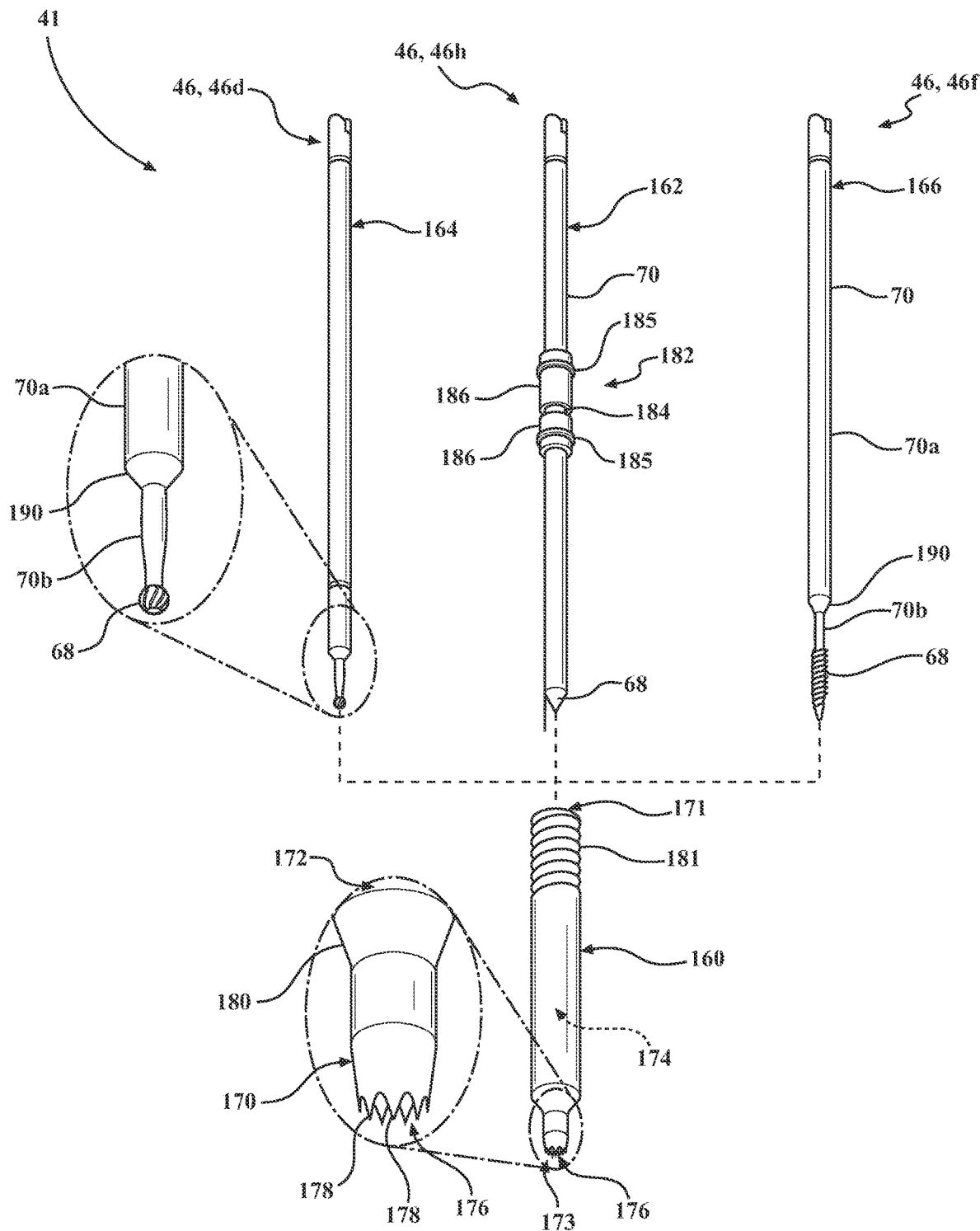
FIG. 9 is a schematic representation of a tool assembly with an elongate sleeve adapted to receive one of several working tools.

FIG. 9 shows the tool assembly 41 including one of the working tools 46, which includes the proximal shaft portion 70 and the working section 68. Specific discussion is provided for certain embodiments of the working tools 46d, 46f, 46h, 46i including dilator probe 162, the bur 164, the drill 166, and the tap inserter shown in FIGS. 9 and 10A-10C, but it is to be understood that other working tools 46 may be implemented in the tool assembly 41.

The tool assembly 41 includes the elongate sleeve 160. In at least some respects the elongate sleeve 160 of the embodiment shown in FIG. 9 is the same as that previously described (see FIGS. 2 and 7). The elongate sleeve 160 is of suitable size and shape to be moved into an incision within the overlying tissue, for example, a relatively small incision during minimally invasive surgery. The elongate sleeve 160 includes or defines a cavity 174 (identified in phantom) between the proximal and distal ends 171, 173. In other words, the cavity 174 is defined by an inner surface (not shown) of the elongate sleeve 160. In the exemplary embodiment illustrated in FIG. 9, the cavity 174 may be considered a lumen that extends an entirety between openings at the proximal and distal ends 171, 173. The cavity 174 is sized and shaped to receive at least a portion of the working tool 46. In particular, the cavity 174 is sized and shaped to receive at least the working section 68 of the working tool 46 and provide a working channel for the working tool 46 within the tissue. The elongate sleeve 160 is formed from material with suitable stiffness to maintain patency of the cavity 174 when the elongate sleeve 160 is positioned within the tissue. In one example, the elongate sleeve 160 is formed from polymeric material with the elongate sleeve 160 comprising a disposable component of the tool assembly 41. In some embodiments, the elongate sleeve 160 may be formed of metal, such as aluminum or stainless steel, or other suitable materials.

The elongate sleeve 160 includes an engagement feature 176 at the distal end 173 and for engaging the underlying bony anatomy. In the version shown, the engagement feature 176 comprises bone penetrating spikes 178 fixed to and circumferentially spaced about the distal end 173 of the elongate sleeve 160. Once the elongate sleeve 160 is pushed through the soft tissue into contact with the bony anatomy, the elongate sleeve 160 may be further advanced distally to be partially embedded within the bony anatomy by driving the spikes 178 into the bony anatomy. In some cases, a mallet or other device may be used to impact the elongate sleeve 160 to embed the spikes 178 into the bony anatomy. The embedding of the elongate sleeve 160 within the bony anatomy provides the working channel through an entirety of the overlying soft tissue to the underlying bony anatomy, and may further prevent unintended lateral movement of the tool assembly 41 relative to the bony anatomy (e.g., to prevent skiving of the working section 68 upon contact with the bony anatomy). Subsequent to embedding the spikes into the bony anatomy, the working tool 46 may be further advanced distally relative to the elongate sleeve 160 in order to manipulate the bony anatomy.

The elongate sleeve 160 includes a distal tubular section 170 defining the distal end 173, and a proximal tubular section 172 defining the proximal end 171. Each of the tubular sections 170, 172 has an outer diameter. The tubular sections 170, 172 may collectively define the cavity 174. For example, the distal tubular section 170 may define a portion of the cavity 174 nearer the distal end 173, and the proximal tubular section 172 may define another portion of the cavity 174 nearer the proximal end 171. The outer diameter of the distal tubular section 170 may be less than the outer diameter of the proximal tubular section 172. In such an arrangement, the elongate sleeve 160 widens along its length from the distal end 173 to the proximal end 171 such that, as the elongate sleeve 160 is moved into the incision of the tissue, the elongate sleeve 160 retracts or dilates the tissue. A tapering section 180 may be provided intermediate to the tubular sections 170, 172 to provide a contour similar to that shown in FIG. 9. The tapering section 180 facilitates incremental or "smooth" retraction or dilation of the tissue as the elongate sleeve 160 is moved into the incision of the tissue. In one example, the elongate sleeve 160 includes a length of approximately 110 millimeters comprised of the distal tubular section 170 having a length of 13 millimeters, the tapering section 180 having a length of 7.5 millimeters, and the proximal tubular section 172 having a length of 88 millimeters. In another example, the elongate sleeve 160 includes a length of approximately 110 millimeters comprised of the distal tubular section 170 having a length of 19 millimeters, the tapering section 180 having a length of 7.5 millimeters, and the proximal tubular section 172 having a length of 82 millimeters. It is understood that other respective lengths of the proximal and distal tubular sections 170, 172 and the tapering section 180 are contemplated.

Further to the outer diameter of the distal tubular section 170 being less than the outer diameter of the proximal tubular section 172, an inner diameter of the distal tubular section 170 may be less than an inner diameter of the proximal tubular section 172. In one example, a thickness of the proximal and distal tubular sections 170, 172 defined between their respective inner and outer diameters may be substantially constant such that the contour of the outer surface is imparted to the inner surface. Stated differently, a portion of the cavity 174 within the proximal tubular section 170 may be greater in diameter than another portion of the cavity 174 defined within the distal tubular section 172. The arrangement provides for a reduction in inner diameter along the length of the elongate sleeve 160 from the proximal end 171 to the distal end 173. In one non-limiting example, the distal tubular section 170 may have an outer diameter of 14 millimeters and an inner diameter of 9.8 millimeters, and the proximal tubular section 172 may have an outer diameter of 9.2 millimeters and an inner diameter of 6.8 millimeters. It is understood that other respective inner and outer diameters of the proximal and distal tubular sections 170, 172 are contemplated.

Figure 10A:
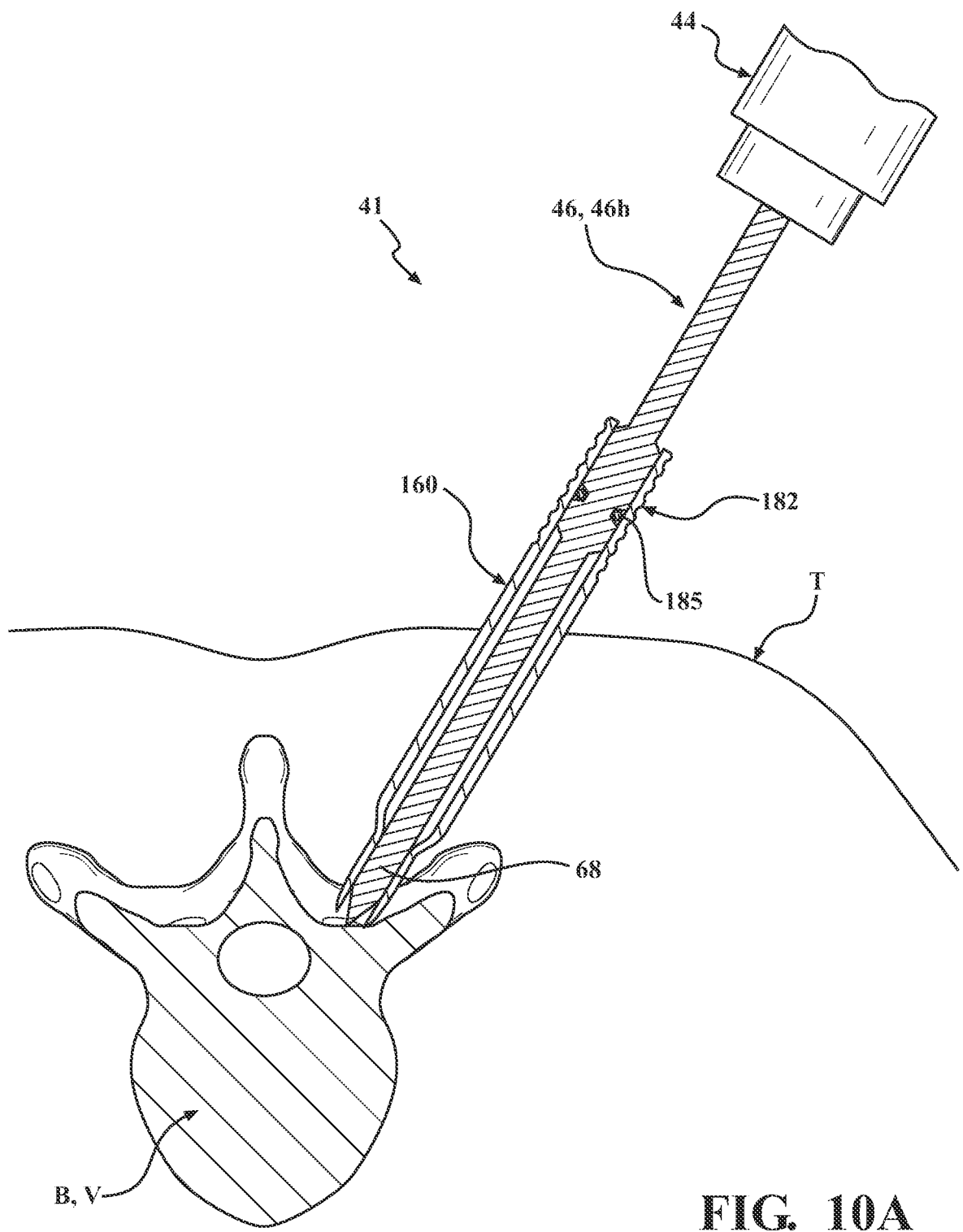
FIG. 10A is a sectional view of the tool assembly of FIG. 9 with a dilator probe positioned within an elongated sleeve.

As the working tool 68 is adapted to be positioned beyond the distal end 173 of the elongate sleeve 160, it readily follows that an outer diameter of the working section 68 of the working tool 46 is less than the inner diameter of the distal tubular section 170. In certain embodiments, the outer diameter of the working section 68 is approximate the inner diameter of the distal tubular section 170. In other words, the working section 68 and the inner surface of the elongate sleeve 160 are at least nearly in contact with no appreciable gap therebetween when the working tool 46 is operably disposed within the cavity 174. In other words, the working tool 46 and elongate sleeve 160 are dimensioned such that the working tool 46 is snugly and slidably received within the cavity 174 of the elongate sleeve 160. For example, FIGS. 9 and 10A show the elongate sleeve 160 as a substantially tubular structure with the dilator probe 162 having a generally cylindrical shape with an outer diameter no greater than an inner diameter of the elongate sleeve 160. As a result, as the elongate sleeve 160 is moved into the incision of the tissue with the dilator probe 160 disposed therein and a tip (i.e., a tip of the working section 68) of the dilator probe 160 positioned distal to the distal end 173 of the elongate sleeve 160, the tissue is substantially prevented from entering the cavity 174, also known as "coring."

In one variant of the workflow, the elongate sleeve 72, 160 is separate from the working tool 46 and manually advanced within an incision previously formed within the tissue T. At the time the elongate sleeve 72, 160 is positioned within the incision, the working tool 46 may be coupled to the input device 44 and positioned away from the tissue. The elongate sleeve 72, 160 may be positioned such that the distal end 76 of the elongate sleeve 72, 160 at or near the underlying bony anatomy B to provide a working channel through substantially an entirety of the soft tissue T overlying the bony anatomy B. The proximal end 74 of the elongate sleeve 72, 160 is positioned above the overlying soft tissue, for example as shown in FIGS. 8A-8C. The user may manually manipulate the proximal end 74 of the elongate sleeve 72, 160 that is exposed. The working tool 46 (e.g., the tap marker 100) may be moved to the insertion trajectory, then advanced distally towards the proximal end 74 of the elongate sleeve 72, 160. Particularly with the incision being formed with the scalpel attachment 46a such that the manipulator constrained the incision along the insertion trajectory, the elongate sleeve 72, 160 and the advancing working tool 46 should be substantially in alignment. Owing to the compliancy of tissue generally, small adjustments may be made to the elongate sleeve 72, 160 by manually manipulating the proximal end 74 of the elongate sleeve 72, 160. The working section 68 of the working tool 46 is directed through the proximal end 74 of the elongate sleeve 72, 160 and into the cavity 78 as the manipulator constrains movement of the working tool 46 along the insertion trajectory. The workflow may proceed as described throughout the present disclosure.

For example and with continued reference to FIG. 9, the elongate sleeve 160 is adapted to be manually manipulated by the surgeon during advancement or retraction of the elongate sleeve 160 within the tissue. The elongate sleeve 160 may include gripping features 181, such as grooves, indentations, protrusions, and the like, to facilitate the manual manipulation of the elongate sleeve 160. Further, in certain embodiments the working tool 46, in particular the dilator probe 162, is adapted to be manually manipulated by the surgeon as during advancement or retraction of the elongate sleeve 160 and the dilator probe 162 within the tissue. As a result, with one hand of the surgeon operating the input device 44, the other hand of the surgeon is free to perform other aspects of the surgical procedure. It is also understood that the dilator sleeve 162 may be coupled to an input device (see FIG. 3), for example, with the drive coupler 42*a*, 42*b* previously described. In other words, tool assembly 41 may be supported at the coupler proximal end 58 of the drive coupler 42*a*, 42*b* coupled to the input device 44 (see FIG. 7).

In embodiments where the dilator probe 162 is separately supported by the surgeon and/or coupled to the input device 44, it may be desirable to maintain, at least initially, an axial position of the working tool 46 relative to the elongate sleeve 160. For example, with the dilator probe 162 coupled to the input device 44 supported by the robotic arm 36, separately supporting the elongate sleeve 160 prior to advancing the elongate sleeve 160 and the dilator probe 162 may be undesirable. The dilator probe 162 of FIG. 9 includes a locating feature 182 annularly coupled to the proximal shaft portion 70 with the locating feature 182 comprising an outer diameter approximate the inner diameter of the elongate sleeve 160, and more particularly the proximal tubular section 172 of the elongate sleeve 160. The outer diameter of the locating feature 182 being approximate the inner diameter of the elongate sleeve 160 provides a defeatable frictional engagement that maintains the axial position of the dilator probe 162 relative to the elongate sleeve 160 in the absence of an axial force applied to one of the dilator probe 162 and the elongate sleeve 160. In at least some respects, the locating feature 182 of the embodiment illustrated in FIG. 9 is similar to the locating feature 96 of the working tool 46 of the embodiment illustrated in FIG. 7. In one example, the locating feature 182 is a portion 186 of the shaft 70 cylindrical in shape and having a larger outer diameter (e.g., a bushing fixed to the shaft 70) than the outer diameter of the remaining portion of the shaft 70. The locating feature 182 may provide a proximal depth-limiting feature for the elongate sleeve 160 should the elongate sleeve 160 be retracted (i.e., moved proximally) while the dilator probe 162 is maintained in a desired pose with the robotic arm 36. In particular, as the elongate sleeve 160 be retracted with the dilator probe 162 is maintained in a desired pose, the tapering portion 180 of the elongate sleeve 160 eventually contacts the portion 186 of the shaft 70 such that the elongate sleeve 160 may no longer be retracted proximally. An axial position of the portion 186 may be designed such that, when the elongate sleeve 160 is retracted to the maximum extent permissible (i.e., the tapering portion 180 contacts the portion 186), the distal end 173 of the elongate sleeve 160 remains within the overlying tissue.

Furthermore, one or more undercuts 184 or slots may be within the cylindrical portion 186, and one or more seals 185 may be provided within the undercuts 184 to provide the defeatable frictional engagement with the inner surface of the elongate sleeve 160. In other words, the friction between the seal(s) 185 and the inner surface is sufficient to maintain the axial position of the dilator probe 162 relative to the elongate sleeve 160 in the absence of an axial force applied to one of the dilator probe 162 and the elongate sleeve 160, but with sufficient axial force applied to one of the dilator probe 162 and the elongate sleeve 160, the relative axial position may be altered. Such a feature may be particularly advantageous to prevent coring during advancement of the elongate sleeve 160 and the dilator probe 162 within the tissue to the underlying bony anatomy, but permit the surgeon to remove the dilator probe 162 with relative ease. FIG. 9 shows the tool assembly 41 with two seals 185 positioned within the undercuts 184 if the locating feature 185, and FIG. 10A shows the tool assembly 41 with one seal 185 positioned within the undercuts 184 of the locating feature 182.

With the engagement feature 176 of the elongate sleeve 160 engaging the bony anatomy, the surgeon removes the dilator probe 162 to create the working channel through the overlying tissue. Another one of the working tools 46, for example the bur 164 and/or the drill 166 of FIG. 9, may be inserted through the elongate sleeve 160 to manipulate the underlying bony anatomy. Each the bur 164 and the drill 166 is sized and shape to be operably positioned within the cavity 174 of the elongate sleeve 160 in an advantageous manner. In particular, the bur 164 and/or the 166 include the shaft 70 and the working section 68 with the shaft 70 further defined by a proximal section 70*a* and a distal section 70*b*. The working section 68 is distal to the distal section 70*b* of the shaft 70, as shown in FIG. 9. The distal section 70*b* includes an outer diameter less than an outer diameter of the proximal section 70*a*. A tapering section 190 may be intermediate the proximal section 70*a* and the distal section 70*b* of the shaft 70 such that the shaft 70 is generally contoured to the inner surface of the elongate sleeve 160.

Figure 10B:
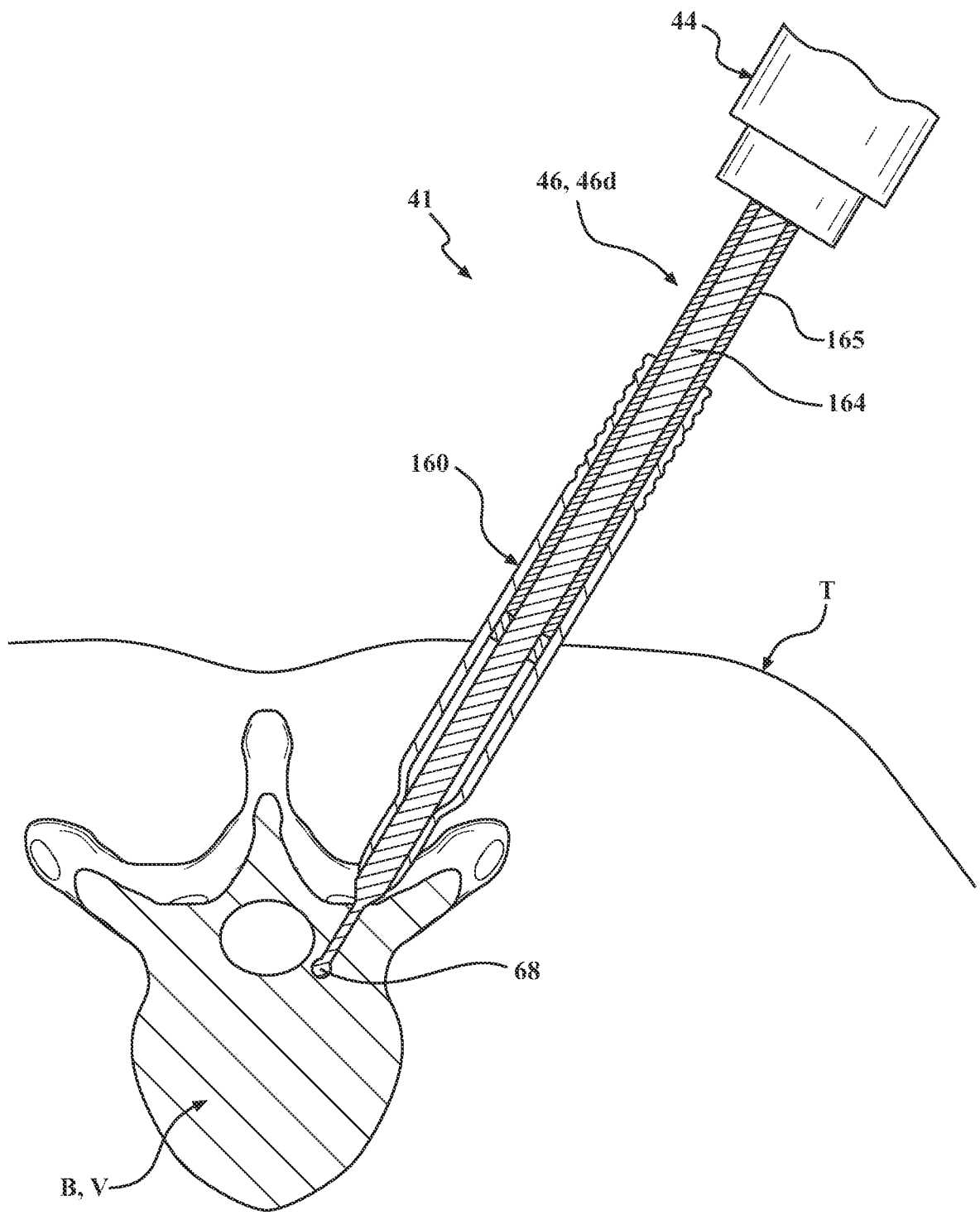
FIG. 10B is a sectional view of the tool assembly of FIG. 9 with a bur positioned within the elongated sleeve of FIG. 10A.
Figure 10C:
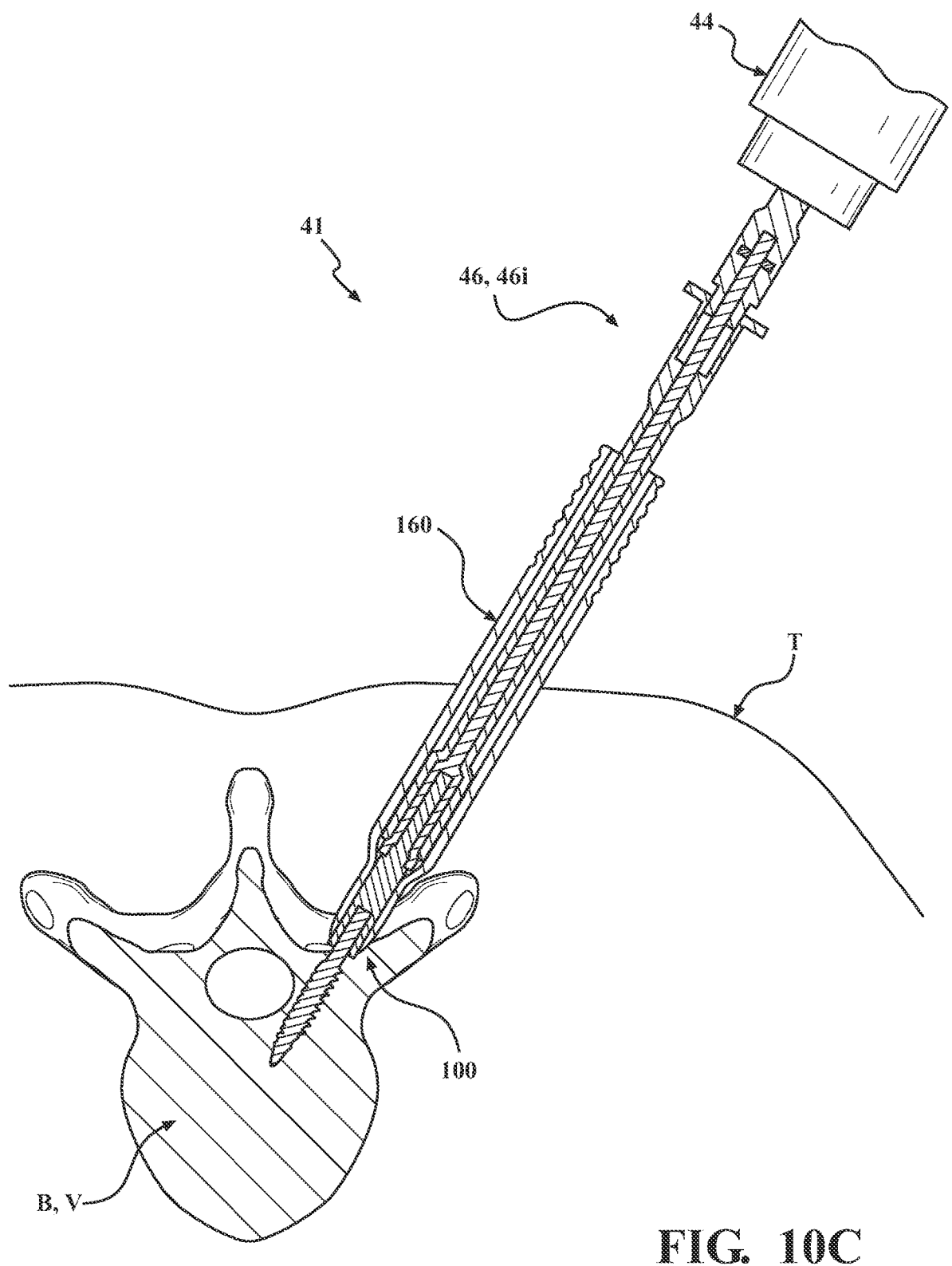
FIG. 10C is a sectional view of the tool assembly of FIG. 9 with a tap inserter positioned within the elongated sleeve of FIG. 10A for placement of a tap marker within the underlying bony anatomy.

An operation of the tool assembly 41 is now described in the exemplary steps of preparing a pilot hole and placement of a tap marker 100 (see FIGS. 13, 17 and 20) within the pilot hole. In at least some respects the operation of the tool assembly 41 to be descried is similar to the tool assembly 40 previously described and illustrated in FIGS. 8A-8C. The elongate sleeve 160 and the dilator probe 162 is provided with the dilator probe 162 disposed within the cavity 174 of the elongate sleeve 160. The locating feature 182 provide the defeatable frictional engagement with the inner surface of the elongate sleeve 160 to maintain the axial position of the dilator probe 162 relative to the elongate sleeve 160. In one example, the tip of the working section 68 of the dilator probe 162 may extend slightly beyond the distal end 171 of the elongate sleeve 160 so as to assist with advancing the tool assembly 41 within the overlying tissue. A proximal end of the dilator probe 162 is coupled to the robotic arm 36, such as with the drive coupler 42*a*, 42*b* removably coupled to the input device 44. The tool assembly 41 is positioned and advanced within the soft tissue T overlying the bony anatomy B. The bony anatomy B of FIGS. 10A-10C is a vertebral body V for placement of the tap marker 100 within the pedicle of the same (see also FIGS. 22 and 23).

FIG. 10A shows the elongate sleeve 160 advanced within an incision previously formed within the tissue (such as via the working tools 46*a* or 46*b*). As the elongate sleeve 160 is positioned and advanced within the soft tissue, the working section 68 of the dilator probe 162 prevent ingress of the soft tissue within the elongate sleeve 160. In particular, the working section 68 is sized arranged such that the distal end 173 of the elongate sleeve 160 is substantially or completely closed, and the soft tissue is urged outwardly as the elongate sleeve 160 is advanced within the soft tissue. Further, as the elongate sleeve 160 is advanced within the soft tissue, the locating feature 182 maintains the axial position of the working tool 162 relative to the elongate sleeve 160. The elongate sleeve 160 is positioned at or near the underlying bony anatomy to provide the working channel through substantially an entirety of the soft tissue overlying the bony anatomy. The elongate sleeve 160 is partially embedded within the bony anatomy by driving the spikes 178 into the bony anatomy. As mentioned, a mallet or other device may be used to impact the elongate sleeve 160 to embed the spikes 178 into the bony anatomy. The embedding of the elongate sleeve 160 within the bony anatomy may also include the working section 68 of the dilator probe 162 penetrating the bony anatomy, for example, forming a small, conical-shaped indentation. In another example, the working section 68 of the dilator probe 162 is positioned at or near the bony anatomy, and the elongate sleeve 160 is moved distally relative to the dilator probe 162 to cause the embed the spikes 178 into the bony anatomy. Such an example may require providing sufficient axial force on the elongate sleeve 160 relative to the dilator probe 162 to overcome the locating feature 182.

The dilator probe 162 is removed to create the working channel through the overlying tissue to the underling bony anatomy. FIG. 10B shows the bur 164 inserted through the elongate sleeve 160 to manipulate the underlying bony anatomy B. The bur 164 is coupled to the robotic arm 36, such as with the drive coupler 42a, 42b and/or the input device 44 represented schematically in FIGS. 10A-10C. A bur guard 165 may be provided intermediate the shaft 70 of the bur 164 and the inner surface of the elongate sleeve 160 with the bur guard 165 configured to remain stationary as the bur 164 is rotated. FIG. 10B shows the bur guard 165 extending from the input device 44 along a majority of the length of the bur 164. The bur guard 165 is configured to eliminate exposing physicians to portions of the bur 164 often rotating at high speeds. FIG. 10B shows the bur guard 165 as a thin, tubular structure sized to encircle the shaft 70 of the bur and slidably move within the elongate sleeve 160. The bur guard 165 may be flexible or rigid, and formed from or coated with materials designed to limit friction from the bur 164. In certain embodiments, the operation of the bur 164 is controlled by the robotic system 32 and the pilot hole is drilled to a desired depth and in a desired pose. The input device 44 is operated to move the drive coupler 42a, 42b with the movement being transferred to the bur 164. The movement of the drive coupler 42a, 42b includes the input device 44 (e.g., a high RPM rotary attachment) providing a torque to rotate the drive coupler 42a, 42b with the rotation being transferred to the working tool 46d. The bur 164 is rotated while being advanced distally into the underlying bony anatomy to create the pilot hole. In certain embodiments, the working section 68 of the bur 164 is a 3 millimeter monolithic bur head, such as a precision match head, a precision round head, or a fluted round head. The shaft sections 70a, 70b of the bur 164 may be configured to extend beyond the distal end 173 of the elongate sleeve 160 by approximately 16 millimeters; however, other lengths of protrusion are contemplated based on the surgical application.

The bur 164 is removed from within the elongate sleeve 160, thereby reestablishing the working channel through the overlying tissue T to the underling bony anatomy B. FIG. 10C shows the tap inserter 46i with the tap marker 100 being inserted through the elongate sleeve 160 to the underlying bony anatomy B. In manners to be described in further detail, the tap inserter 46i is coupled to the robotic arm 36 with the robotic system 32 controlling the robotic arm 36 to place the tap marker 100 within the bony anatomy at a desired depth and in a desired pose. In particular, a low RPM rotary attachment, for example, a reamer connection, may provide a torque to rotate the drive coupler 42a, 42b with the rotation being transferred to the working tool 46i. The exemplary operation described above may be repeated as desired.

The tool assembly 40, 41 advantageously provides for decoupling the drive coupler 42a, 42b from the working tool 46 while the working tool 46 remains secured within the underlying bony anatomy B. For example, the working tool 46 may be the tap drill 46e (see FIGS. 3 and 11) or the tap marker 100 (see FIGS. 8 and 12 illustrating two different versions of tap markers) that function by being temporarily installed in the bony anatomy B. It may be desired to leave the tap marker 100 secured within the bony anatomy during other steps of the surgical procedure with the tap marker 100 to be subsequently utilized to relocalize the bony anatomy B with the navigation system 32. With the working section 68 firmly secured within the underlying bony anatomy B, the drive coupler 42a, 42b is retracted proximally, for example, with the input device 44. The proximal retraction of the drive coupler 42a, 42b is with an axial force sufficient to disengage the complementary locking features 65, 67 of the working tool 46 and the drive coupler 42a, 42b. The drive coupler 42a, 42b is retracted proximally and removed from the elongate sleeve 72 while the elongate sleeve 72 remains positioned within the soft tissue T and while the working tool 46 remains secured within the underlying bony anatomy B. The elongate sleeve 72 maintains the working channel through the soft tissue T with the working channel at least extending to and providing access to a proximal end 75 of the proximal shaft portion 70 of the working tool 46. Further, with the drive coupler 42a, 42b decoupled from the working tool 46 and removed from the surgical site, less obstruction is present near the surgical site for other aspects of the surgical procedure. To remove the working tool 46 from the underlying bony anatomy, the drive coupler 42a, 42b may be quickly recoupled to the working tool 46 in manners previously described. The working tool 46 may be removed from within the bony anatomy B for placement of an implant and the like.

The navigation system 32 includes the localizer 34 for detecting tracking devices (e.g., tracking device 50 of FIG. 3, tracking device 102 of FIG. 10, etc.), also referred to herein as trackers. The localizer 34 may be an optical localizer and includes a camera unit (one example of a sensing device) with one or more optical position sensors. In some embodiments, at least two optical sensors are employed, sometimes three or more. The optical sensors may be separate charge-coupled devices (CCD) with a field of view that, ideally, is free from obstructions between the optical sensors and the tracking devices. The localizer 34 includes a localizer controller (not shown) in communication with the optical sensors to receive signals from the optical sensors. Position and orientation signals and/or data are transmitted to a navigation computer for purposes of tracking the objects; i.e., localizing the pose of the tracking device relative to a global coordinate system known to the robotic controller 52.

Localization techniques include trackers with mechanical clamps that releasably secured to the spinous process of the vertebra(e) of interest, and trackers with fasteners such as bone screws, bone pins, or the like, rigidly secured to the vertebra V of interest. The trackers secured to the vertebrae extend upwardly from the patient so as to be detectable by the localizer 34 with the patient being typically placed in the prone position. While the trackers beneficially move with any movement of the bony anatomy to which they are secured, the trackers require appreciable space at or near the surgical site, particularly in surgical procedures using the robotic system 30. Another localization technique includes tracking device(s) secured to other tissue types or parts of the anatomy, for example, the pelvis of the patient. With the tracking device secured remote from the vertebra V of interest, obstruction near the surgical site is lessened; however, relative movement between the vertebra V of interest and the tracking device secured to the pelvis may be excessive in the robotic-assisted surgical procedure, which requires precise tracking. For example, movement between adjacent vertebrae (and relative to the pelvis) may occur during discectomy and cage placement aspects of a spinal fusion procedure. If the relative movement between the vertebra(e) of interest and the tracking device is not detected, or if the vertebra(e) is not subsequently relocalized, positional error may occur during robotic-assisted placement of the pedicle screw into the vertebra(e) of interest.

The tool assembly 40, 41 advantageously provides for efficient relocalizing (also referred to herein as reregistering) of the bony anatomy to the navigation system 32 for navigation-assisted preparation of the bony anatomy B or for verifying registration. The relocalizing of the bony anatomy compensates or accounts for any movement of the bony anatomy during certain steps of the surgical procedure, for example, during the discectomy and cage placement aspects of the spinal fusion procedure. Registration verification can be performed to confirm that the bony anatomy did not move beyond predetermined thresholds.

Referring to FIG. 7, in certain embodiments the working tool 46 includes a navigation feature 101. The navigation feature 101 has a fixed position relative to the working section 68 of the working tool 46. During the surgical procedure, only a portion (e.g., the proximal shaft portion 70) of the working tool 46 may extend above the overlying soft tissue T without significant obstruction of the surgical site to the surgeon and the robotic arm 36. In this case, the navigation feature 101 extends outside of the patient. In one example, the navigation feature 101 is a divot at the proximal end 75 of the proximal shaft portion 70 of the working tool 46. The navigation feature 101 is adapted to be "touched off" by a digitizing probe 106 (e.g., navigation pointer of FIG. 1) trackable by the localizer 34. Based on knowing the position of the navigation feature 101 when the working tool 46 was originally positioned with navigation-assistance, the position of the working tool 46 may be checked by the navigation system 32 while the working tool 46 remains secured within the bony anatomy (see FIG. 8C). More specifically, if the working tool 46 is originally placed in the bony anatomy B with navigation assistance and thereby, the position of the navigation feature 101 is known in a coordinate system used by the navigation system for tracking, then touching the divot with the digitizing probe 106 can confirm that the working tool 46 remained relatively stationary, or conversely, that appreciable movement of the working tool 46 occurred.

The "touching off" of the navigation feature 101 with the trackable probe 106 may be used to generally determine whether a position of the working tool 46 changed. It may be desirable to further determine the current position and/or orientation of the working tool 46 secured within the bony anatomy. Referring to FIG. 10, the tracking device 102 may be removably coupled to the working tool 46 (e.g., the drill tap 46e). The tracking device 102 includes one or more markers 108 detectable by the localizer 34 of the navigation system 32. The markers 108 may be passive elements for reflecting light from the localizer 34 back to the optical sensors. In other examples, the markers 108 are active elements, for example, light emitting diodes (LEDs), for transmitting light, such as infrared light to the optical sensors. It should be appreciated that the localizer 34 and markers 108, although described above as utilizing optical tracking techniques, could alternatively, or additionally, utilize other tracking modalities to track the objects, such as electromagnetic (EM) tracking, radio frequency (RF) tracking, inertial tracking, combinations thereof, and the like.

Figure 11:
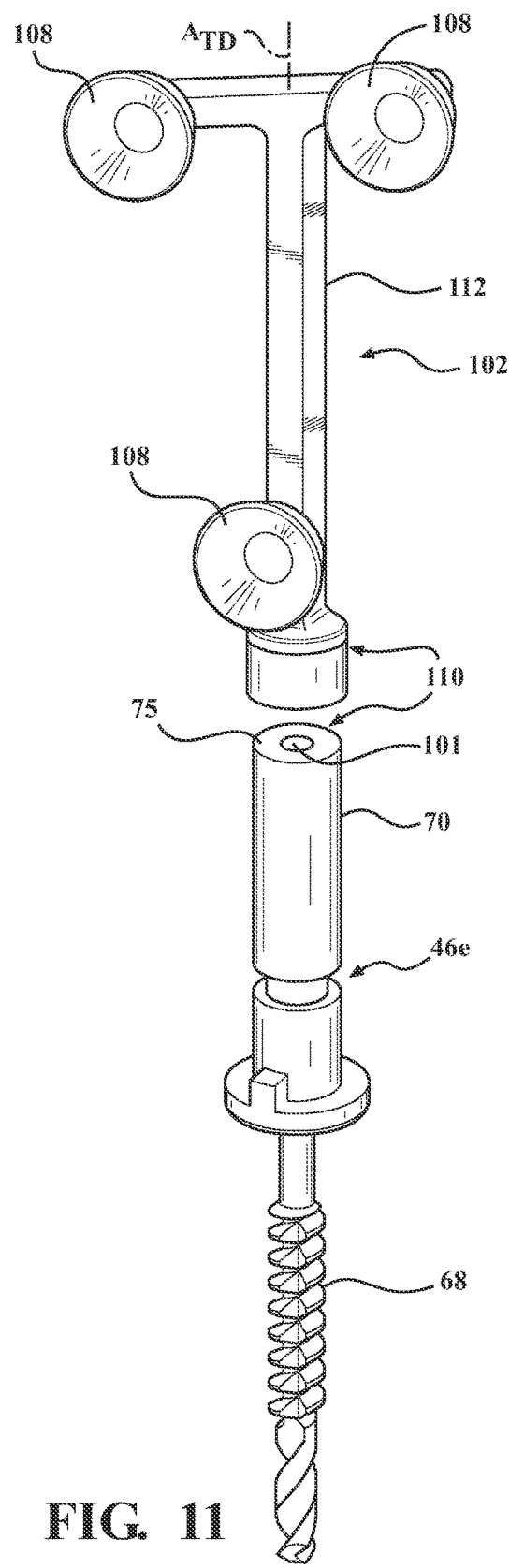
FIG. 11 is an exploded view of another one of the working tools of FIG. 3 with a tracking device adapted to be removably coupled to the working tool.
Figure 12:
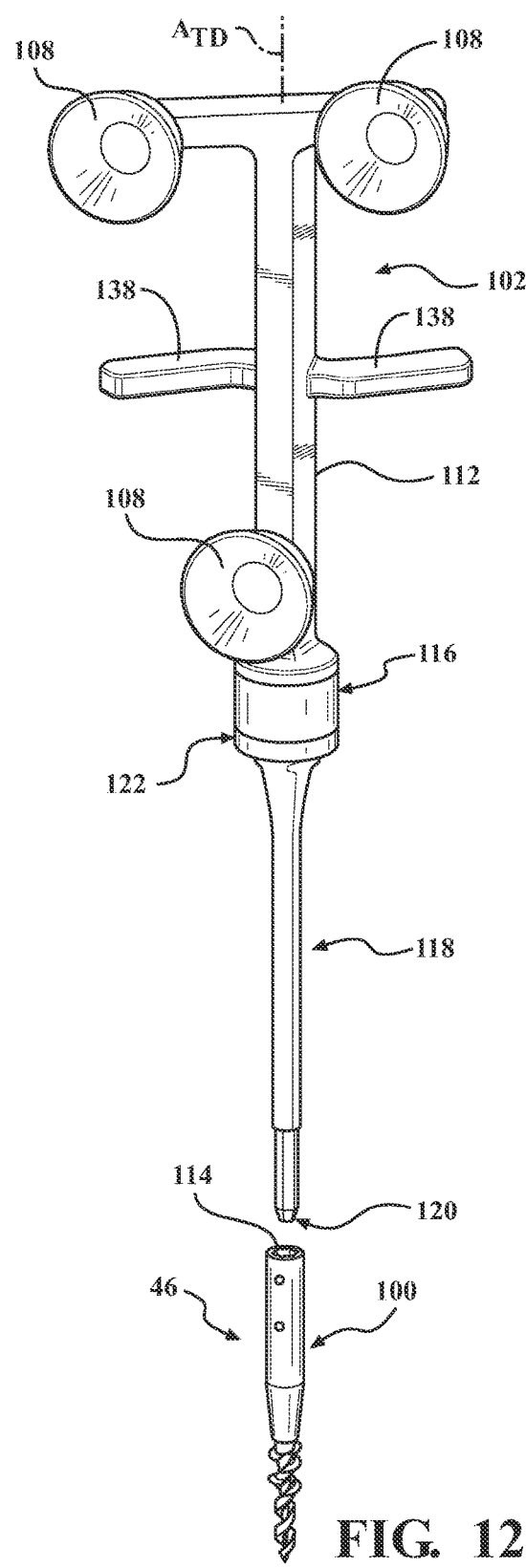
FIG. 12 is an exploded view of a system including a working tool and a tracking device adapted to be removably coupled to the working tool.

The tracking device 102 of FIG. 11 is removably coupled to the working tool 46 with a magnetic coupling. The working tool 46 and the tracking device 102 include complementary magnetic coupling features 110 for removably coupling the working tool 46 with the tracking device 102. In one example, one of the magnetic coupling features 110 is a magnet with the other being a ferromagnetic material. The tracking device 102 may include a shaft 112 with the markers 108 coupled to the shaft 112. The magnetic coupling feature 110 of the tracking device 102 is at a distal end of the shaft 112 with the magnetic coupling features 110 of the working tool 46 at the proximal end 75 of the proximal shaft portion 70. Thus, with the working tool 46 secured in the underling bony anatomy B, the tracking device 102 may be quickly coupled and decoupled from the working tool 46 as necessary to reregister the position of the working tool 46 during the surgical procedure.

Figure 17:
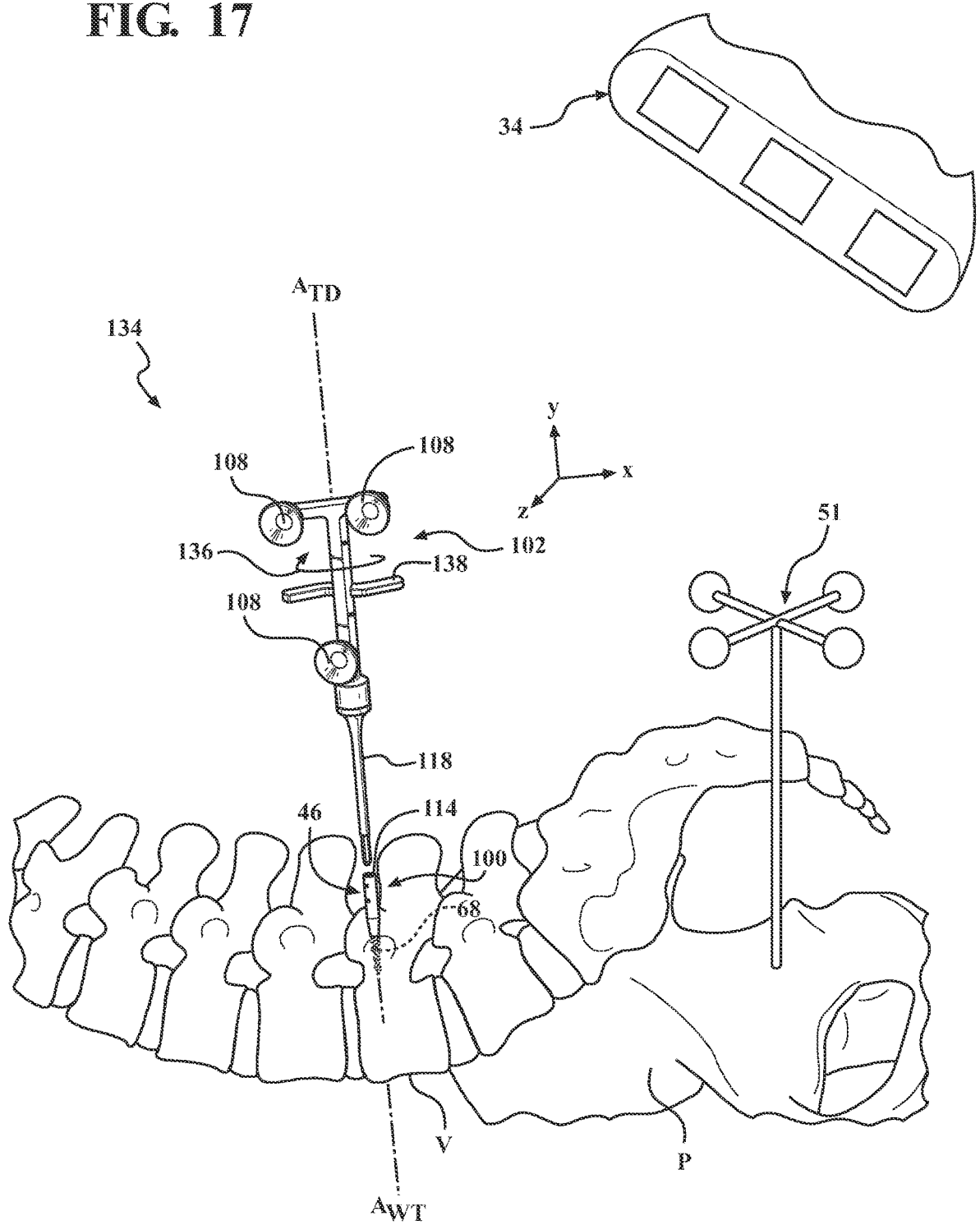
FIG. 17 is a perspective view of the tool assembly of FIG. 12 aligned to be positioned within the pedicle of the vertebra of the spine of FIG. 14.

Moreover, an axis $A_{TD}$ extending through the shaft 112 of the tracking device 102 may be collinear with an axis extending through the proximal shaft portion 70 of the working tool 46 when the tracking device 102 is coupled with the working tool 46 (see FIGS. 11, 12 and 17). For instance, two of the markers 108 can be used to determine an orientation of the axis by measuring positions of the markers at various locations about the axis, and the position and orientation of the working tool 46 can be determined based on a known and stored relationship between the tracking device 102 and the working tool 46 when the tracking device 102 is fully seated on the working tool 46. In other words, calibration data may be stored in the navigation system that correlates a position of the markers 108 to the axis $A_{TD}$ and to the position and orientation of the working tool 46 when the axis $A_{TD}$ is aligned with the axis of the working tool 46 and the tracking device 102 is fully seated on the working tool 46. Based on the received optical signals, the navigation system 32 generates data indicative of the position and orientation (i.e., pose) of the markers 108 relative to the localizer 34, and thus an orientation of the axis $A_{TD}$ extending through the shaft 112 of the tracking device 102. The pose of the working tool 46 may be determined based on the temporarily rigid connection between the tracking device 102 and the working tool 46. Knowing the axis of the working tool 46 is particularly important for subsequent placement of the implant, such as a pedicle screw during the spinal fusion procedure.

Figure 13:
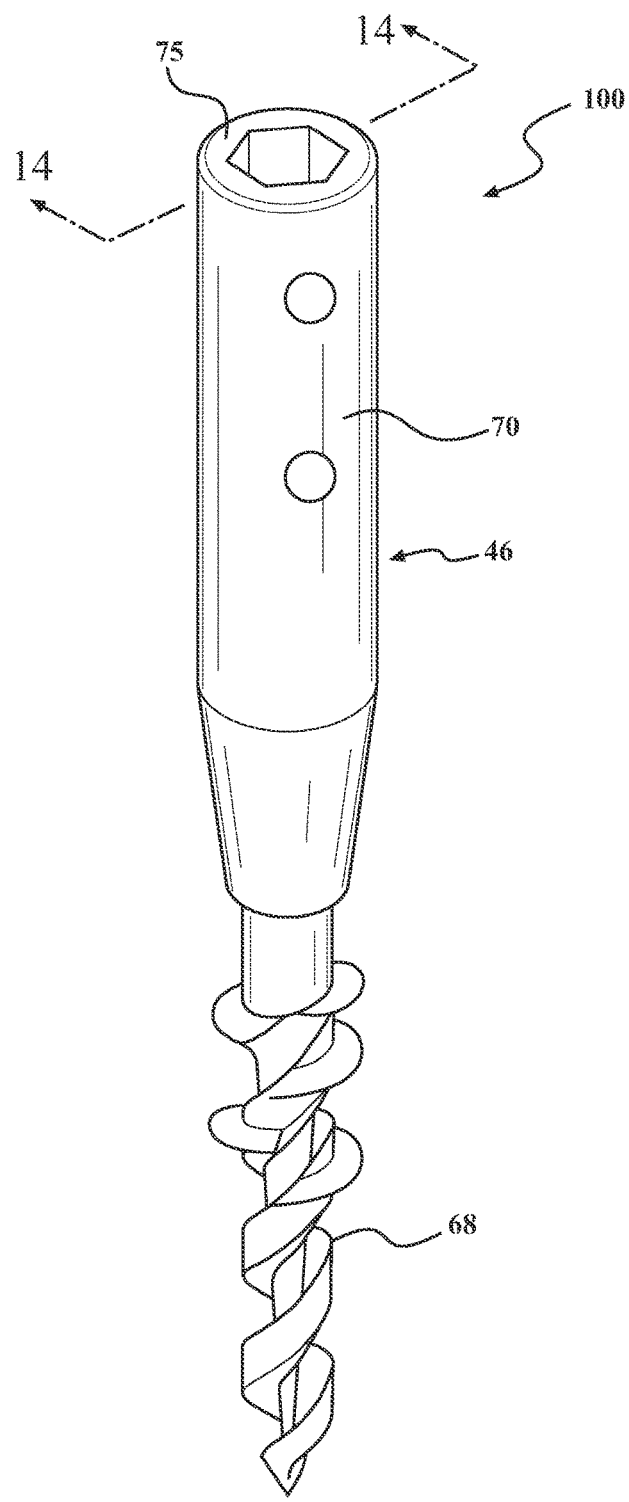
FIG. 13 is a perspective view of the working tool of FIG. 12.
Figure 14:
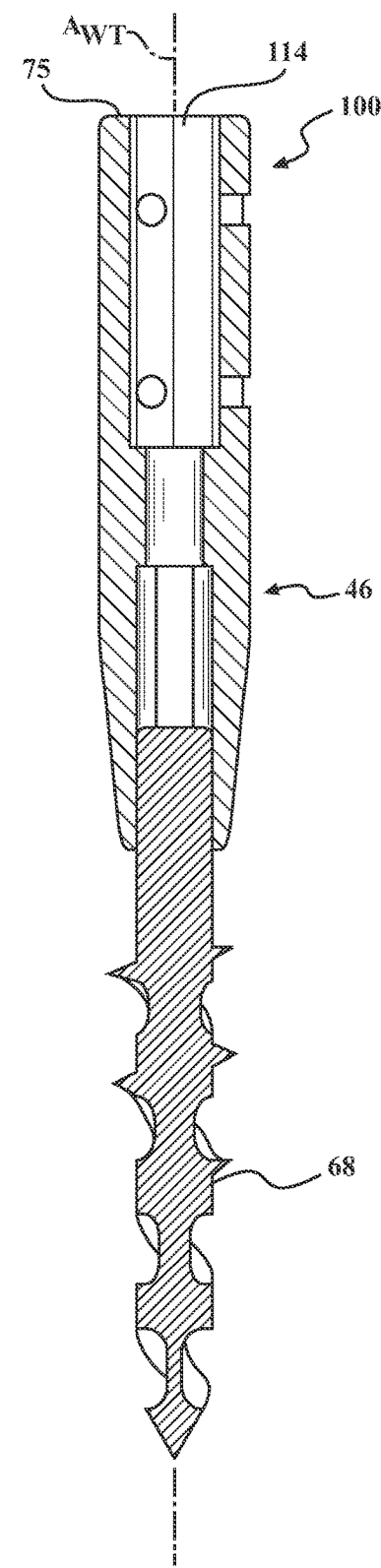
FIG. 14 is a cross sectional view of the working tool of FIG. 13 taken along section lines 14-14.

Referring to FIGS. 12-14, the tracking device 102 in accordance with another exemplary embodiment is shown with the tracking device 102 adapted to be removably coupled to the tap marker 100. The tap marker 100 may be considered one of the working tools 46 of the tool assembly 40, 41. The tap marker 100 includes the working section 68 for securing the tap marker 100 within the bony anatomy B, and the proximal shaft portion 70 extending proximally from the working section 68. In one non-limiting example, the proximal shaft portion 70 includes a barrel section with a length of 15 millimeters and an outer diameter of 5.55 millimeters configured to snugly and slidably move within the elongate sleeve 72, 160 previously described. In another example, the proximal shaft portion 70 includes a barrel section with a length of 21 millimeters and an outer diameter of 6.05 millimeters configured for crossover at the L5-S1 intervertebral space. Non-limiting examples of the working section 68 of the tap marker 100 include awl taps and taps sold under the tradename Serrato™ by Stryker Corporation (Kalamazoo, Mich.), with the outer diameter of the working section 68 within the range of approximately 4.0 millimeters to 5.5 millimeters.

The working tool 46 may define an axis $A_{WT}$ extending longitudinally through the proximal shaft portion 70 and the working section 68. The working section 68 may be self-tapping, self-drilling, and/or of any other suitable construction for penetrating and being secured within the bony anatomy B. The proximal shaft portion 70 includes a coupling feature 114 at the proximal end 75 for removably coupling with the tracking device 102. FIGS. 13 and 14 show a star-shaped recess within the proximal shaft 75 defining the coupling feature 114. The coupling feature 114 removably receives the tracking device 102 and prevents rotation of the working tool 46 relative to a portion of the tracking device 102 in a manner to be described. It is also understood that the coupling feature 114 is adapted to removably receive the input device 44 (see FIG. 3) or the drive coupler 42a, 42b for placement of the tap marker 100 within the bony anatomy B. In other words, the drive coupler 42a, 42b may have an alternative distal end with a star shape to engage the coupling feature 114 of the tap marker 100 and drive the tap marker 100 into the bony anatomy, similar to the way in which the working tool 46 shown in FIGS. 8A-8C is driven into the bony anatomy B.

The tracking device 102 of FIG. 12 includes the markers 108 rigidly coupled to the shaft 112 as previously described. The shaft 112 generally defines the axis $A_{TD}$ extending longitudinally through the tracking device 102. The tracking device 102 of the exemplary embodiment of FIG. 12 further includes a ratcheting mechanism 116 for providing unidirectional rotation of the tracking device 102 relative to the working tool 46 about the longitudinal axis $A_{WT}$ of the working tool 46. The ratcheting mechanism 116 may be positioned at or near the distal end of the shaft 112. In another embodiment, the ratcheting mechanism 116 is integrated into the proximal shaft portion 70 of the working tool 46. In certain embodiments, the tracking device 102 may include a post member 118 having a distal end 120 to be removably coupled to the coupling feature 114 of the working tool 46. FIG. 12 shows the post member 118 as an elongate structure with the distal end 120 including a star-shaped protrusion adapted to matingly engage the star-shaped recess forming the coupling feature 114 of the working tool 46. The post member 118 is rotatably fixed relative to the working tool 46 when coupled to one another. The post member 118 includes a proximal end 122 opposite the distal end 120 with the proximal end 122 coupled to the tracking device 102. Further, the post member 118 is oriented along the longitudinal axis $A_{TD}$ of the tracking device 102. The ratcheting mechanism 116 is generally positioned at the interface between the proximal end 122 of the post member 118 and the distal end of the shaft 112. As a result, the ratcheting device 116 provides for unidirectional rotation of the shaft 112 and the markers 108 relative to the post member 118. The post member 118 may engage the tap marker 100 so that the proximal end 122 of the post member 118 protrudes out of the incision in the patient to be easily accessed by the surgeon. In this way, multiple tap markers 100 may be placed in the patient's spine, with the post members 118 extending out to identify general locations of the tap markers 100.

Figure 15A:
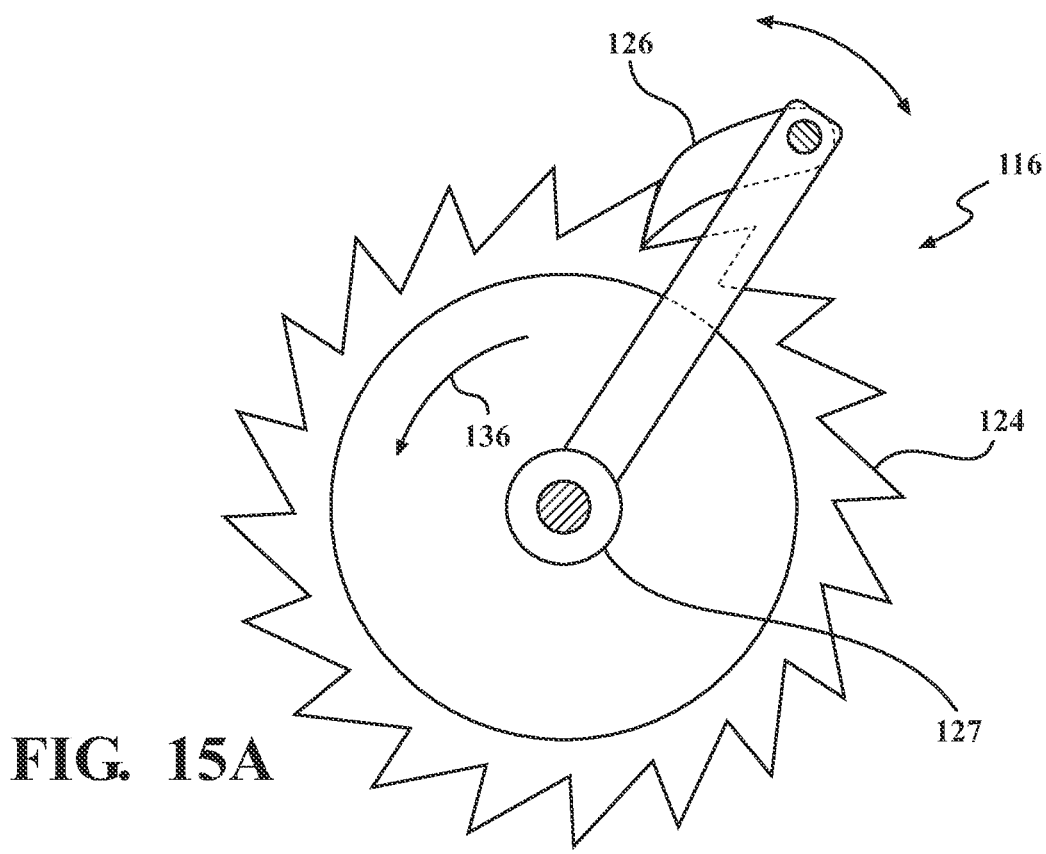
FIG. 15A is a schematic representation of a ratcheting mechanism.
Figure 15B:
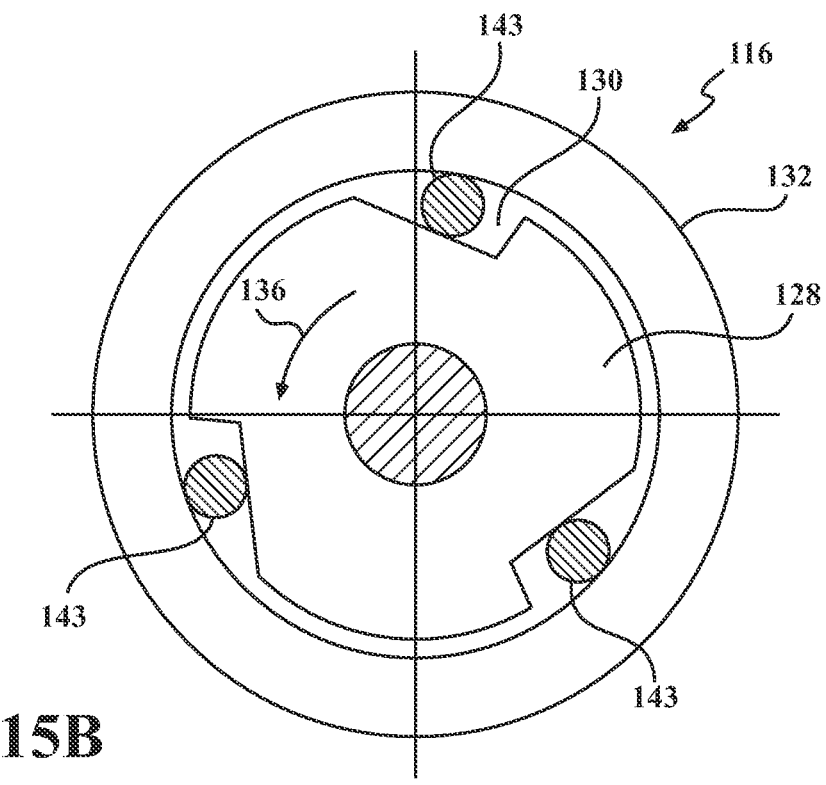
FIG. 15B is a schematic representation of another ratcheting mechanism.

FIGS. 15A and 15B are schematic illustrations of two exemplary embodiments of the ratcheting mechanism 116. The ratcheting mechanism 116 of FIG. 15A includes a driver wheel 124 and a pawl 126 coupled to a driven wheel 127. The ratcheting mechanism 116 of FIG. 15B includes a driver wheel 128 having recesses 130, and a driven wheel 132. Rolling elements 143 are positioned intermediate the driver and driven wheels 128, 132 and within the recesses 130. The ratcheting mechanism of FIG. 15B may be considered an overrunning clutch device. In each of the exemplary embodiments of the ratcheting mechanism 116, rotation of the driver wheels 124, 128 in a first direction (arrow 136) does not result in corresponding rotation of the driven wheels 127, 132. Rotation of the driver wheels 124, 128 in a second direction opposite the first direction results in corresponding rotation of the driven wheels 127, 132 based on the operation of the ratcheting mechanism 116. In some embodiments, the driver wheels 124, 128 are fixed to one portion of the tracking device 102 that is rotated by the user, while the driven wheels 127, 132 form another portion of the tracking device 102 that engages the post 118, or directly engages the tap marker 100 or other working tool 46. Other constructions of imparting unidirectional rotation between two structures may be implemented into the system of the present disclosure.

Figure 16:
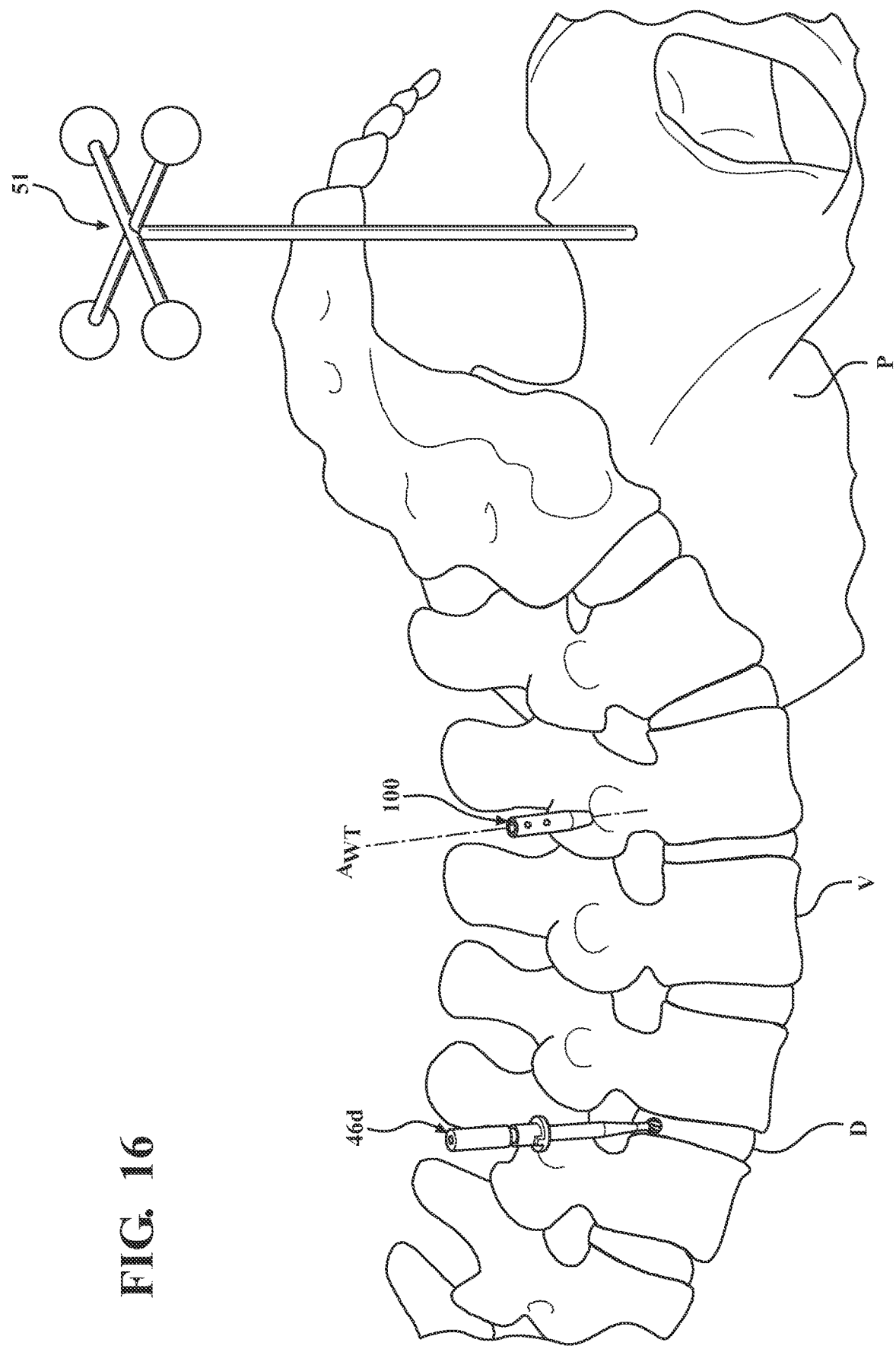
FIG. 16 is a perspective view of the spine with the working tool of FIG. 13 secured within a pedicle of a vertebra and with the working tool of FIG. 6A manipulating tissue remote from the secured working tool.

Exemplary operation of a system 134 with the tool assembly 40, 41 including the tracking device 102 with the ratcheting mechanism 116 will now be described with reference to FIGS. 16 and 17. The system 134 includes the navigation system 32 with the localizer 34. The tool assembly 40, 41 (FIG. 3) includes the tap marker 100 with the working section 68 for penetrating the vertebra V of interest. FIG. 16 shows the tap marker 100 secured within the pedicle of the vertebra V. The tap marker 100 includes the longitudinal axis $A_{WT}$ previously described. FIGS. 16 and 17 show another tracking device 51 rigidly secured to the pelvis P of the patient with the tracking device 51 detectable by the localizer 34 of the navigation system 32. The positions of the vertebra have been previously registered using known registration techniques.

In certain embodiments, tissue remote from the tap marker 100 is manipulated while the tap marker 100 remains secured within the vertebra V. FIG. 16 schematically represents the working tool 46 (i.e., the bur 46d of FIG. 3) resecting at least a portion of an intervertebral disc D while the tap marker 100 remains secured within the vertebra V. While one tap marker 100 is shown in FIG. 16, it is understood that each vertebra may include more than one tap marker (i.e. bipedicular), and more than one vertebrae may include tap marker(s). The removal of the intervertebral disc D may cause movement of the vertebrae, including the vertebra V of interest. Further, often a cage (also known as an artificial disc) is placed within the intervertebral disc space no longer containing the disc material. The cage may be adjustable in order to selectively provide the desired disc spacing to relieve neural compression, achieve proper lordosis, and the like. The placement of the cage within the intervertebral disc may also cause movement of the vertebrae, including the vertebra V of interest. While the registered position of the pelvis P is known precisely due to the tracked position by the localizer 34, approximations of shifted positions of the vertebrae may be insufficient for subsequent pedicle screw placement guided with the robotic arm 36.

As a result, relocalizing or reregistering the vertebra V includes updating the position of the vertebra V after the shifting has occurred. The updated pose information is provided to the robotic controller 52 prior to placement of the pedicle screw. To relocalize the bony anatomy, the tracking device 102 is coupled to the tap marker 100 with the tap marker 100 secured within the vertebra V. In manners previously described, the post member 118 of the tracking device 102 is coupled to the coupling feature 114 of the tap marker 100, as generally represented in FIG. 17. The markers 108 of the tracking device 102 are detectable by the localizer 34 of the navigation system 32, and the updated pose of the tap marker 100 may be determined and provided to the robotic controller 52. It should be understood that the user may operate software on one of the displays 35 (FIG. 1) to indicate to the navigation system 32 that the pose of the bony anatomy is being updated. The updated pose of the tap marker 100 compensates for any movement of the vertebra V during manipulation of the intervertebral disc D and cage placement. The tracking device 102 is subsequently removed, after which the remaining step(s) of the surgical procedure may be performed.

As previously mentioned, the markers 108 are often detected by the localizer 34 with optical techniques, and consequently it is often necessary to establish line-of-sight between the localizer 34 and the markers 108. Depending on the initial orientation in which the tracking device 102 is coupled to the tap marker 100, the requisite line-of-sight between the localizer 34 and the markers 108 may not initially be present. The tool assembly 40, 41 advantageously provides for rotation of the tracking device 102 relative to the tap marker 100 with the tap marker 100 secured within the vertebra V in order to establish or reestablish the line-of-sight between the localizer 34 and the markers 108. Moreover, the sweeping motion of the markers 108 during rotation of the tracking device 102 relative to the tap marker 100 may facilitate improved determinations of the pose of the tap marker 100 within the vertebra V.

With continued reference to FIG. 17, once the tracking device 102 is coupled to the tap marker 100, the markers 108 are movable in one degree of freedom relative to the tap marker 100. The one degree of freedom is rotation about the collinear longitudinal axes $A_{TD}$, $A_{WT}$ of the tracking device 102 and the tap marker 100. The tracking device 102, owing to its shape and connection to the tap marker 100 (alone or via the post member 118), is otherwise constrained from any movement, except that the tracking device 102 and/or post member 118 are removable from the tap marker 100 via movement along the longitudinal axis $A_{WT}$. However, it is understood that this movement is temporarily constrained due to gravity holding the tracking device 102 on the tap marker 100. In other embodiments, detent mechanisms or other coupling mechanisms may better constrain any longitudinal movement of the tracking device 102. Thus, in the absence of the user intentionally moving the tracking device 102 in the longitudinal direction relative to the tap marker 100 to remove the tracking device 102, the markers 108 may be otherwise movable in a singular degree of freedom relative to the tap marker 100.

With the tracking device 102 coupled to the tap marker 100, the tracking device 102 is rotated in the first direction (the arrow 136 in FIG. 17). Handles 138 rigidly coupled to the shaft 112 of the tracking device 102 may be grasped by the user to rotate the tracking device 102. The tracking device 102 is rotated until the markers 108 are generally oriented towards the localizer 34. An indicator (not shown) on the localizer 34 and/or software displayed on one of the displays 35 (FIG. 1) may alert the user that the markers 108 are being detected by the localizer 34. Because the markers 108 of the tracking device 102 are at a known, fixed distance from the shaft 112 (and the longitudinal axis $A_{TD}$), the markers 108 being moved in a sweeping manner in the singular degree of freedom relative to the tap marker 100 permits the software of the navigation system 32 to quickly determine the longitudinal axes $A_{TD}$, $A_{WT}$ of the tracking device 102 and the pose of the tap marker 100.

In certain embodiments, the ratcheting mechanism 116 facilitates orienting the markers 108 without rotation of the working tool 46, such as in response to rotation of the tracking device 102 about the longitudinal axis $A_{WT}$ of the working tool 46 in the first direction. In the exemplary embodiment illustrated in FIG. 17, the ratcheting mechanism 116 provides for the tracking device 102 to rotate freely in the first direction (arrow 136) without corresponding rotation of the tap marker 100 secured within the vertebra V. Furthermore, the ratcheting mechanism 116 is adapted to facilitate removal of working tool 46 from the bony anatomy B in response to rotation of the tracking device about the longitudinal axis $A_{WT}$ in a second direction opposite the first direction. In other words, the unidirectional rotation provided by the ratcheting mechanism 116 causes the markers 108 to rotate relative to the tap marker 100 when the tracking device 102 is rotated about the longitudinal axis $A_{WT}$ of the tap marker 100 in the first direction, and facilitate withdrawal of the tap marker 100 from the vertebra V when the tracking device 102 is rotated about the longitudinal axis $A_{WT}$ of the tap marker 100 in the second direction opposite the first direction. Often during the spinal fusion procedure, it is desirable to remove the tap marker 100 from the vertebra V immediately following relocalization so as to place the pedicle screw within the pedicle of the vertebra V. Thus, at the appropriate point in the surgical procedure with the tap marker 100 positioned within the vertebra V, the tracking device 102 is coupled to the tap marker 100, rotated in the direction to orient the markers 108 in a manner to be sensed by the localizer 34 of the navigation system 32, then rotated in the second direction to withdraw the tap marker 100 from the vertebra V. The handles 138 rigidly extending outwardly from the shaft 112 of the tracking device 102 may be grasped by the user to rotate the tracking device 102 in one of the first and second directions.

Figure 18:
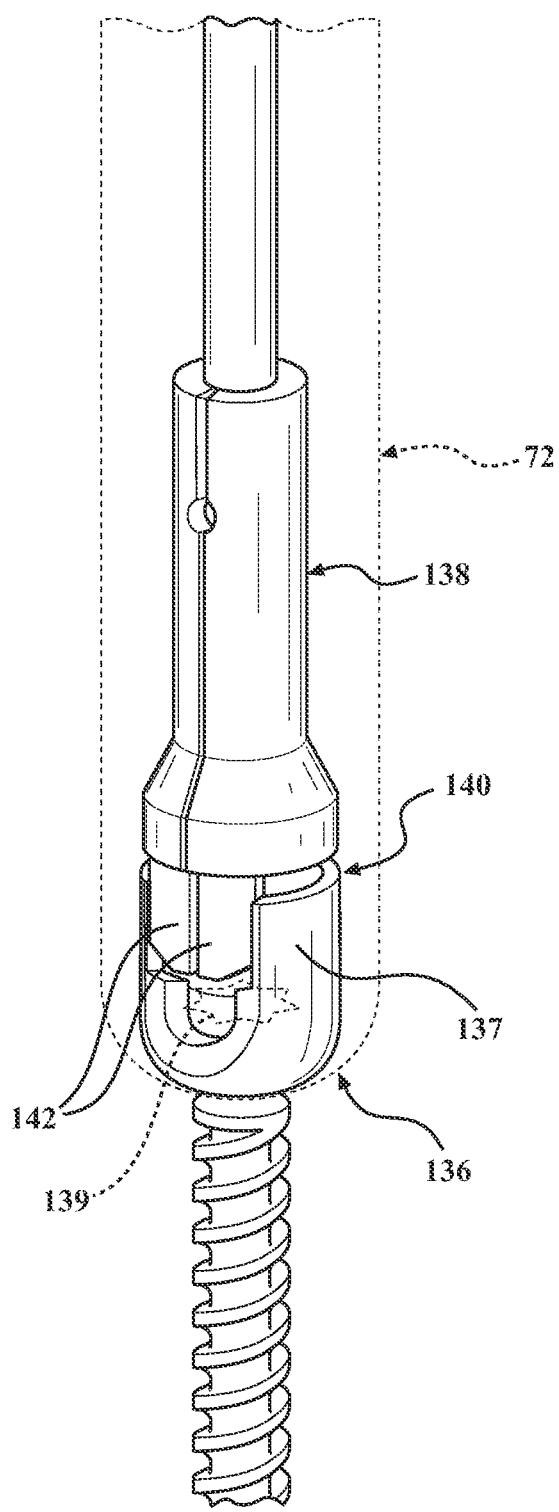
FIG. 18 is a perspective view of a working tool.

It is to be understood that during the aforementioned step(s) of relocalizing the bony anatomy using the tracking device 102, the elongate sleeve 72 may have remained positioned within the overlying soft tissue T to provide the working channel to the working tool 46. Further, the removal of the working tool 46 from within the bony anatomy as previously described may include the elongate sleeve 72 remaining positioned within the overlying soft tissue T to provide the working channel to the surgical site. More specifically, the elongate sleeve 72 may remain so positioned to provide the working channel to a void in the bony anatomy formed as a result of the removed working tool 46. In the context of the spinal fusion procedure, the void 154 may be within the pedicle with the void providing a pilot hole (threaded or unthreaded) for a pedicle screw (see FIGS. 22 and 23). Referring to FIG. 18, a pedicle screw 136 in accordance with one exemplary embodiment is shown. The pedicle screw 136 is removably coupled to a screwdriver 138. The pedicle screw 136 and the screwdriver 138 may collectively comprise one of the working tools 46 of the tool assembly 40, 41 of the present disclosure. In other words, the proximal shaft portion 70 of the screwdriver 138 may be removably coupled to the drive coupler 42a, 42b previously described with the drive coupler 42a, 42b transferring torque from the input device 44 to the screwdriver 138.

The pedicle screw 136 may be monoaxial, polyaxial, biased, cannulated, and/or non-cannulated, among other suitable constructions. In one example, the screw 136 is the ES2 percutaneous pedicle screw system manufactured by Stryker Corporation (Kalamazoo, Mich.). In another example, the screw 136 is the Serrato™ pedicle screw manufactured by Stryker Corporation (Kalamazoo, Mich.). The pedicle screw 136 may include a coupling feature 140 for coupling the pedicle screw 136 to the driver 138. For example, the coupling feature 140 of FIG. 18 includes a polyaxial head, such as a tulip 137 that utilizes compression to maintain engagement between the screw 136 and the driver 138. The tulip 137 may include at least two arcuate portions extending axially with notches between the arcuate portions. The driver 138 includes a pair of compressible tongues 142. As the tongues 142 engage the notches between the arcuate portions, the tongues 142 are compressed together owing to a slot through the tongues that extends part way up a shaft of the driver 138. In other words, the tongues 142 deflect inwardly slightly during insertion of the driver 138 into the tulip 137. The driver 138 may further include a cruciform or star-shaped driver head 139 (shown in hidden lines in FIG. 18) that engages a mating recess in the pedicle screw 136 to drive the pedicle screw 136 into bone. The driver 138 and the pedicle screw 136 thus have coupling features (e.g., the tongues 142 and tulip 137) to hold the pedicle screw 136 to the driver 138 and a driver head that transmits torque to the pedicle screw 136 to insert the pedicle screw 136. Any other suitable construction of drivers 138 may be used to engage any variety of screws. Other forms of coupling features are also contemplated.

As shown in FIG. 18, the driver 138 is suitably sized to move through the elongate sleeve 72 positioned within the overlying tissue, and ensure unobstructed axial and rotational motion for screw insertion. Once the screw 136 is fully seated, the driver 138 is disengaged from the coupling feature 140 of the screw 136. Subsequent to the placement of the screw 136 within the pedicle of the vertebra V, the elongate sleeve 72 may be removed from the overlying tissue. The distal end 78 of elongate sleeve 72, opened by the moveable feature 80 in manners previously described, is sized to be slidably removed over the screw 136. In certain embodiments, the elongate sleeve 72 is disposable and is discarded. Alternatively, the elongate sleeve 72 may remain positioned within the overlying tissue for as long as the surgeon requires visualization of the surgical site.

Figure 19:
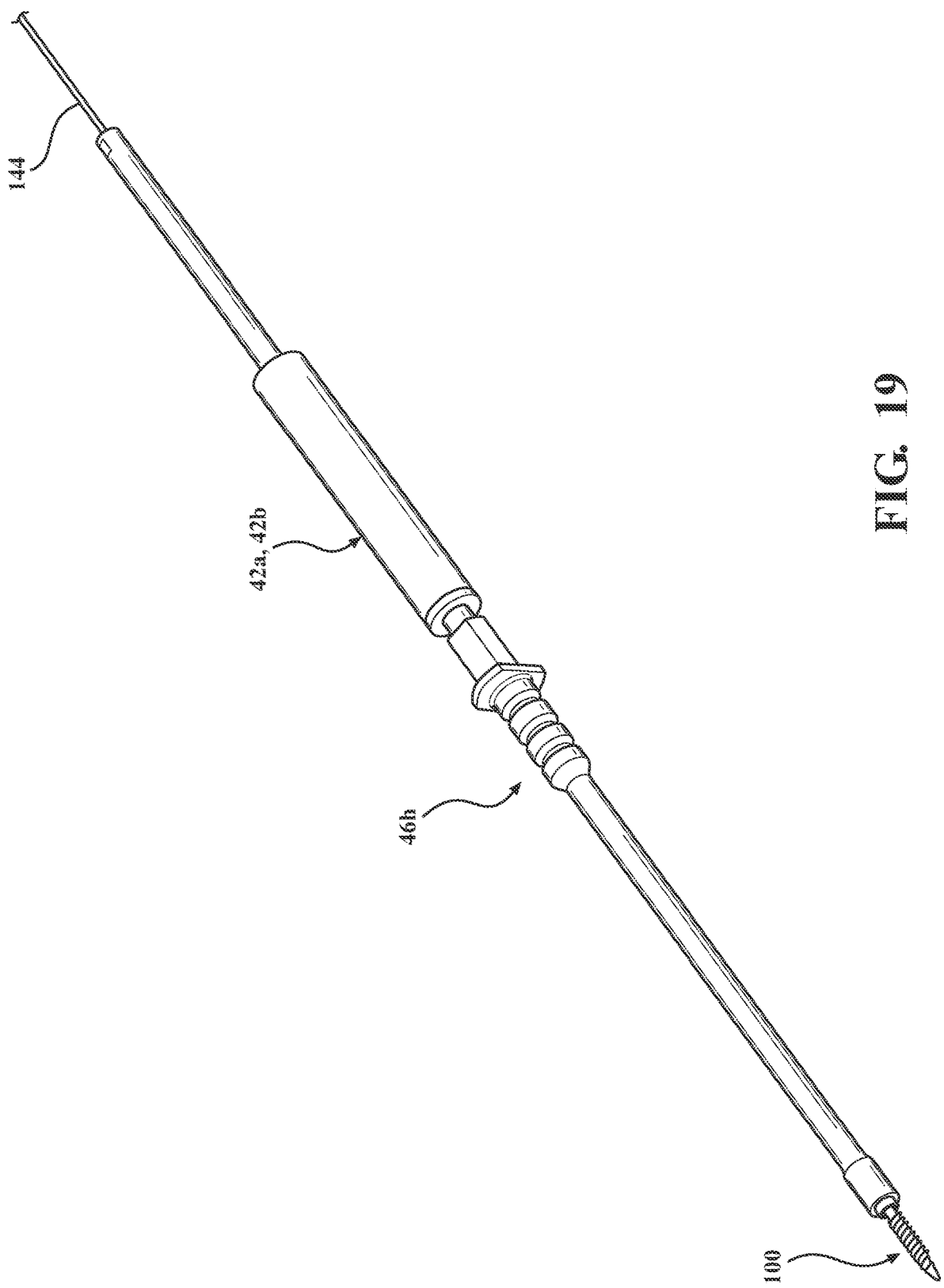
FIG. 19 is a perspective view of a tool assembly with a working tool coupled to the drive coupler of FIG. 4A. An elongated wire extends through the tool assembly.
Figure 20:
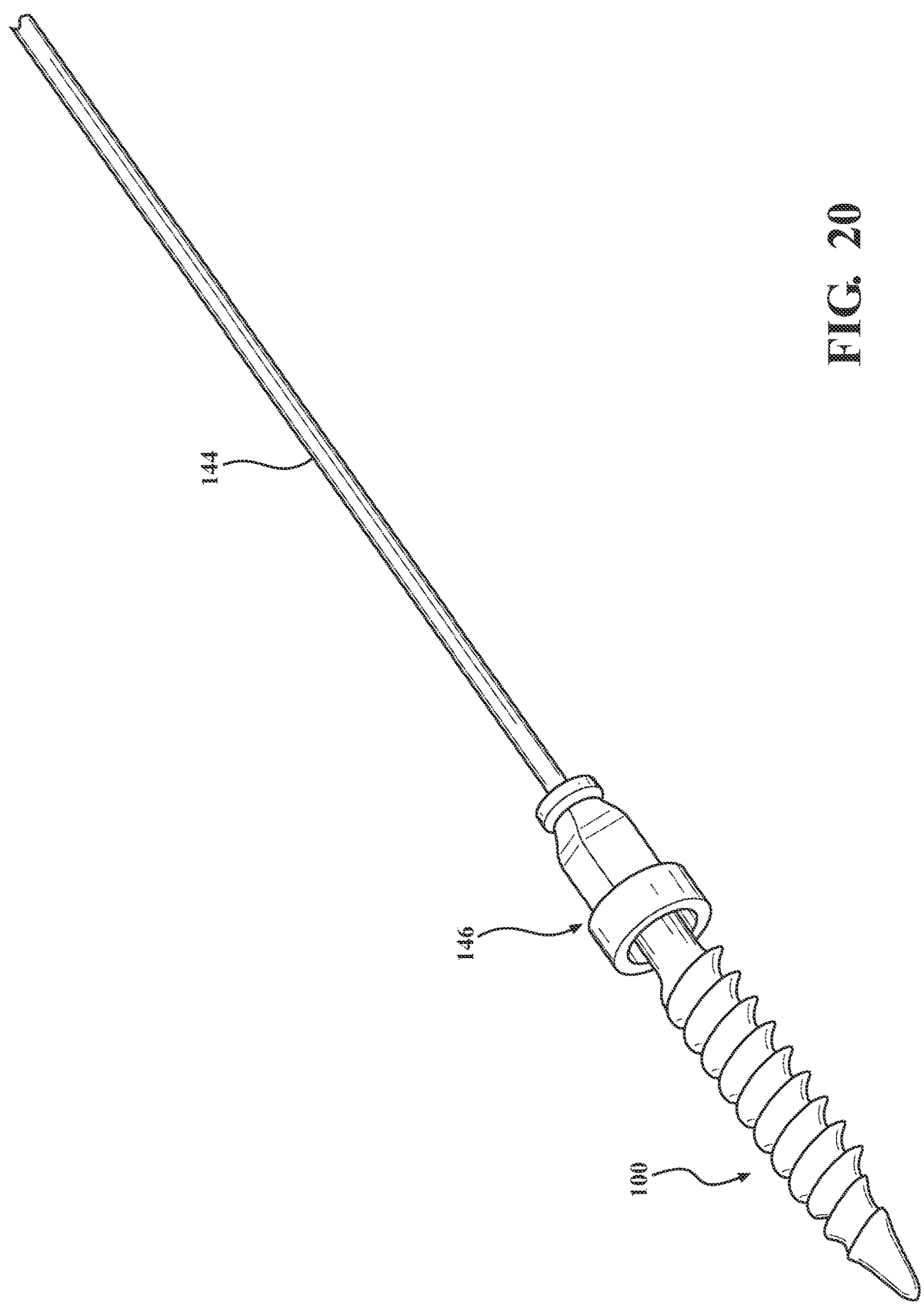
FIG. 20 is a perspective view of the working tool of FIG. 19 with the elongated wire extending through working tool.

The robotic arm 36 may accurately place the tap marker 100 and/or the pedicle screw 136 within the bony anatomy without the need for a guidewire (e.g., Kirschner wire). Further, with the tracking device 102 adapted to quickly and effectively couple and decouple from the tap marker 100 for relocalization during the surgical procedure as desired, the conventional need for a guidewire (i.e., to guide a cannulated pedicle screw to a desired location) is not as apparent. Yet in certain embodiments of the tool assembly 40, 41 and system 134 of the present disclosure, an elongate flexible element, such as guidewire 144, may be integrated as shown in FIGS. 19 and 20. For example, the guidewire 144 may be secured within the bony anatomy with the tap marker 100 being cannulated and disposed over the guidewire 144 and advanced into the bony anatomy. In another exemplary embodiment, the guidewire 144 is rigidly connected to the tap marker 100. FIG. 20 shows the guidewire 144 coupled to a proximal head 146 of the tap marker 100. The guidewire 144 may be a wire or a woven cord coupled to the proximal head 146 of the tap marker 100, such as by threading, clamping, or other suitable joining means. With only the proximal head 146 of the tap marker 100 often being above the bony anatomy, the tap marker 100 could become submerged in the overlying soft tissue as the resiliency of the tissue tends to close the incision. In other words, in certain embodiments the tap marker 100 may include a length between a tip of the working section 68 and the proximal end (see FIGS. 13 and 14) insufficient to extend above the soft tissue when the working section 68 is secured within the bony anatomy. The guidewire 144 has suitable length so as to extend from the proximal head 146 of the tap marker 100 above or beyond the surface of the tissue. The presence of guidewire 144 exiting the tissue provides a visual indicator to the surgeon that the tap marker 100 has been placed. The guidewire 144 has suitable flexibility so as to be moved away from the surgical site to limit obstruction.

With continued reference to FIG. 19, the working tool 46 (i.e., the tap inserter 46*h* of FIG. 3) is coupled to the drive coupler 42*a*, 42*b* of the tool assembly 40, 41. In the present embodiment, the drive coupler 42*a*, 42*b* and the tap inserter 46*h* are cannulated so as to receive the guidewire 144 as the tap inserter 46*h* is rotated to implant the tap marker 100 within the bony anatomy. It is to be understood that in certain embodiments, the tracking device 102 (see FIG. 17) may be cannulated so as to receive the guidewire 144 as the tracking device 102 is coupled to the tap marker 100 for relocalization as previously described. The guidewire 144 guides the tracking device 102 into a coupling arrangement with the proximal shaft portion 70 of the tap marker 100.

Figure 21:
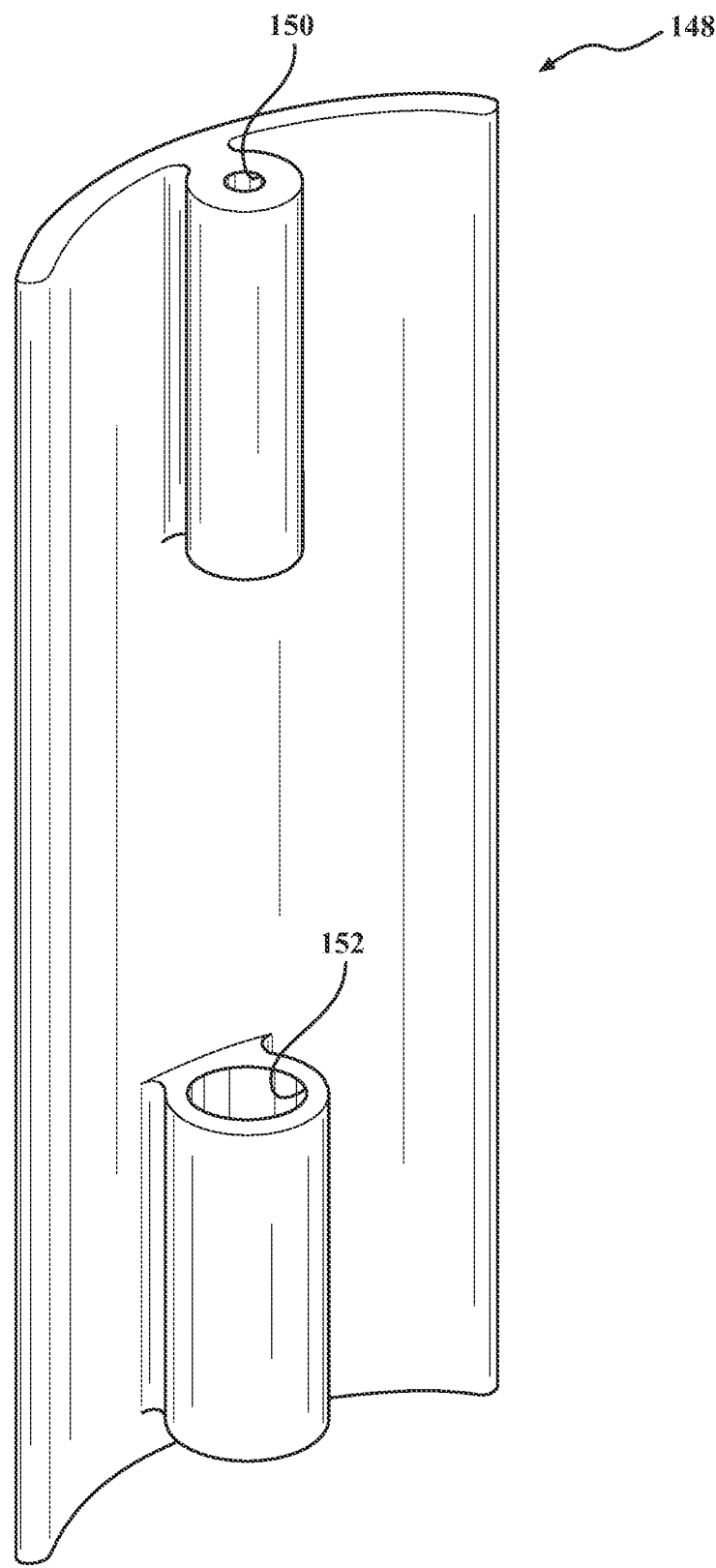
FIG. 21 is a perspective view of a retractor.

In certain embodiments, a retractor 148 may be slidably positioned over the guidewire 144 and within the overlying soft tissue to provide a working channel in the absence of the elongated sleeve 72. FIG. 21 shows an exemplary embodiment of the retractor 148 including an arcuate blade-like surface suitably sized for the incision into which the retractor 148 is to be placed. The arcuate shape urges the tissue on one side of the incision away from the tissue on the other side when the retractor 148 is positioned within the incision. The retractor 148 includes at least one aperture 150 generally dimensioned to receive the guidewire 144 of FIG. 20. With the tap marker 100 secured within the bony anatomy and the guidewire 144 extending from the surface of the overlying tissue, the aperture 150 of the retractor 148 may be slidably moved along the guidewire 144 and into the incision. The retractor 148 includes a length greater than a thickness of the overlying tissue such that at least a portion of the retractor 148 extends from the surface of the overlying tissue. In certain embodiments, the retractor 148 includes a second aperture 152 generally coaxial with the first aperture 150. The second aperture 152 is generally dimensioned to receive the guidewire 144. In one example, the second aperture 152 is larger than the first aperture 150 with the second aperture 152 dimensioned to receive a portion of the proximal head 146 of the tap marker 100. Referring to FIG. 20, the retractor 148 of FIG. 21 is slidably moved along the guidewire 144 with the second aperture 152 distal to the first aperture 150. As the retractor 148 approaches the tap marker 100 secured within the underlying bony anatomy, the proximal head 146 of the tap maker 100 is received within the second aperture 152 to provide lateral support to the retractor 148 positioned within the overlying tissue. It is understood that more than one retractor 148 may be provided. For example, two retractors 148 may be oriented opposite to one another and slidably moved along the guidewire 144 and into the incision. Each of the retractors 148 oriented opposite to one another provides a generally oval-shaped cavity within the overlying tissue for improved visibility of and access to the surgical site. It is to be further understood that the retractor 148 may assume any number of various geometries to accommodate the specific aspects of the surgical procedure and/or specific anatomies or incisions.

As described throughout the present disclosure, in many embodiments the tool assembly 40, 41 and system 134 are adapted to be implemented with the robotic system 30 including the navigation system 32 and the robotic arm 36. An exemplary operation of the robotic system 30 will now be described with reference to FIGS. 1 and 22 and 23 in which the robotic system 30 is used to place the pedicle screw 136 into the vertebra V. FIG. 1 shows the robotic system 30 with the navigation system 32 including the localizer 34 and a tracking device 49 coupled to the robotic arm 36, the displays 35, and the robotic manipulator (e.g., the robotic arm 36 mounted to the base 38). The tool assembly 40, 41 for use in performing the spine procedure is coupled to a distal end of the robotic arm 36. The navigation system 32 may include one or more of the tracking devices 49, 50, 51, 102 as described throughout the present disclosure, and additional tracking devices may be utilized. Conventional techniques (e.g., optical, EM, RF technology, etc.) may be employed to correlate the pose of the markers 108 to vertebra V of interest. Ultimately, the localizer 34 and the trackers enable the determination of the pose of the tool assembly 40, 41 and the vertebra V so the navigation system 32 knows the relative relationship between the tool assembly 40, 41 and the patient's anatomy. One such navigation system is shown in U.S. Pat. No. 9,008,757, hereby incorporated by reference. It may also be desired to track the patient's skin surface to ensure that the tool assembly 40, 41 does not inadvertently contact or penetrate the patient's skin outside of any desired incision boundaries. For this purpose, a skin marker array (not shown), such as active or passive markers with adhesive backing may be attached to the patient's skin to define a boundary associated with the patient's skin. One suitable skin marker array is the SpineMask® tracker manufactured by Stryker Leibinger GmbH & Co. KG, Bötzinger StraBe 41, D-79111 Freiburg, Germany. The digitizing probe 106 could also be used to map the skin surface and/or incision.

Prior to the start of the surgical procedure, additional data is provided to the navigation system 32. Pre-operative imaging and/or intra-operative imaging may be employed to visualize the patient's spine. An imaging device may be used to take the preoperative images of the anatomy; e.g., X-rays, computed tomography (CT) scans, or magnetic resonance imaging (MRI) scans taken before surgery. The surgeon plans where to place the pedicle screw 136 with respect to the images and/or with respect to a three dimensional (3D) model or other representation created from the images. Planning includes determining the pose of each pedicle screw 136 with respect to the vertebra V in which they are being placed, e.g., by identifying the desired pose in the images and/or the 3D model. This may include creating or positioning a separate 3D model of the pedicle screw 136 with respect to the 3D model of the patient's anatomy. Once the plan is set, then the plan is transferred to the robotic system 30 for execution. The imaging device, or another imaging device (e.g., a C-arm), may also be used to take the intra-operative images to aid with determining the actual position of the tool assembly 40, 41 relative to the desired orientation of the pedicle screw 136 being placed in the vertebra V. Further, the additional data may comprise calibration data, such as geometric data relating positions and/or orientations of the trackers to the working section 68 of the tool assembly 40, 41, and/or registration data associating the trackers to the patient's anatomy or 3D models thereof.

The robotic system 30 evaluates the desired pose of the pedicle screw 136 and creates virtual boundaries (e.g., haptic objects), pre-defined tool paths, and/or other autonomous movement instructions, that correspond to the desired pose of the pedicle screw 136 to control movement of the robotic arm 36 for several aspects of the surgical procedure to be described. In operation, for certain surgical tasks, the user manually manipulates (e.g., moves or causes the movement of) the robotic arm 36 to manipulate the tool assembly 40, 41 to perform the surgical procedure on the patient, such as drilling, cutting, reaming, implant installation, and the like. As the surgeon manipulates the tool assembly 40, 41, the navigation system 32 tracks the location of the tool assembly 40, 41 and/or the robotic arm 36 and provides haptic feedback (e.g., force feedback) to the user to limit the user's ability to move (or cause movement of) the tool assembly 40, 41 beyond one or more predefined virtual boundaries that is registered (or mapped) to the patient's anatomy, which results in highly accurate and repeatable drilling, cutting, reaming, and/or implant placement. In one embodiment, the robotic arm 36 operates in a passive manner and provides haptic feedback when the surgeon attempts to move the tool assembly 40, 41 beyond the virtual boundary. The haptic feedback is generated by one or more actuators (e.g., joint motors) in the robotic arm 36 and transmitted to the user via a flexible transmission, such as a cable drive transmission. When the robotic arm 36 is not providing haptic feedback, the robotic arm 36 is freely moveable by the user. In other embodiments, like that shown in U.S. Pat. No. 9,566,122, which is hereby incorporated by reference, the robotic arm 36 is manipulated by the user in a similar manner, but the robotic arm 36 operates in an active manner. For instance, the user applies force to the tool assembly 40, 41, which is measured by a force/torque sensor, and the robotic arm 36 emulates the user's desired movement based on measurements from the force/torque sensor. For other surgical tasks, the robotic arm 36 operates autonomously. In further embodiments, a combination of manual and autonomous control is utilized. For example, a robotic system that employs both a manual mode in which a user applies force to the robotic arm 36 and/or tool assembly 40, 41 to cause movement of the robotic arm 36, and a semi-autonomous mode in which the user holds a pendant to control the robotic arm 36 to autonomously follow a tool path. The relative position of the working end of tool assembly 40, 41 to the vertebrae V may also be displayed on the displays 35 to allow the surgeon and staff to view the relative position of the tool assembly 40, 41 to the surgical site.

With the preoperative plan defined, the intraoperative representation of the vertebrae V registered to the preoperative representation, and the navigation system 32 tracking the tracking devices, an incision is made within the overlying tissue T. In one exemplary embodiment, the robotic arm 36 may autonomously position the tool assembly 40, 41 along the predefined trajectory above the vertebra V. Such autonomous positioning may be initiated by the user (e.g., by providing input to the control system) to start the movement. Once the tool assembly 40, 41 is in the desired pose, the robotic system 30 may effectively hold the longitudinal axis $A_{WT}$ of the working tool 46 on the desired trajectory (e.g., via a line haptic object LH) by tracking movement of the patient and autonomously adjusting the robotic arm 36 as needed. The working tool 46 (e.g., the scalpel holder 46a, the scalpel 46b, and the like) is now coupled to the drive coupler 42a, 42b. As previously described, the drive coupler 42a, 42b is coupled to the input device 44 with a position maintained by the robotic arm 36 of the robotic system 30. Thus, with the scalpel holder 46a or the scalpel 46b coupled to the robotic arm 36, the tool assembly 40, 41 can be advanced such that the working tool 46 incises the overlying tissue T with haptic guidance. Virtual boundaries may be used when creating the incision to constrain the user's movement with respect to a desired incision in the tissue. In one example, the digitizing probe 106 can be used to touch the desired incision location and create the associated boundary/haptic object. The haptic objects can be defined in various ways to establish the haptic feedback to guide making of the incision, for example, a V-shaped incision. In another example, the surgeon performs a stab incision in an 'X' or cross formation. The haptic objects can be defined based on a width of the skin incision tool, a desired length of the skin incision, and/or a desired depth of the incision. A desired incision depth can also be controlled by the user. In other exemplary embodiments, a guide tube (not shown) may be coupled to the robotic arm 36 with a conventional scalpel inserted through a lumen extending through the guide tube. The guide tube constrains the conventional scalpel along the predefined trajectory. A mechanical stop can be used to prevent the skin incision tool 80 from sliding through the guide tube of the end effector beyond a predetermined point.

Due to the advantageous features of the tool assembly 40, 41 previously described, the working tool 46 may be decoupled from the drive coupler 42a, 42b, and another working tool 46 may be coupled to drive coupler 42a, 42b without decoupling the drive coupler 42a, 42b from the input device 44. In the present embodiment of the robot-assisted surgical procedure, the working tool 46a, 46b is decoupled from the drive coupler 42a, 42b, and the dilator probe 46g (see FIG. 3) is coupled to the drive coupler 42a, 42b. The dilator probe 46g is advanced within the incision and through the overlying tissue T to expand the incision. The dilator probe 46g is constrained by the robotic arm 36 to the desired trajectory. For example, the robotic system 30 may effectively hold the longitudinal axis $A_{WT}$ of the dilator probe 46g on the line haptic object LH by tracking movement of the patient and autonomously adjusting the robotic arm 36 as needed as the dilator probe 46g is advanced within the incision.

In certain embodiments, the input device 44 provides a torque to the drive coupler 42a, 42b to rotate the dilator probe 46g as it is advanced within the overlying tissue T. The rotation may be either unidirectional or bidirectional with oscillation to dilate the tissue. In the latter example, the bidirectional rotation oscillates the dilatator probe 46g as the dilatator probe 46g is advanced into the overlying tissue T. Oscillation of the dilator probe 46g may be such that the dilator probe 46g rotates less than ninety degrees in either direction, less than forty-five degrees in either direction, less than twenty degrees in either direction, or less than ten degrees in either direction. The oscillation of the dilator probe 46g may be provided at any suitable frequency, such as 0.1 Hertz (Hz), 1 Hz, 10 Hz, or more, in order to limit static friction between the dilator probe 46g and the tissue as it is advanced therein. The dilator probe 46g may be advanced within the overlying soft tissue until positioned, for example, one millimeter above the pedicle P of the vertebra V. The dilator probe 46g may be removed from within the overlying tissue T with the robotic arm 36 continuing to hold the longitudinal axis $A_{WT}$ of the dilator probe 46g on the line haptic object LH. Once it is determined (e.g., based on a position of the dilator probe 46g or the shape of the haptic object) that the working tool 46 is safely above the overlying tissue T, the robotic arm 36 may permit deviation of the working tool 46 from the line haptic object LH.

The tap marker 100 (see FIGS. 7 and 12) is coupled to the elongate sleeve 72. The tap marker 100 may be pre-assembled to the elongate sleeve 72 and contained within sterile packaging for use. For instance, the tap marker 100 may be positioned within the cavity 68 of the elongate sleeve 72 such that the complementary locating features 90, 92 are engaged. As previously mentioned, with the complementary locating features 90, 92 engaged, a length of the working tool 46 defined between a tip of the working section 68 and the proximal shaft portion 70 is the same or less than a length of the elongate sleeve 72 such that an entirety of the working tool 46 is selectively disposed within the elongate sleeve 72. This further helps to avoid inadvertent contact between the tap marker 100 and surgical staff. The dilatator probe 46g is decoupled from the drive coupler 42a, 42b, and the tap marker 100 (with the elongate sleeve 72) is removed from the packaging and coupled to the drive coupler 42a, 42b. The tool assembly 40, 41 (now with the tap marker 100) is advanced in the incision previously dilated with the robotic arm 36 constraining the tool assembly 40, 41 along the predefined trajectory. Less resistance from the overlying soft tissue T is encountered based on the dilation provided by the dilatator probe 46g. The input device 44 may provide a torque to the drive coupler 42a, 42b to rotate the tool assembly 40, 41 as the elongate sleeve 72 contacts overlying soft tissue T. The rotation may be either unidirectional and/or bidirectional with oscillation similar to that used with the dilator probe 46g.

With the pose of the tool assembly 40, 41 constrained by the robotic arm 36, the elongate sleeve 72 is positioned within the overlying soft tissue T to provide the working channel. For example, the robotic system 30 may hold the longitudinal axis $A_{WT}$ of the tool assembly 40, 41 on the line haptic object LII by tracking movement of the patient and autonomously adjusting the robotic arm 36 as needed as the elongate sleeve 72 is advanced within the overlying tissue T. Further, the movable feature 80 (see FIG. 7) prevents ingress of the overlying soft tissue T within the cavity 78 of the elongate sleeve 72 as the elongate sleeve 72 is advanced within the overlying soft tissue T. In one example, the distal end 76 of the elongate sleeve 72 is advanced until it contacts the pedicle P of the vertebra V. With the elongate sleeve 72 being maintained with the robotic arm 36 in a suitable position in contact with the pedicle P and on the predefined trajectory, the working tool 46 is moved distally relative to the elongate sleeve 72. As previously described with reference to FIGS. 8A-8C, the working tool 46 may be advanced distally while the axial position of the elongate sleeve 72 is maintained, and/or the elongate sleeve 72 may be retracted proximally while the axial position of the working tool 46 is maintained. With the distal movement of, in this case, the tap marker 100 relative to the elongate sleeve 72, the movable feature 80 opens and exposes the working section 68 of the tap marker 100 beyond the distal end 76 of the elongate sleeve 72. During this step the pose of the tool assembly 40, 41 is constrained or maintained by the robotic arm 36 in manners previously described.

Figure 22:
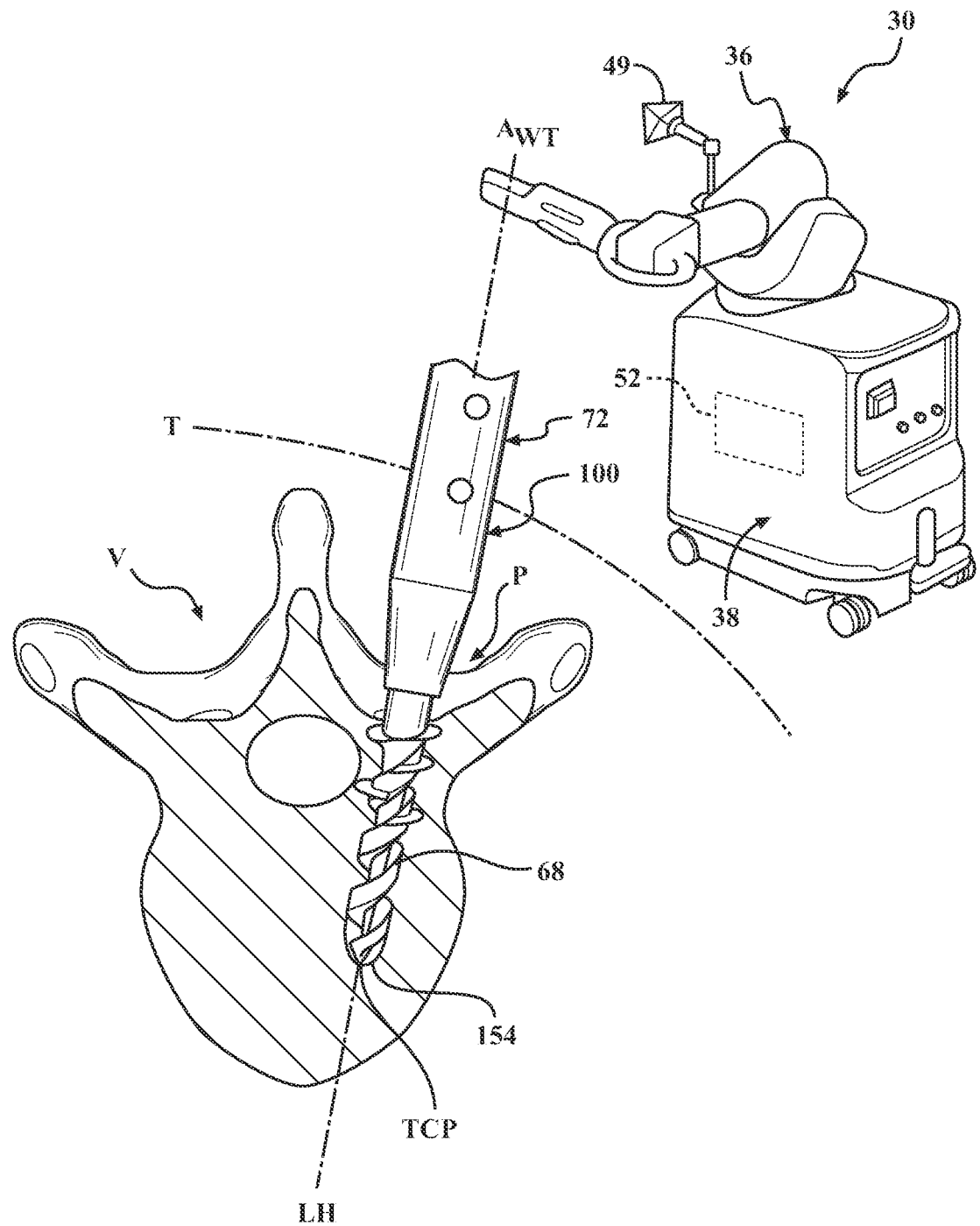
FIG. 22 is a schematic representation of a vertebra receiving the working tool of FIG. 12 guided with the robotic surgical system of FIG. 1.

The input device 44 is operated to cause the working tool 46 to manipulate the underlying bony anatomy along the predefined trajectory. In particular, the robotic arm 36 constrains the tool assembly 40, 41 as the input device 44 provides a torque to the drive coupler 42a, 42b to rotate the tap marker 100 as it is advanced within the pedicle P of the vertebra V along the predefined trajectory, as shown in FIG. 22. The robotic system 30 may autonomously aligns the longitudinal axis $A_{WT}$ of the tool assembly 40, 41 with the predefined trajectory (see FIG. 14). It is to be understood that a second tap marker 100 may be placed within the pedicle contralateral to the one shown in FIG. 22. It is to be further understood that the above steps may be repeated for additional vertebrae of the spine of the patient.

With the tap marker 100 secured within the pedicle P of the vertebra V along the predefined trajectory defined in the preoperative representation of the bony anatomy, the drive coupler 42a, 42b and the input device 44 are decoupled from the tap marker 100. Tissue remote from the tap marker 100 may be manipulated while the tap marker 100 remains secured within the pedicle P. As previously described and with reference to FIG. 16, still another working tool 46 (e.g., the bur 46d of FIG. 3) may be coupled to the drive coupler 42a, 42b and operated in a manner to resect at least a portion of one or more of the intervertebral discs D. An intervertebral cage may also be placed in a position adjacent or remote from the vertebra V of interest. It is understood that the discectomy and cage placement may be manually performed by the surgeon using techniques known in the surgical art.

As previously described in detail, movement between adjacent vertebrae (and relative to the pelvis being tracked with the tracking device 51) may occur during discectomy and cage placement. If the relative movement between the vertebra V of interest and the tracking device 51 is not detected, or if the vertebra V is not subsequently relocalized, positional error beyond acceptable levels may occur. In manners previously described, the tracking device 102 may be coupled to the tap marker 100. The tracking device 102 may be rotated about the longitudinal axis $A_{TD}$ collinear with both the longitudinal axis $A_{WT}$ of the tap marker 100 and the line haptic object LH. The collinear relationship between the lines, $A_{TD}$, $A_{WT}$, and line haptic object LH, facilitate efficient relocalization of the pose of the tap marker 100 (and the vertebra V). In particular, the tracking device 102 may be rotated about the longitudinal axis $A_{WT}$ in a first direction such that the markers 108 are sensed by the localizer 34 of the navigation system 32 (see FIG. 17). The pose of the vertebra V is updated based on the sensed position of the markers 108. The updated pose compensates for any movement of the vertebrae V during the discectomy and intervertebral cage placement. Subsequent to the optional step of relocalizing the vertebra V, the tap marker 100 is removed. In one exemplary embodiment previously described, the tracking device 102 is rotated in the second direction opposite the first direction with the ratcheting mechanism 116 of the tracking device 102 facilitating withdrawal of the tap marker 100. The removal of the tap marker 100 from the vertebra V provides the void 154 within the vertebra V, which in many cases is a pilot hole (in some cases with tapped threads) for the pedicle screw 136 to be placed.

The robotic controller 52 may realign the robotic arm 36 based on the step of relocalizing the vertebra V. A new line haptic object, with new starting point, target point, and exit point, could be created based on the original line haptic object LH, as transformed in a manner corresponding to the movement of the vertebrae V. Alternatively, the original line haptic object LH may be used if no appreciable movement has occurred. In either instance, the original or new line haptic object is an updated line haptic object LH. The pedicle screw 136 is attached to the driver 138 for placement in void 154. The updated line haptic object LH can be based on the driver 138 and/or the pedicle screw 136 so that the robotic arm 36 is controlled precisely to place that particular pedicle screw 136 to a desired depth in a manner that ultimately places the pedicle screw 136 according to the user's plan. This may comprise, for example, ensuring during the surgical procedure that a trajectory of the tool assembly 40, 41 is aligned with the desired pose of the pedicle screw 136. In other embodiments, the user may intra-operatively plan the desired trajectory and/or screw placement. For example, the user can position the tool assembly 40, 41 at a desired entry point relative to the vertebra V and orient the tool assembly 40, 41 until the display 35 shows that the trajectory of the longitudinal axis $A_{WT}$ is in a desired orientation. Once the user is satisfied with the trajectory, the user can provide input (e.g., touchscreen, button, foot pedal, etc.) to the control system to set this trajectory as the desired trajectory to be maintained during the procedure. The haptic object created for constraining movement of the tool assembly 40, 41 to stay along the desired trajectory may be the updated line haptic object LH, such as that shown in FIG. 22. The updated line haptic object LH may have a starting point, as described further below, a target point, which defines a desired depth of the tool assembly 40, 41, pedicle screw 136, etc., and an exit point, which when reached upon withdrawal of the tool assembly 40, 41 away from the patient, frees the robotic arm 36 from being locked on the updated line haptic object LH. Other haptic object shapes, sizes, etc. are also contemplated.

Again, in much the same manner as the tap marker 100 was controlled, while the robotic system 30 holds the tool assembly 40, 41 on the desired trajectory, the user may then manually manipulate the tool assembly 40, 41 to move (or cause movement of) the driver 138 and pedicle screw 136 along the updated line haptic object LH toward the vertebra V to insert the pedicle screw 136 in the void 154. In some cases, such as when using a passive type of robotic arm 36, the robotic system 30 constrains the user's movement of the tool assembly 40, 41 to stay along the desired trajectory by providing haptic feedback to the user should the user attempt to move the tool assembly 40, 41 in a manner that deviates from the desired trajectory. The user then drives the pedicle screw 136 into the void 154 to a desired depth. Drive speed can be controlled by the user (e.g., via a trigger or other actuator) or automatically based on the particular location of the driver 138 and/or pedicle screw 136 relative to the vertebra V. For instance, a rotational speed of the driver 138 may be set high during initial installation into the vertebral body V, but may be slowed during further installation into the vertebral body V, and set even slower during final implanting to the final depth. The control system can also monitor contact/contact force during line haptic guiding via a force sensor, force/torque sensor, torque sensor, pressure sensor, optical sensor, or the like that communicates with the robotic controller 52. If no significant contact/contact force is detected, which means the tool assembly 40, 41 is passing through soft tissue, the control system avoids activating the motor of the tool assembly 40, 41 or other power source (e.g., RF energy, ultrasonic motor, etc.). When contact with bone is detected (e.g., optically, sensed force is above a predefined threshold, etc.), the control system can activate the motor or other power source. Users can also passively feel the contact/contact force and trigger a switch to activate the power source. If the user desires to return the robotic arm 36 to a free mode, for unconstrained movement of the tool assembly 40, 41, the user can then pull the tool assembly 40, 41 back along the line haptic object LH, away from the patient, until the exit point is reached.

The virtual boundaries (e.g., line haptic objects LH) used to constrain the user's movement along the desired trajectory may also indicate, via haptic feedback, when the user has reach the desired depth of the pedicle screw 136. Separate virtual boundaries could also be used to set the desired depth. In other cases, the robotic system 30 may autonomously insert the pedicle screw 136 to the desired depths. In further cases, the robotic system 30 may initially drive the pedicle screw 136 autonomously, but then final implanting may be done manually, or vice versa. In one example, the pedicle screw 136 is placed autonomously until within a predefined distance of the final depth as determined by the navigation system 32. At this point, the user either finishes implanting the pedicle screw 136 manually with the tool assembly 40, 41 so that the user is able to feel tightening of the pedicle screws 136, or a separate tool (powered or manual) is used to complete placement of the pedicle screw 136. The user may be instructed by the control system, via displays 35, how many turns remain before the pedicle screw 136 has reached full depth, and/or the displays 35 may graphically represent the pedicle screw 136, anatomy, and/or the target point so that the user is able to easily visualize how much further driving of the pedicle screw 136 is required. In some embodiments, the void 154 may be unnecessary and the pedicle screw 136 can be placed over guide wires placed by the robotic system 10 or without any guidance.

The robotic controller 52 can be used to control insertion of the pedicle screw 136 by measuring torque associated with driving of the pedicle screw 136 with the driver 138. More specifically, the torque required to insert the pedicle screw 136 into the vertebra V increases the deeper the pedicle screw 136 is placed in the vertebra V, and further increases once an end of the void 154 is reached. As a result, torque output of the motor in the tool assembly 40, 41 can indicate whether the pedicle screw 136 has reached the desired depth and/or the end of the void 154. The robotic controller 32 monitors this torque (e.g. via a torque sensor, such as by monitoring current draw of the motor, or the like) and controls rotation of the driver 138 accordingly. For instance, once a threshold torque is reached, the driver 138 may be stopped.

It should be appreciated that the systems and methods described herein can be employed to place pedicle screws 136, other screws, other fasteners, other anchors, or other implants into a patient. So, even though pedicle screws 136 are referenced throughout as one example, the same systems and methods described herein could be utilized for treating any anatomy of the patient and/or for placing any implants into the patient, e.g., in the hip, knee, femur, tibia, face, shoulder, spine, etc. For instance, the robotic arm 36 may also be used to place a cage for a spine implant, to place rods, or to place other components, and could be used for discectomy or other procedures. Different end effectors could also be attached to the robotic arm 36 for other procedures. In some cases, the end effector may also have an articulating arm to facilitate implant insertion, i.e., placing the implant in a desired pose. The articulating arm of the end effector could simply be a miniature version of the robotic arm 36 controlled in the same manner to place the implant or could be another mechanism controlled to position the implant. It should also be appreciated that the models described herein may comprise triangulated meshes, volumetric models using voxels, or other types of 3D and/or two dimensional models in some cases. The tap marker 100 and the elongate sleeve 72 may be packaged as a sterile subassembly disposable following the surgical procedure. The elongate sleeve 72 may be color-coded or labelled to communicate information such as the diameter and/or length of the elongate sleeve 72 and/or the tap marker 100 disposed therein. Several subassemblies may be packaged within a singular package to provide a clinical and cost effective configuration. For example, four of the marker-sleeve subassemblies are packaged together for a single-level spine procedure (i.e., each pedicle of two adjacent vertebra), or six marker-sleeve subassemblies are packaged together for a two-level spine procedure.

Figure 24B:
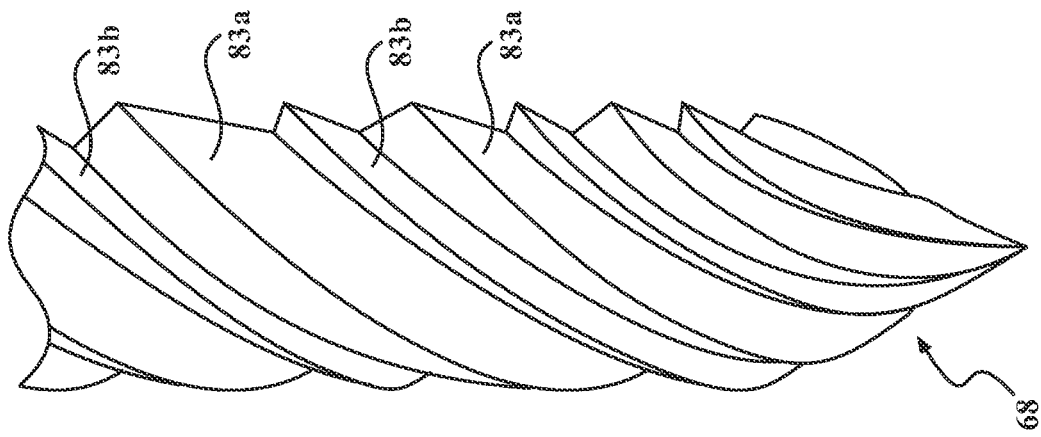
FIGS. 24A-24D are illustrations of representative geometries of a working section of the working tool.
Figure 24A:
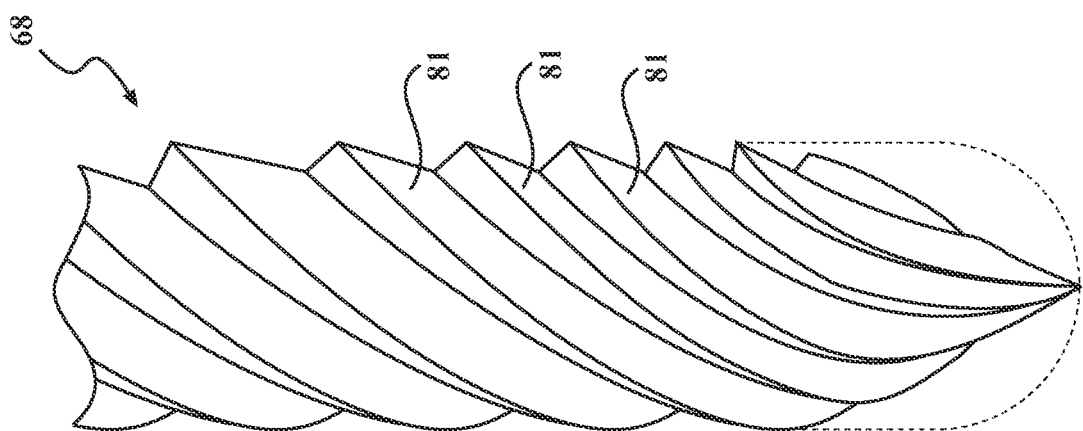
Figure 24D:
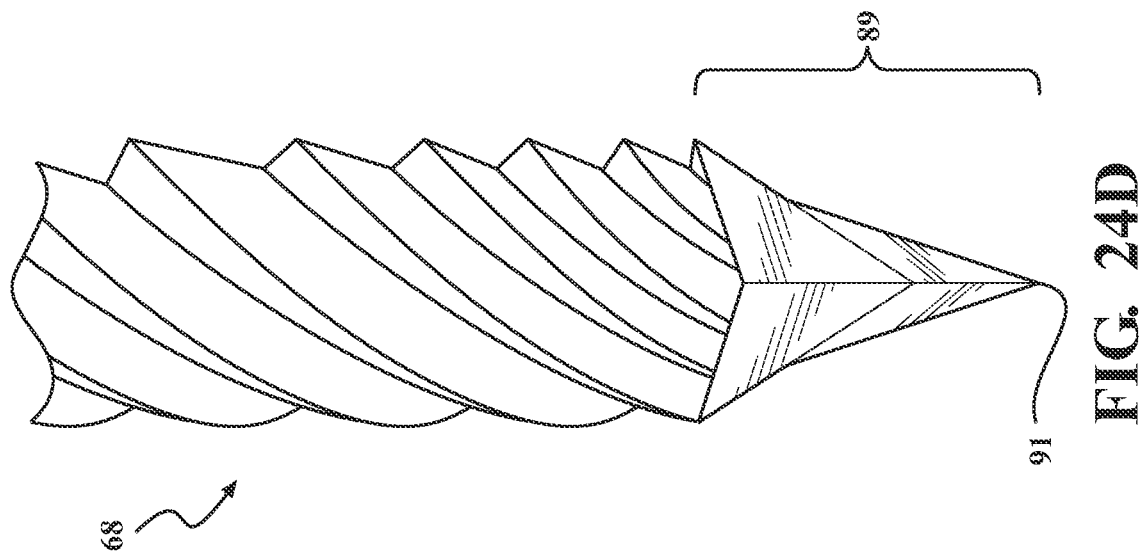
Figure 24C:
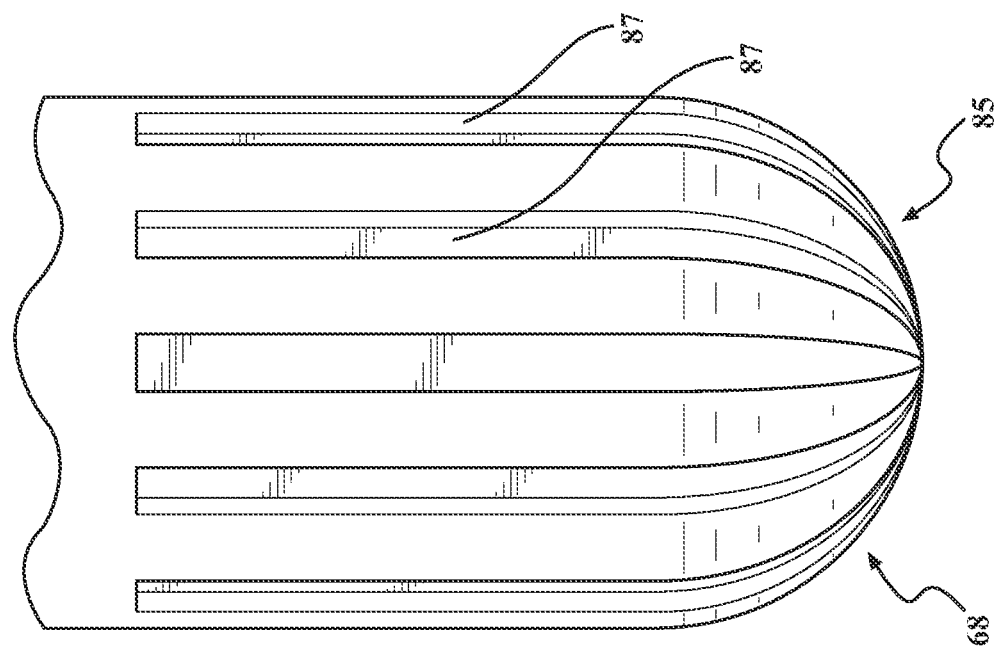

Various alternative geometries of the working section 68 of some of the working tools 46 are shown in FIGS. 24A-24C. In particular, FIG. 24A shows the working section 68 including an angular tip with one or more flutes 81 shaped to provide a plunge or axial cut capability. The tip may be sharp and one or more flutes 81 may extend from the tip upwardly with flute widths increasing in a proximal direction along the working section 68. A pitch of the flute(s)/cutting edge(s) may also increase in the proximal direction up the working section 68 from the tip. FIG. 24B shows an exemplary embodiment of the working section 68 with double or multiple flutes 83*a*, 83*b* of different geometries. The multiple flutes 83*a*, 83*b* are shown in a spiral configuration and arranged in an alternating fashion with one of the flutes 83*a* being of greater width and/or depth than the other one of the flutes 83*b*.

In another example, the multiple flutes 83*a*, 83*b* of FIG. 24B may blend into a singular shaped and sized flute (not shown) at a greater distance from the tip. The flutes 81, 83*a*, 83*b* may be adjusted to correlate to desired volumes of the bone to be removed and/or cutting rates. For example, the flutes 81, 83*a*, 83*b* may increase in width and/or depth at a greater distance from the tip. It is contemplated that the flutes 81, 83*a*, 83*b* may provide for unidirectional (i.e., continuous rotation) or bidirectional (i.e., oscillation) manipulation of the tissue.

FIG. 24C shows the working section 68 including a hemispherical ball tip 85 with a plurality of reliefs 87 generally oriented axially along the working section 68; i.e., non-spiral. The reliefs 87 may form the cutting tip similar to that of a radial bur for face and side manipulation of the tissue of the patient. The reliefs 87 may be more shallow or more deep for lesser or greater bone capture, respectively. The reliefs 87 may also have varying or alternating depths. The reliefs 87 may be generally rectangular in cross-section or may be V-shaped or U-shaped, or combinations thereof.

Referring to FIG. 24D, other suitable geometries for the working section 68 includes a plunging section 89. The plunging section 89 may be beveled (conical bevel, diamond bevel, or the like). In some cases, the plunging section 89 may comprise a diamond bevel with two or more cutting edges arranged equally about a longitudinal axis of the working section 68. The cutting edges may extend proximally from a sharp tip 91 to a cylindrical shaft of the working section 68, similar to a trocar, or may extend from the sharp tip 91 upwardly to one or more spiral flutes as shown. The plunging section 89 may extend upwardly in a double-cone or double-pyramid shape to provide plunging within the bone. In the example shown, the plunging section 89 is formed with four cutting edges that taper equally toward the longitudinal axis from a spiral flute section to a first step and then taper equally from the first step to the sharp tip 91, albeit at a steeper angle (smaller acute angle) relative to the longitudinal axis of the working section 68.

In certain embodiments, the working section 68 may range in length from ten to sixty millimeters, in width from two to ten millimeters, but other suitable sizes are contemplated based on, for example, the width and depth of the void 154 (see FIG. 22) to be provided within the bony anatomy. The working section 68 may be designed to operate within a range of 20,000 to 35,000 revolutions per minute (RPM), within a range of 10,000 to 50,000 RPM, and/or upwards of 70,000 RPM.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of operating a system for performing a surgical procedure on a vertebral body adjacent soft tissue, the system comprising a manipulator configured to move an end effector, a screw configured to be coupled to the end effector and a sleeve disposed coaxially around the screw and extending along an entire length of the screw, wherein the screw and the sleeve are releasably engaged to one another, a navigation system configured to track the vertebral body and including an insertion trajectory for the screw defined with respect to a surgical plan, and one or more controllers, the method comprising:

controlling, with the one or more controllers, the manipulator for positioning the screw and the sleeve on the insertion trajectory;

controlling, with the one or more controllers, the manipulator for advancing both the screw and the sleeve along the insertion trajectory to penetrate the soft tissue; and advancing the screw relative to the sleeve along the insertion trajectory for securing the screw to the vertebral body and for disengaging the screw from the sleeve during advancement.

2. The method of claim 1, wherein the system further includes a scalpel attachment, the method further comprising:

removably coupling the scalpel attachment to the end effector;

controlling, with the one or more controllers, the manipulator for positioning the scalpel attachment above the soft tissue on the insertion trajectory;

moving the scalpel attachment relative to the end effector along the insertion trajectory to create an incision within the soft tissue; and controlling, with the one or more controllers, the manipulator for advancing both the screw and the sleeve along the insertion trajectory within the incision of the soft tissue.

3. The method of claim 2, wherein the system further includes a dilator probe attachment, the method further comprising:

removably coupling the dilator probe attachment to the end effector;

controlling, with the one or more controllers, the manipulator for positioning the dilator probe attachment above the incision;

moving the dilator probe attachment relative to the end effector along the insertion trajectory and within the incision to create a dilated passage within the soft tissue; and controlling, with the one or more controllers, the manipulator for advancing both the screw and the sleeve within the dilated passage of the soft tissue.

4. The method of claim 1, wherein the sleeve includes a distal end opposite a proximal end, and a moveable feature formed from flexible material at the distal end, the method further comprising:

controlling, with the one or more controllers, the manipulator for advancing both the screw and the sleeve within the soft tissue with the movable feature being in an initial configuration in which the distal end of the sleeve is substantially or completely closed to prevent ingress of the soft tissue within the sleeve during advancement of the sleeve; and advancing the screw through the distal end of the sleeve to move the movable feature from the initial configuration to a deployed configuration in which the flexible material deflects outwardly to open the distal end of the sleeve.

5. The method of claim 1, wherein the sleeve includes a distal end opposite a proximal end, and at least one spike at the distal end, the method further comprising:

advancing, with the manipulator, both the screw and the sleeve within the soft tissue at a position adjacent the vertebral body; and embedding the at least one spike into the vertebral body prior to advancing the screw relative to the sleeve along the insertion trajectory to secure the screw to the vertebral body.

6. The method of claim 1, wherein the navigation system includes a localizer and a tracking device including markers, and wherein the screw secured to the vertebral body is a tap marker including a distal working portion, a proximal shaft portion, and a coupling feature on the proximal shaft portion, the method further comprising:

registering, with the navigation system, the surgical plan to the vertebral body;

controlling, with the one or more controllers, the manipulator for retracting the end effector relative to the tap marker secured to the vertebral body such that the end effector decouples from the tap marker;

resecting, with a cutting tool, tissue adjacent to the vertebral body, wherein the tissue resection alters registration of the vertebral body by the navigation system;

coupling the tracking device to the coupling feature of the tap marker to enable the markers of the tracking device to be detected by the localizer; and updating, with the navigation system, registration of the surgical plan to the vertebral body.

7. The method of claim 6, wherein the tracking device further includes a ratcheting mechanism, the method further comprising:

with the tracking device coupled to the tap marker, rotating the tracking device relative to the tap marker in a first direction about a longitudinal axis of the tap marker to orient the markers to be detected by the localizer of the navigation system.

8. The method of claim 7, further comprising:

with the tracking device coupled to the tap marker, rotating the tracking device relative to the tap marker in a second direction about the longitudinal axis opposite the first direction to cause withdrawal of the tap marker from the vertebral body, thereby providing a pilot hole within the vertebral body.

9. A method of operating a system for performing a surgical procedure on a vertebral body adjacent soft tissue, the system comprising a manipulator configured to move an end effector, a screw configured to be coupled to the end effector and a sleeve disposed coaxially around the screw, the screw and the sleeve being releasably engaged to one another, and the sleeve comprising a movable feature formed from flexible material at a distal end of the sleeve, a navigation system configured to track the vertebral body and including an insertion trajectory for the screw defined with respect to a surgical plan, and one or more controllers, the method comprising:

controlling, with the one or more controllers, the manipulator for positioning the screw and the sleeve on the insertion trajectory;

controlling, with the one or more controllers, the manipulator for advancing both the screw and the sleeve along the insertion trajectory within the soft tissue whereby the movable feature of the sleeve is in an initial configuration in which the distal end of the sleeve is substantially or completely closed for preventing ingress of the soft tissue within the sleeve during advancement; and advancing the screw along the insertion trajectory and through the distal end of the sleeve for securing the screw to the vertebral body, whereby advancing the screw through the distal end of the sleeve causes the movable feature to move from the initial configuration to a deployed configuration in which the flexible material deflects outwardly to open the distal end of the sleeve.

10. The method of claim 9, wherein the system further includes a scalpel attachment, the method further comprising:

removably coupling the scalpel attachment to the end effector;

controlling, with the one or more controllers, the manipulator for positioning the scalpel attachment above the soft tissue on the insertion trajectory;

moving the scalpel attachment relative to the end effector along the insertion trajectory to create an incision within the soft tissue; and controlling, with the one or more controllers, the manipulator for advancing both the screw and the sleeve along the insertion trajectory within the incision of the soft tissue.

11. The method of claim 10, wherein the system further includes a dilator probe attachment, the method further comprising:

removably coupling the dilator probe attachment to the end effector;

controlling, with the one or more controllers, the manipulator for positioning the dilator probe attachment above the incision;

moving the dilator probe attachment relative to the end effector along the insertion trajectory and within the incision to create a dilated passage within the soft tissue; and controlling, with the one or more controllers, the manipulator for advancing both the screw and the sleeve within the dilated passage of the soft tissue.

12. The method of claim 9, wherein the navigation system includes a localizer and a tracking device including markers, and wherein the screw secured to the vertebral body is a tap marker including a distal working portion, a proximal shaft portion, and a coupling feature on the proximal shaft portion, the method further comprising:

registering, with the navigation system, the surgical plan to the vertebral body;

controlling, with the one or more controllers, the manipulator for retracting the end effector relative to the tap marker secured to the vertebral body such that the end effector decouples from the tap marker;

resecting, with a cutting tool, tissue adjacent to the vertebral body, wherein the tissue resection alters registration of the vertebral body by the navigation system;

coupling the tracking device to the coupling feature of the tap marker to enable the markers of the tracking device to be detected by the localizer; and updating, with the navigation system, registration of the surgical plan to the vertebral body.

13. The method of claim 12, wherein the tracking device further includes a ratcheting mechanism, the method further comprising:

with the tracking device coupled to the tap marker, rotating the tracking device relative to the tap marker in a first direction about a longitudinal axis of the tap marker to orient the markers to be detected by the localizer of the navigation system.

14. The method of claim 13, further comprising:

with the tracking device coupled to the tap marker, rotating the tracking device relative to the tap marker in a second direction about the longitudinal axis opposite the first direction to cause withdrawal of the tap marker from the vertebral body, thereby providing a pilot hole within the vertebral body.

15. A method of operating a system for performing a surgical procedure on a vertebral body adjacent soft tissue, the system comprising a manipulator configured to move an end effector, a screw comprising a proximal shaft portion configured to be coupled to the end effector and a distal working portion extending from the proximal shaft portion, a sleeve disposed coaxially around the screw and wherein the screw and the sleeve are releasably engaged to one another, a navigation system configured to track the vertebral body and including an insertion trajectory for the screw defined with respect to a surgical plan, wherein the navigation system comprises a localizer and a tracking device including markers configured to be detected by the localizer and the tracking device comprising a ratcheting mechanism, and one or more controllers, the method comprising:

controlling, with the one or more controllers, the manipulator for positioning the screw and the sleeve on the insertion trajectory;

controlling, with the one or more controllers, the manipulator for advancing both the screw and the sleeve along the insertion trajectory to penetrate the soft tissue;

advancing the screw relative to the sleeve along the insertion trajectory for securing the distal working portion of the screw to the vertebral body and for disengaging the screw from the sleeve during advancement;

coupling the tracking device to the proximal shaft portion of the screw; and utilizing the ratcheting mechanism of the tracking device for rotating the markers of the tracking device relative to the screw in a first rotational direction about a longitudinal axis of the screw.

16. The method of claim 15, further comprising:

after securing the distal working portion of the screw to the vertebral body, controlling, with the one or more controllers, the manipulator for retracting the end effector relative to the screw such that the end effector decouples from the proximal shaft portion of the screw.

17. The method of claim 16, further comprising:

registering, with the navigation system, the surgical plan to the vertebral body;

resecting, with a cutting tool, tissue adjacent to the vertebral body, wherein the tissue resection alters registration of the vertebral body by the navigation system;

coupling the tracking device to the proximal shaft portion of the screw to enable the markers of the tracking device to be detected by the localizer; and updating, with the navigation system, registration of the surgical plan to the vertebral body.

18. The method of claim 15, wherein utilizing the ratcheting mechanism of the tracking device for rotating the markers of the tracking device relative to the screw in the first rotational direction further comprises orienting the markers to be detected by the localizer of the navigation system.

19. The method of claim 18, further comprising:
utilizing the ratcheting mechanism of the tracking device for rotating the markers of the tracking device relative to the screw in a second rotational direction being opposite the first rotational direction for withdrawing of the screw from the vertebral body.

20. The method of claim 15, wherein the sleeve includes a distal end opposite a proximal end, and a moveable feature formed from flexible material at the distal end, the method further comprising:
controlling, with the one or more controllers, the manipulator for advancing both the screw and the sleeve within the soft tissue with the movable feature being in an initial configuration in which the distal end of the sleeve is substantially or completely closed to prevent ingress of the soft tissue within the sleeve during advancement of the sleeve; and
advancing the screw through the distal end of the sleeve to move the movable feature from the initial configuration to a deployed configuration in which the flexible material deflects outwardly to open the distal end of the sleeve.

* * * * *